(12) United States Patent
Tanaka

(10) Patent No.: US 12,251,447 B2
(45) Date of Patent: Mar. 18, 2025

(54) COMBINED FORMULATION COMPRISING FOUR LINKED CYTOTOXIC T LYMPHOCYTE (CTL) EPITOPES AND A PD-1 PATHWAY INHIBITOR AND METHODS OF USE THEREOF TO TREAT CANCER

(71) Applicant: Taiho Pharmaceutical Co., Ltd., Tokyo (JP)

(72) Inventor: Yuki Tanaka, Ibaraki (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 967 days.

(21) Appl. No.: 17/255,672

(22) PCT Filed: Jun. 28, 2019

(86) PCT No.: PCT/JP2019/025819
§ 371 (c)(1),
(2) Date: Dec. 23, 2020

(87) PCT Pub. No.: WO2020/004622
PCT Pub. Date: Jan. 2, 2020

(65) Prior Publication Data
US 2021/0236613 A1    Aug. 5, 2021

(30) Foreign Application Priority Data
Jun. 29, 2018 (JP) ................................. 2018-124894

(51) Int. Cl.
*A61K 47/65* (2017.01)
*A61K 39/00* (2006.01)
*A61K 39/395* (2006.01)
*A61P 35/00* (2006.01)

(52) U.S. Cl.
CPC .......... *A61K 47/65* (2017.08); *A61K 39/0011* (2013.01); *A61K 39/001102* (2018.08); *A61K 39/00119* (2018.08); *A61K 39/3955* (2013.01); *A61P 35/00* (2018.01); *A61K 2039/505* (2013.01); *A61K 2039/5156* (2013.01); *A61K 2039/545* (2013.01); *A61K 2039/627* (2013.01); *A61K 2039/70* (2013.01)

(58) Field of Classification Search
CPC ........ A61K 39/001102; A61K 39/3955; A61K 47/65; A61K 2039/505; A61K 2039/545; A61K 2039/627; A61K 2039/70; A61P 35/00
See application file for complete search history.

(56) References Cited

U.S. PATENT DOCUMENTS

| | | | |
|---|---|---|---|
| 6,719,976 B1 | 4/2004 | Sone et al. | |
| 7,041,297 B1 | 5/2006 | Itoh et al. | |
| 7,718,614 B2 | 5/2010 | Itoh et al. | |
| 9,102,715 B2 | 8/2015 | Itoh et al. | |
| 9,701,729 B2 | 7/2017 | Fukaya et al. | |
| 10,137,183 B2 | 11/2018 | Fukaya et al. | |
| 2002/0128201 A1 | 9/2002 | Itoh | |
| 2003/0175288 A1 | 9/2003 | Itoh | |
| 2004/0044188 A1 | 3/2004 | Feige et al. | |
| 2006/0008463 A1 | 1/2006 | Itoh et al. | |
| 2006/0140968 A1 | 6/2006 | Itoh et al. | |
| 2007/0055049 A1 | 3/2007 | Grey et al. | |
| 2008/0014186 A1 | 1/2008 | Itoh et al. | |
| 2008/0014636 A1 | 1/2008 | Sato et al. | |
| 2008/0119399 A1 | 5/2008 | Itoh et al. | |
| 2008/0286228 A1 | 11/2008 | Tarantolo et al. | |
| 2010/0062010 A1 | 3/2010 | Nishihara et al. | |
| 2010/0278851 A1 | 11/2010 | Itoh et al. | |
| 2010/0297187 A1 | 11/2010 | Stoloff et al. | |
| 2011/0160700 A1 | 6/2011 | Nakamura et al. | |
| 2013/0164314 A1 | 6/2013 | Itoh et al. | |
| 2016/0017014 A1 | 1/2016 | Fukaya et al. | |
| 2016/0227750 A1 | 8/2016 | Harada et al. | |
| 2016/0235828 A1 | 8/2016 | Fukaya et al. | |
| 2017/0333480 A1 | 11/2017 | Cooper et al. | |
| 2021/0401745 A1 | 12/2021 | Doi | |

FOREIGN PATENT DOCUMENTS

| | | |
|---|---|---|
| CN | 1218412 A | 6/1999 |
| CN | 101854945 A | 10/2010 |
| EA | 005404 B1 | 2/2005 |
| EP | 0 923 940 B1 | 6/1999 |
| EP | 2 192 407 A2 | 6/2010 |
| EP | 2 196 209 A1 | 6/2010 |
| EP | 2 966 092 A1 | 1/2016 |
| JP | 11-318455 A | 11/1999 |

(Continued)

OTHER PUBLICATIONS

Wada et al., "Development of a novel immunoproteasome digestion assay for synthetic long peptide vaccine design," PLoS ONE, 2018, 13(7):e0199249, 1-15.
Office Action dated Mar. 31, 2020 in JP 2020-510633.
Written Opinion dated Aug. 13, 2019 in PCT/JP2019/025819.
Written Opinion dated Feb. 2, 2021 in PCT/JP2020/048667.
Written Opinion dated Feb. 4, 2020 in PCT/JP2019/043023.
Written Opinion dated Jan. 20, 2015 in PCT/JP2014/077807.
Hirayama et al., "The present status and future prospects of peptide-based cancer vaccines," International Immunology, May 28, 2016, 28(7):319-328.
Partial Supplementary European Search Report dated Apr. 7, 2022 in EP 19826598.5.

(Continued)

*Primary Examiner* — Robert S Landsman
(74) *Attorney, Agent, or Firm* — Foley & Lardner LLP

(57) ABSTRACT

Provided is a novel cancer treatment method that exhibits a significantly excellent antitumor effect and causes less adverse reactions. The present invention provides an antitumor agent wherein a peptide having 4 linked epitopes and an immune checkpoint modulator are administered in combination. An antitumor effect in humans can be evaluated by providing a cell coexpressing an epitope peptide of a human tumor antigen derived from SART2 and human HLA-A24.

14 Claims, 9 Drawing Sheets
Specification includes a Sequence Listing.

(56) References Cited

FOREIGN PATENT DOCUMENTS

| | | |
|---|---|---|
| JP | 2002-527050 A | 8/2002 |
| JP | 2003-000270 A | 1/2003 |
| JP | 2003-512057 A | 4/2003 |
| JP | 2007-145715 A | 6/2007 |
| JP | 2010-000083 A | 1/2010 |
| JP | 2012-158597 A | 8/2012 |
| JP | 5629882 B2 | 11/2014 |
| JP | 2017-535284 A | 11/2017 |
| RU | 2466737 C2 | 10/2011 |
| WO | WO-97/32600 A1 | 9/1997 |
| WO | WO-99/67288 A1 | 12/1999 |
| WO | WO-00/12701 A1 | 3/2000 |
| WO | WO-00/21551 A1 | 4/2000 |
| WO | WO-01/11044 A1 | 2/2001 |
| WO | WO-01/29220 A2 | 4/2001 |
| WO | WO-01/41741 A1 | 6/2001 |
| WO | WO-02/10369 A1 | 2/2002 |
| WO | WO-2004/029248 A1 | 4/2004 |
| WO | WO-2005/071075 A1 | 8/2005 |
| WO | WO-2005/116056 A1 | 12/2005 |
| WO | WO-2007/083763 A1 | 7/2007 |
| WO | WO-2008/007711 A1 | 1/2008 |
| WO | WO-2009/022652 A1 | 2/2009 |
| WO | WO-2009/038026 A1 | 3/2009 |
| WO | WO-2012/005161 A1 | 1/2012 |
| WO | WO-2014/136814 A1 | 9/2014 |
| WO | WO-2015/056774 A1 | 4/2015 |
| WO | WO-2015/060235 A1 | 4/2015 |
| WO | WO-2017/207814 A1 | 12/2017 |

OTHER PUBLICATIONS

Sakamoto et al., "Immunological evaluation of personalized peptide vaccination for patients with histologically unfavorable carcinoma of unknown primary site," Cancer Immunol. Immunother., 2016, 65:1223-1231.
Tanaka et al., "TAS0314, a novel multi-epitope long peptide vaccine, showed synergistic antitumor immunity with PD01/PD-L1 blockade in HLA-A*2402 mice," Scientific Reports, Oct. 14, 2020, 10:17284, 11 pages.
U.S. Appl. No. 17/788,847, filed Dec. 25, 2020, Goto, Risa.
International Search Report dated Feb. 2, 2021 in PCT/JP2020/048667.
Sakuramoto et al., "Adjuvant Chemotherapy for Gastric Cancer with S-1, an Oral Fluoropyrimidine," The New England Journal of Medicine, Nov. 1, 2007, 357(18):1810-1820.
U.S. Appl. No. 17/290,650, filed Nov. 1, 2019, Doi, Yusuke.
Balmana et al., "BRCA in breast cancer: ESMO Clinical Recommendations," Ann. Oncol., 2009, 20(Supp. 4):iv19-20.
Boon, Thierry, "Toward a Genetic Analysis of Tumor Rejection Antigens," Adv. Can. Res., 1992, 58:177-210.
Chen et al., "Advances in anti-tumor research of CTL epitope polypeptide vaccine," Journal of Clinical Medicine in Practice, 2008, 12(1):38-46, with partial English translation.
Dermer, Gerald B., "Another Anniversary for the War on Cancer," Bio/Technology, 1994, 12:320.
Ezzell, Carol, "Cancer 'Vaccines': An Idea Whose Time Has Come?", J. NIH Res., 1995, 7:46-48.
Freshney, R. Ian, Culture of Animal Cells, A Manual of Basic Technique, Alan R. Liss, Inc., 1983, New York, p. 4.
Gura, Trisha, "Systems for Identifying New Drugs are Often Faulty," Science 1997, 278:1041-1042.
Haigh et al., "Vaccine Therapy for Patients with Melanoma," Oncology, Nov. 1999, 13:1561-1582.
International Search Report dated Feb. 4, 2020 in PCT/JP2019/043023.
International Search Report dated Jan. 20, 2015, in PCT/JP2014/077807.
International Search Report dated Jun. 17, 2014, in PCT/JP2014/055555.
Ishioka et al., "Utilization of MHC Class I Transgenic Mice for Development of Minigene DNA Vaccines Encoding Multiple HLA-Restricted CTL Epitopes," The Journal of Immunology, 1999, 162:3915-3925.
Jain, Rakesh K., "Barriers to Drug Delivery in Solid Tumors," Sci. Am., Jul. 1994, 271:58-65.
Kataja et al., "Primary breast cancer: ESMO Clinical Recommendations for diagnosis, treatment and follow-up," Ann. Oncol., 2009, 20(Supp. 4):iv10-14.
Lee et al., "Increased Vaccine-Specific T Cell Frequency After Peptide-Based Vaccination Correlates with Increased Susceptibility to In Vitro Stimulation But Does Not Lead to Tumor Regression," The Journal of Immunology, 1999, 163:6292-6300.
Liao et al., "Diepitope multiple antigen peptide of hTERT trigger stronger anti-tumor immune responses in vitro," International Immunopharmacology, May 25, 2013, 16(4):444-450.
Moncada et al., "Simple method for the preparation of antigen emulsions for immunization," Journal of Immunological Methods, 1993, 162(1):133-140.
Nelson et al., "Screening for Breast Cancer: An Update for the U.S. Preventive Services Task Force," Ann. Intern. Med., 2009, 151:727-737.
Noguchi et al., "A randomized phase II trial of personalized peptide vaccine plus low dose estramustine phosphate (EMP) versus standard dose EMP in patients with castration resistant prostate cancer," Cancer Immunol. Immunother., 2010, 59(7):1001-1009.
Noguchi et al., "Assessment of immunological biomarkers in patients with advanced cancer treated by personalized peptide vaccination," Cancer Biology & Therapy, Dec. 15, 2010, 10(12):1266-1279.
Office Action and Search Report dated Aug. 29, 2016, in RU 2015142659, with English translation.
Office Action dated Aug. 2, 2018, in CN 201480057880.4.
Office Action dated Mar. 8, 2016, in JP 2015-504352.
Qing-Feng et al., "In Vitro Specific anti-Chronic Myeloid Leukemia Cell Effect of CTL by a Multiple Epitope BCR-ABL Fusion Protein," Letters in Biotechnology, Jul. 2009, 20(4):517-519, English abstract on p. 517.
Search Report dated Oct. 19, 2016 in EP 14761112.3.
Sette et al., "Nine major HLA class I supertypes account for the vast preponderance of HLA-A and -B polymorphism," Immunogenetics, 1999, 50(3-4):201-212.
Skosyrev et al., "The dependence of stability of the green fluorescent protein-obelin hybrids on the nature of their constituent modules and the structure of the amino acid linker," Bioorg. Khim., Sep.-Oct. 2001, 27(5):364-371, with English translation.
Spitler, Lynn E., M.D., "Cancer Vaccines: The interferon Analogy," Cancer Biotherapy, 1995, 10(1):1-3.
Supplementary European Search Report dated Jul. 18, 2017, in EP 14856540.1.
Taiwanese Office Action dated Jan. 21, 2015 in TW 103108019.
Terasaki et al., "Phase I Trial of a Personalized Peptide Vaccine for Patients Positive for Human Leukocyte Antigen-A24 With Recurrent or Progressive Glioblastoma Multiforme," Journal of Clinical Oncology, Jan. 20, 2011, 29(3):337-344.
Van der Burg et al., "Improved peptide vaccine strategies, creating synthetic artificial infections to maximize immune efficacy," Advanced Drug Delivery Reviews, Aug. 12, 2006, 58(8):916-930.
Yanagimoto et al., "Immunological evaluation of personalized peptide vaccination with gemcitabine for pancreatic cancer," Cancer Sci., Apr. 2007, 98(4):605-611.
Zhao et al., "Balancing the Pharmacokinetics and Pharmacodynamics of Interferon-α2b and Human Serum Albumin Fusion Protein by Proteolytic or Reductive Cleavage Increases in Vivo Therapeutics Efficacy," Mol. Pharm., 2012, 9(3):664-670.
Nakao et al., "Identification of a Gene Coding for a New Squamous Cell Carcinoma Antigen Recognized by the CTL," J. Immunol., 2000, 164(5):2565-2574.
Office Action dated Dec. 22, 2022 in KR 10-2021-7002430.
International Search Report dated Aug. 13, 2019 in PCT/JP2019/025819.
Ito et al., "Induction of CTL Responses by Simultaneous Administration of Liposomal Peptide Vaccine with Anti-CD40 and Anti-CTLA-4 mAb," J. Immunol., 2000, 164:1230-1235.

(56) References Cited

OTHER PUBLICATIONS

Osawa et al., "Identification of HLA-A24-Restricted Novel T Cell Epitope Peptides Derived from P-Cadherin and Kinesin Family Member 20A," Journal of Biomedicine and Biotechnology, 2012, 1012:848042, 10 pages.
Ott et al., "An immunogenic personal neoantigen vaccine for patients with melanoma," Nature, Jul. 13, 2017, 547:217-221.
Pardoll et al., "The blockade of immune checkpoints in cancer immunotherapy," Nat. Rev. Cancer, 2012, 12(4):252-264.
Rosenberg et al., "Cancer immunotherapy: moving beyond current vaccines," Nature Medicine, Sep. 2004, 10(9):909-915.
Topalian et al., "Safety, Activity, and Immune Correlates of Anti-PD-1 Antibody in Cancer," The New England Journal of Medicine, Jun. 28, 2012, 366(26):2443-2454.
Shah, R.R., Brito, L.A., O'Hagan, D.T., Amiji, M.M. (2015). Emulsions as Vaccine Adjuvants. In: Foged C.; Rades, T., Perrie, Y., Hook, S. (eds), Subunit Vaccine Delivery, Advances in Delivery Science and Technology, Springer, New York, NY. (Year: 2015).
Non-Final Office Action dated Oct. 21, 2024 in U.S. Appl. No. 17/290,650.
Hailemichael et al., "Persistent antigen at vaccination sites induces tumor-specific CD8+ T cell sequestration, dysfunction and deletion," Nature Medicine, Apr. 2013 (online Mar. 3, 2013), 19(4):465-472.
Office Action dated Jan. 31, 2025 in EP 20906353.6.
Rini et al., "IMA901, a multipeptide cancer vaccine, plus sunitinib versus sunitinib alone, as first-line therapy for advanced or metastatic renal cell carcinoma (Imprint): a multicentre, open-label, randomised, controlled, phase 3 trial," Lancet Oncology, Oct. 3, 2016, 17:1599-1611.

a b

```
SEQUENCE LISTING

<160> NUMBER OF SEQ ID NOS: 45

<210> SEQ ID NO 1
<211> LENGTH: 9
<212> TYPE: PRT
<213> ORGANISM: Homo sapiens

<400> SEQUENCE: 1

Lys Leu Val Glu Arg Leu Gly Ala Ala
1               5

<210> SEQ ID NO 2
<211> LENGTH: 9
<212> TYPE: PRT
<213> ORGANISM: Homo sapiens

<400> SEQUENCE: 2

Ala Ser Leu Asp Ser Asp Pro Trp Val
1               5

<210> SEQ ID NO 3
<211> LENGTH: 9
<212> TYPE: PRT
<213> ORGANISM: Homo sapiens

<400> SEQUENCE: 3

Ala Leu Val Glu Phe Glu Asp Val Leu
1               5

<210> SEQ ID NO 4
<211> LENGTH: 9
<212> TYPE: PRT
<213> ORGANISM: Homo sapiens

<400> SEQUENCE: 4

Leu Leu Gln Ala Glu Ala Pro Arg Leu
1               5

<210> SEQ ID NO 5
<211> LENGTH: 9
```

```
<212> TYPE: PRT
<213> ORGANISM: Homo sapiens

<400> SEQUENCE: 5

Asp Tyr Ser Ala Arg Trp Asn Glu Ile
1               5

<210> SEQ ID NO 6
<211> LENGTH: 10
<212> TYPE: PRT
<213> ORGANISM: Homo sapiens

<400> SEQUENCE: 6

Val Tyr Asp Tyr Asn Cys His Val Asp Leu
1               5                   10

<210> SEQ ID NO 7
<211> LENGTH: 9
<212> TYPE: PRT
<213> ORGANISM: Homo sapiens

<400> SEQUENCE: 7

Leu Tyr Ala Trp Glu Pro Ser Phe Leu
1               5

<210> SEQ ID NO 8
<211> LENGTH: 10
<212> TYPE: PRT
<213> ORGANISM: Homo sapiens

<400> SEQUENCE: 8

Asp Tyr Leu Arg Ser Val Leu Glu Asp Phe
1               5                   10

<210> SEQ ID NO 9
<211> LENGTH: 9
<212> TYPE: PRT
<213> ORGANISM: Homo sapiens

<400> SEQUENCE: 9

Gln Ile Arg Pro Ile Phe Ser Asn Arg
1               5

<210> SEQ ID NO 10
<211> LENGTH: 10
<212> TYPE: PRT
<213> ORGANISM: Homo sapiens

<400> SEQUENCE: 10

Ile Leu Glu Gln Ser Gly Glu Trp Trp Lys
1               5                   10

<210> SEQ ID NO 11
<211> LENGTH: 10
<212> TYPE: PRT
<213> ORGANISM: Homo sapiens

<400> SEQUENCE: 11

Val Ile Gln Asn Leu Glu Arg Gly Tyr Arg
1               5                   10

<210> SEQ ID NO 12
<211> LENGTH: 10
<212> TYPE: PRT
<213> ORGANISM: Homo sapiens
```

```
<400> SEQUENCE: 12

Lys Leu Lys His Tyr Gly Pro Gly Trp Val
1               5                   10

<210> SEQ ID NO 13
<211> LENGTH: 9
<212> TYPE: PRT
<213> ORGANISM: Homo sapiens

<400> SEQUENCE: 13

Arg Leu Gln Glu Trp Cys Ser Val Ile
1               5

<210> SEQ ID NO 14
<211> LENGTH: 9
<212> TYPE: PRT
<213> ORGANISM: Homo sapiens

<400> SEQUENCE: 14

Ile Leu Gly Glu Leu Arg Glu Lys Val
1               5

<210> SEQ ID NO 15
<211> LENGTH: 10
<212> TYPE: PRT
<213> ORGANISM: Homo sapiens

<400> SEQUENCE: 15

Asp Tyr Val Arg Glu His Lys Asp Asn Ile
1               5                   10

<210> SEQ ID NO 16
<211> LENGTH: 9
<212> TYPE: PRT
<213> ORGANISM: Homo sapiens

<400> SEQUENCE: 16

His Tyr Thr Asn Ala Ser Asp Gly Leu
1               5

<210> SEQ ID NO 17
<211> LENGTH: 10
<212> TYPE: PRT
<213> ORGANISM: Homo sapiens

<400> SEQUENCE: 17

Asn Tyr Ser Val Arg Tyr Arg Pro Gly Leu
1               5                   10

<210> SEQ ID NO 18
<211> LENGTH: 10
<212> TYPE: PRT
<213> ORGANISM: Homo sapiens

<400> SEQUENCE: 18

Arg Tyr Leu Thr Gln Glu Thr Asn Lys Val
1               5                   10

<210> SEQ ID NO 19
<211> LENGTH: 43
<212> TYPE: PRT
<213> ORGANISM: Artificial
<220> FEATURE:
<223> OTHER INFORMATION: synthetic peptide
```

```
<400> SEQUENCE: 19

Asp Tyr Ser Ala Arg Trp Asn Glu Ile Arg Arg Val Tyr Asp Tyr Asn
1               5                   10                  15

Cys His Val Asp Leu Arg Arg Gln Ile Arg Pro Ile Phe Ser Asn Arg
            20                  25                  30

Arg Arg Leu Leu Gln Ala Glu Ala Pro Arg Leu
        35                  40

<210> SEQ ID NO 20
<211> LENGTH: 43
<212> TYPE: PRT
<213> ORGANISM: Artificial
<220> FEATURE:
<223> OTHER INFORMATION: synthetic peptide

<400> SEQUENCE: 20

Gln Ile Arg Pro Ile Phe Ser Asn Arg Arg Asp Tyr Ser Ala Arg
1               5                   10                  15

Trp Asn Glu Ile Arg Arg Val Tyr Asp Tyr Asn Cys His Val Asp Leu
            20                  25                  30

Arg Arg Leu Leu Gln Ala Glu Ala Pro Arg Leu
        35                  40

<210> SEQ ID NO 21
<211> LENGTH: 43
<212> TYPE: PRT
<213> ORGANISM: Artificial
<220> FEATURE:
<223> OTHER INFORMATION: synthetic peptide

<400> SEQUENCE: 21

Val Tyr Asp Tyr Asn Cys His Val Asp Leu Arg Arg Asp Tyr Ser Ala
1               5                   10                  15

Arg Trp Asn Glu Ile Arg Arg Gln Ile Arg Pro Ile Phe Ser Asn Arg
            20                  25                  30

Arg Arg Leu Leu Gln Ala Glu Ala Pro Arg Leu
        35                  40

<210> SEQ ID NO 22
<211> LENGTH: 43
<212> TYPE: PRT
<213> ORGANISM: Artificial
<220> FEATURE:
<223> OTHER INFORMATION: synthetic peptide

<400> SEQUENCE: 22

Val Tyr Asp Tyr Asn Cys His Val Asp Leu Arg Arg Gln Ile Arg Pro
1               5                   10                  15

Ile Phe Ser Asn Arg Arg Arg Asp Tyr Ser Ala Arg Trp Asn Glu Ile
            20                  25                  30

Arg Arg Leu Leu Gln Ala Glu Ala Pro Arg Leu
        35                  40

<210> SEQ ID NO 23
<211> LENGTH: 43
<212> TYPE: PRT
<213> ORGANISM: Artificial
<220> FEATURE:
<223> OTHER INFORMATION: synthetic peptide

<400> SEQUENCE: 23
```

Gln Ile Arg Pro Ile Phe Ser Asn Arg Arg Val Tyr Asp Tyr Asn
1               5                   10                  15

Cys His Val Asp Leu Arg Arg Asp Tyr Ser Ala Arg Trp Asn Glu Ile
            20                  25                  30

Arg Arg Leu Leu Gln Ala Glu Ala Pro Arg Leu
        35                  40

<210> SEQ ID NO 24
<211> LENGTH: 43
<212> TYPE: PRT
<213> ORGANISM: Artificial
<220> FEATURE:
<223> OTHER INFORMATION: synthetic peptide

<400> SEQUENCE: 24

Asp Tyr Ser Ala Arg Trp Asn Glu Ile Arg Arg Gln Ile Arg Pro Ile
1               5                   10                  15

Phe Ser Asn Arg Arg Val Tyr Asp Tyr Asn Cys His Val Asp Leu
            20                  25                  30

Arg Arg Leu Leu Gln Ala Glu Ala Pro Arg Leu
        35                  40

<210> SEQ ID NO 25
<211> LENGTH: 43
<212> TYPE: PRT
<213> ORGANISM: Artificial
<220> FEATURE:
<223> OTHER INFORMATION: synthetic peptide

<400> SEQUENCE: 25

Asp Tyr Ser Ala Arg Trp Asn Glu Ile Arg Arg Gln Ile Arg Pro Ile
1               5                   10                  15

Phe Ser Asn Arg Arg Val Tyr Asp Tyr Asn Cys His Val Asp Leu
            20                  25                  30

Arg Arg Ala Ser Leu Asp Ser Asp Pro Trp Val
        35                  40

<210> SEQ ID NO 26
<211> LENGTH: 44
<212> TYPE: PRT
<213> ORGANISM: Artificial
<220> FEATURE:
<223> OTHER INFORMATION: synthetic peptide

<400> SEQUENCE: 26

Asp Tyr Ser Ala Arg Trp Asn Glu Ile Arg Arg Gln Ile Arg Pro Ile
1               5                   10                  15

Phe Ser Asn Arg Arg Val Tyr Asp Tyr Asn Cys His Val Asp Leu
            20                  25                  30

Arg Arg Ile Leu Glu Gln Ser Gly Glu Trp Trp Lys
        35                  40

<210> SEQ ID NO 27
<211> LENGTH: 46
<212> TYPE: PRT
<213> ORGANISM: Artificial
<220> FEATURE:
<223> OTHER INFORMATION: synthetic peptide

<400> SEQUENCE: 27

Arg Arg Arg Asp Tyr Ser Ala Arg Trp Asn Glu Ile Arg Arg Gln Ile
1               5                   10                  15

Arg Pro Ile Phe Ser Asn Arg Arg Val Tyr Asp Tyr Asn Cys His
            20                  25                  30

Val Asp Leu Arg Arg Leu Leu Gln Ala Glu Ala Pro Arg Leu
        35                  40                  45

<210> SEQ ID NO 28
<211> LENGTH: 47
<212> TYPE: PRT
<213> ORGANISM: Artificial
<220> FEATURE:
<223> OTHER INFORMATION: synthetic peptide

<400> SEQUENCE: 28

Arg Arg Arg Arg Asp Tyr Ser Ala Arg Trp Asn Glu Ile Arg Arg Gln
1               5                   10                  15

Ile Arg Pro Ile Phe Ser Asn Arg Arg Val Tyr Asp Tyr Asn Cys
            20                  25                  30

His Val Asp Leu Arg Arg Leu Leu Gln Ala Glu Ala Pro Arg Leu
        35                  40                  45

<210> SEQ ID NO 29
<211> LENGTH: 27
<212> TYPE: DNA
<213> ORGANISM: Homo sapiens

<400> SEQUENCE: 29
gactacagtg cccgctggaa tgaaatt                                       27

<210> SEQ ID NO 30
<211> LENGTH: 182
<212> TYPE: PRT
<213> ORGANISM: Homo sapiens

<400> SEQUENCE: 30

Gly Ser His Ser Met Arg Tyr Phe Ser Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Glu Thr
    50                  55                  60

Gly Lys Val Lys Ala His Ser Gln Thr Asp Arg Glu Asn Leu Arg Ile
65                  70                  75                  80

Ala Leu Arg Tyr Tyr Asn Gln Ser Glu Ala Gly Ser His Thr Leu Gln
                85                  90                  95

Met Met Phe Gly Cys Asp Val Gly Ser Asp Gly Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Ile Thr Lys
    130                 135                 140

Arg Lys Trp Glu Ala Ala His Val Ala Glu Gln Arg Ala Tyr Leu
145                 150                 155                 160

Glu Gly Thr Cys Val Asp Gly Leu Arg Arg Tyr Leu Glu Asn Gly Lys
                165                 170                 175

Glu Thr Leu Gln Arg Thr
            180

<210> SEQ ID NO 31
<211> LENGTH: 546
<212> TYPE: DNA
<213> ORGANISM: Homo sapiens

<400> SEQUENCE: 31

```
ggatctcact ccatgaggta tttctccaca tccgtgtccc ggcccggccg cggggagccc      60
cgcttcatcg ccgtgggcta cgtggacgac acgcagttcg tgcggttcga cagcgacgcc     120
gcgagccaga ggatggagcc gcgggcgccg tggatagagc aggaggggcc ggagtattgg     180
gacgaggaga cagggaaagt gaaggcccac tcacagactg accgagagaa cctgcggatc     240
gcgctccgct actacaacca gagcgaggcc ggttctcaca ccctccagat gatgtttggc     300
tgcgacgtgg ggtcgacgg gcgcttcctc cgcgggtacc accagtacgc ctacgacggc     360
aaggattaca tcgccctgaa agaggacctg cgctcttgga ccgcggcgga catggcggct     420
cagatcacca gcgcaagtg ggaggcggcc catgtggcgg agcagcagag agcctacctg     480
gagggcacgt gcgtggacgg gctccgcaga tacctggaga cgggaagga gacgctgcag     540
cgcacg                                                               546
```

<210> SEQ ID NO 32
<211> LENGTH: 33
<212> TYPE: PRT
<213> ORGANISM: Artificial
<220> FEATURE:
<223> OTHER INFORMATION: synthetic peptide

<400> SEQUENCE: 32

```
Met Ala Val Met Ala Pro Arg Thr Leu Val Leu Leu Leu Ser Gly Ala
1               5                   10                  15
Leu Ala Leu Thr Gln Thr Trp Ala Asp Tyr Ser Ala Arg Trp Asn Glu
            20                  25                  30
Ile
```

<210> SEQ ID NO 33
<211> LENGTH: 102
<212> TYPE: DNA
<213> ORGANISM: Artificial
<220> FEATURE:
<223> OTHER INFORMATION: synthetic peptide

<400> SEQUENCE: 33

```
atggccgtca tggcgccccg aaccctcgtc ctgctactct cgggggccct ggccctgacc      60
cagacctggg cagactacag tgcccgctgg aatgaaattt ga                        102
```

<210> SEQ ID NO 34
<211> LENGTH: 476
<212> TYPE: PRT
<213> ORGANISM: Artificial
<220> FEATURE:
<223> OTHER INFORMATION: synthetic peptide

<400> SEQUENCE: 34

```
Met Ala Val Met Ala Pro Arg Thr Leu Val Leu Leu Leu Ser Gly Ala
1               5                   10                  15
Leu Ala Leu Thr Gln Thr Trp Ala Ile Gln Arg Thr Pro Lys Ile Gln
            20                  25                  30
Val Tyr Ser Arg His Pro Ala Glu Asn Gly Lys Ser Asn Phe Leu Asn
        35                  40                  45
```

-continued

```
Cys Tyr Val Ser Gly Phe His Pro Ser Asp Ile Glu Val Asp Leu Leu
 50              55                  60
Lys Asn Gly Glu Arg Ile Glu Lys Val Glu His Ser Asp Leu Ser Phe
 65                  70                  75                  80
Ser Lys Asp Trp Ser Phe Tyr Leu Leu Tyr Tyr Thr Glu Phe Thr Pro
                 85                  90                  95
Thr Glu Lys Asp Glu Tyr Ala Cys Arg Val Asn His Val Thr Leu Ser
             100                 105                 110
Gln Pro Lys Ile Val Lys Trp Asp Arg Asp Met Gly Gly Gly Gly Ser
         115                 120                 125
Gly Gly Gly Gly Ser Gly Gly Gly Ser Gly Ser His Ser Met Arg
    130                 135                 140
Tyr Phe Ser Thr Ser Val Ser Arg Pro Gly Arg Gly Glu Pro Arg Phe
145                 150                 155                 160
Ile Ala Val Gly Tyr Val Asp Asp Thr Gln Phe Val Arg Phe Asp Ser
                165                 170                 175
Asp Ala Ala Ser Gln Arg Met Glu Pro Arg Ala Pro Trp Ile Glu Gln
            180                 185                 190
Glu Gly Pro Glu Tyr Trp Asp Glu Glu Thr Gly Lys Val Lys Ala His
        195                 200                 205
Ser Gln Thr Asp Arg Glu Asn Leu Arg Ile Ala Leu Arg Tyr Tyr Asn
    210                 215                 220
Gln Ser Glu Ala Gly Ser His Thr Leu Gln Met Met Phe Gly Cys Asp
225                 230                 235                 240
Val Gly Ser Asp Gly Arg Phe Leu Arg Gly Tyr His Gln Tyr Ala Tyr
                245                 250                 255
Asp Gly Lys Asp Tyr Ile Ala Leu Lys Glu Asp Leu Arg Ser Trp Thr
            260                 265                 270
Ala Ala Asp Met Ala Ala Gln Ile Thr Lys Arg Lys Trp Glu Ala Ala
        275                 280                 285
His Val Ala Glu Gln Gln Arg Ala Tyr Leu Glu Gly Thr Cys Val Asp
    290                 295                 300
Gly Leu Arg Arg Tyr Leu Glu Asn Gly Lys Glu Thr Leu Gln Arg Thr
305                 310                 315                 320
Asp Ser Pro Lys Ala His Val Thr His His Pro Arg Ser Lys Gly Glu
                325                 330                 335
Val Thr Leu Arg Cys Trp Ala Leu Gly Phe Tyr Pro Ala Asp Ile Thr
            340                 345                 350
Leu Thr Trp Gln Leu Asn Gly Glu Glu Leu Thr Gln Asp Met Glu Leu
        355                 360                 365
Val Glu Thr Arg Pro Ala Gly Asp Gly Thr Phe Gln Lys Trp Ala Ser
    370                 375                 380
Val Val Val Pro Leu Gly Lys Glu Gln Asn Tyr Thr Cys Arg Val Tyr
385                 390                 395                 400
His Glu Gly Leu Pro Glu Pro Leu Thr Leu Arg Trp Glu Pro Pro
                405                 410                 415
Ser Thr Asp Ser Tyr Met Val Ile Val Ala Val Leu Gly Val Leu Gly
            420                 425                 430
Ala Met Ala Ile Ile Gly Ala Val Val Ala Phe Val Met Lys Arg Arg
        435                 440                 445
Arg Asn Thr Gly Gly Lys Gly Gly Asp Tyr Ala Leu Ala Pro Gly Ser
    450                 455                 460
Gln Ser Ser Glu Met Ser Leu Arg Asp Cys Lys Ala
```

<210> SEQ ID NO 35
<211> LENGTH: 1431
<212> TYPE: DNA
<213> ORGANISM: Artificial
<220> FEATURE:
<223> OTHER INFORMATION: synthetic peptide

<400> SEQUENCE: 35

```
atggccgtca tggcgccccg aaccctcgtc ctgctactct cgggggccct ggccctgacc      60
cagacctggg cgatccagcg tactccaaag attcaggttt actcacgtca tccagcagag     120
aatggaaagt caaatttcct gaattgctat gtgtctgggt tcatccatc cgacattgaa      180
gttgacttac tgaagaatgg agagagaatt gaaaaagtgg agcattcaga cttgtctttc     240
agcaaggact ggtctttcta tctcttgtac tacactgaat tcaccccac tgaaaaagat      300
gagtatgcct ccgtgtgaa ccatgtgact ttgtcacagc caagatagt taagtgggat       360
cgagacatgg gaggtggcgg atccggcgga ggcggctcgg gtggcggcgg ctctggatct     420
cactccatga ggtatttctc acatccgtg tcccggcccg ccgcgggga gccccgcttc       480
atcgccgtgg gctacgtgga cgacacgcag ttcgtgcggt tcgacagcga cgccgcgagc     540
cagaggatgg agccgcgggc gccgtggata gagcaggagg ggccggagta ttgggacgag     600
gagacaggga aagtgaaggc ccactcacag actgaccgag agaacctgcg gatcgcgctc     660
cgctactaca accagagcga ggccggttct cacaccctcc agatgatgtt tggctgcgac     720
gtggggtcgg acgggcgctt cctccgcggg taccaccagt acgcctacga cggcaaggat     780
tacatcgccc tgaaagagga cctgcgctct ggaccgcgg cggacatggc ggctcagatc     840
accaagcgca gtgggaggc ggcccatgtg gcggagcagc agagagccta cctggagggc     900
acgtgcgtgg acgggctccg cagatacctg gagaacggga aggagacgct gcagcgcacg     960
gattccccaa aggcacatgt gacccatcac cccagatcta aaggtgaagt caccctgagg    1020
tgctgggccc tgggcttcta ccctgctgac atcaccctga cctggcagtt gaatggggag    1080
gagctgaccc aggacatgga gcttgtggag accaggcctg caggggatgg aaccttccag    1140
aagtgggcat ctgtggtggt gcctcttggg aaggagcaga attacacatg ccgtgtgtac    1200
catgaggggc tgcctgagcc cctcaccctg agatgggagc tcctccgtc cactgactct    1260
tacatggtga tcgttgctgt tctgggtgtc cttggagcta tggccatcat tggagctgtg    1320
gtggcttttg tgatgaagag aaggagaaac acaggtggaa aaggagggga ctatgctctg    1380
gctccaggct cccagagctc tgaaatgtct ctccgagatt gtaaagcgtg a            1431
```

<210> SEQ ID NO 36
<211> LENGTH: 99
<212> TYPE: PRT
<213> ORGANISM: Homo sapiens

<400> SEQUENCE: 36

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

-continued

```
Leu Tyr Tyr Thr Glu Phe Thr Pro Thr Glu Lys Asp Glu Tyr Ala Cys
 65                  70                  75                  80

Arg Val Asn His Val Thr Leu Ser Gln Pro Lys Ile Val Lys Trp Asp
                 85                  90                  95

Arg Asp Met

<210> SEQ ID NO 37
<211> LENGTH: 156
<212> TYPE: PRT
<213> ORGANISM: Mus musculus

<400> SEQUENCE: 37

Asp Ser Pro Lys Ala His Val Thr His Pro Arg Ser Lys Gly Glu
1               5                  10                  15

Val Thr Leu Arg Cys Trp Ala Leu Gly Phe Tyr Pro Ala Asp Ile Thr
             20                  25                  30

Leu Thr Trp Gln Leu Asn Gly Glu Glu Leu Thr Gln Asp Met Glu Leu
         35                  40                  45

Val Glu Thr Arg Pro Ala Gly Asp Gly Thr Phe Gln Lys Trp Ala Ser
     50                  55                  60

Val Val Val Pro Leu Gly Lys Glu Gln Asn Tyr Thr Cys Arg Val Tyr
 65                  70                  75                  80

His Glu Gly Leu Pro Glu Pro Leu Thr Leu Arg Trp Glu Pro Pro
                 85                  90                  95

Ser Thr Asp Ser Tyr Met Val Ile Val Ala Val Leu Gly Val Leu Gly
                100                 105                 110

Ala Met Ala Ile Ile Gly Ala Val Ala Phe Val Met Lys Arg Arg
             115                 120                 125

Arg Asn Thr Gly Gly Lys Gly Gly Asp Tyr Ala Leu Ala Pro Gly Ser
         130                 135                 140

Gln Ser Ser Glu Met Ser Leu Arg Asp Cys Lys Ala
145                 150                 155

<210> SEQ ID NO 38
<211> LENGTH: 29
<212> TYPE: DNA
<213> ORGANISM: Artificial
<220> FEATURE:
<223> OTHER INFORMATION: primer 1

<400> SEQUENCE: 38
tcaagcttaa ctagcatggc cgtcatggc                                    29

<210> SEQ ID NO 39
<211> LENGTH: 39
<212> TYPE: DNA
<213> ORGANISM: Artificial
<220> FEATURE:
<223> OTHER INFORMATION: primer 2

<400> SEQUENCE: 39
ttaaacctcg agtgctcacg ctttacaatc tcggagaga                         39

<210> SEQ ID NO 40
<211> LENGTH: 46
<212> TYPE: DNA
<213> ORGANISM: Artificial
<220> FEATURE:
<223> OTHER INFORMATION: primer 3
```

-continued

```
<400> SEQUENCE: 40
ctcaaatttc attccagcgg gcactgtagt ctgcccaggt ctgggt              46

<210> SEQ ID NO 41
<211> LENGTH: 48
<212> TYPE: DNA
<213> ORGANISM: Artificial
<220> FEATURE:
<223> OTHER INFORMATION: primer 4

<400> SEQUENCE: 41
gcagactaca gtgcccgctg gaatgaaatt tgagcactcg aggttttaa           48

<210> SEQ ID NO 42
<211> LENGTH: 14
<212> TYPE: DNA
<213> ORGANISM: Artificial
<220> FEATURE:
<223> OTHER INFORMATION: primer 5

<400> SEQUENCE: 42
atggccgtca tggc                                                 14

<210> SEQ ID NO 43
<211> LENGTH: 18
<212> TYPE: DNA
<213> ORGANISM: Artificial
<220> FEATURE:
<223> OTHER INFORMATION: primer 6

<400> SEQUENCE: 43
tcaaatttca ttccagcg                                             18

<210> SEQ ID NO 44
<211> LENGTH: 45
<212> TYPE: PRT
<213> ORGANISM: Artificial
<220> FEATURE:
<223> OTHER INFORMATION: synthetic peptide

<400> SEQUENCE: 44

Asp Tyr Val Arg Glu His Lys Asp Asn Ile Arg Arg Tyr Leu Thr
1               5                   10                  15

Gln Glu Thr Asn Lys Val Arg Arg Lys Leu Val Glu Arg Leu Gly Ala
            20                  25                  30

Ala Arg Arg Ile Leu Glu Gln Ser Gly Glu Trp Trp Lys
        35                  40                  45

<210> SEQ ID NO 45
<211> LENGTH: 47
<212> TYPE: PRT
<213> ORGANISM: Artificial
<220> FEATURE:
<223> OTHER INFORMATION: synthetic peptide

<400> SEQUENCE: 45

Arg Arg Arg Arg Leu Tyr Ala Trp Glu Pro Ser Phe Leu Arg Arg
1               5                   10                  15

Leu Gln Glu Trp Cys Ser Val Ile Arg Arg Asp Tyr Leu Arg Ser Val
            20                  25                  30

Leu Glu Asp Phe Arg Arg Ala Ser Leu Asp Ser Asp Pro Trp Val
        35                  40                  45
```

COMBINED FORMULATION COMPRISING FOUR LINKED CYTOTOXIC T LYMPHOCYTE (CTL) EPITOPES AND A PD-1 PATHWAY INHIBITOR AND METHODS OF USE THEREOF TO TREAT CANCER

CROSS-REFERENCE TO RELATED APPLICATIONS

This application is the U.S. National Stage of PCT/JP2019/025819, filed Jun. 28, 2019, which claims priority to JP 2018-124894, filed Jun. 29, 2018.

The instant application contains a Sequence Listing which has been submitted in ASCII format via EFS-WEB and is hereby incorporated by reference in its entirety. Said ASCII copy, created on Dec. 22, 2020, is named sequence.txt and is 21,515 bytes.

TECHNICAL FIELD

The present invention relates to cancer chemotherapy using a peptide having 4 linked CTL epitopes comprising 4 linked peptides capable of inducing HLA-A-restricted CTL responses, and an immune checkpoint modulator (immune checkpoint molecule modulator). The present invention also relates to a cell coexpressing an epitope peptide of a human tumor antigen derived from SART2 and human HLA-A24, which can be suitably used for evaluating the effect of the cancer chemotherapy of the present invention.

Background Art

Cancer peptide vaccine has been expected as a novel therapy for cancers for a long period of time. However, the efficacy of the treatment is very limited, though clinical studies about cancer peptide vaccines have been conducted throughout the world since 1990 when epitope peptides of human tumor were identified (Non Patent Literature 1).

The mechanism of treatment of cancer peptide vaccine is that a T cell receptor (TCR) of an epitope specific cytotoxic T lymphocyte (CTL) recognizes major histocompatibility complex (MHC) presenting an antigen peptide on cancer cell surface and the CTL kills the cancer cell. Human MHC is also called human leukocyte antigen (HLA), and the types of HLA are known to be highly polymorphic. Hence, development of cancer peptide vaccines only for particular HLA alleles has been attempted. However, cancer vaccines target limited HLA alleles, and disadvantageously, patients with the other HLA alleles cannot gain benefits from cancer peptide vaccines. In addition, requirement of HLA typing prior to treatment would increase some burdens to patients by delaying the treatment initiation. Accordingly, research and development of cancer peptide vaccines that are applicable to all cancer patients without HLA typing have been desired.

In order to solve this problem, a peptide having 4 linked CTL epitopes obtained by linking various CTL epitope peptides capable of inducing any one or more of HLA-A2, HLA-A24, HLA-A26, or HLA-A3 supertype-restricted CTL response has been reported (Patent Literature 1).

Molecular mechanisms involved in suppression and activation of immune cells have been revealed in recent years. T cell immune responses are regulated by TCR signals and co-signals. The co-signals include a costimulation signal and a coinhibition signal which positively and negatively, respectively, regulate the signals mediated by TCR, and control T cell immune responses. Cancer cells take advantage of this mechanism and induce T cell exhaustion by suppressing antigen specific activation of T cells. In recent years, control of tumor immune escape by enhancing in vivo antitumor immune responses of cancer patients through strengthening of costimulation signals or blocking of coinhibition signals has been considered to be effective for cancer treatment, and various cancer immunotherapies targeting costimulatory molecules or coinhibitory molecules have been proposed (Non Patent Literature 2). For example, nivolumab is used as an immune checkpoint modulator that activates T cells by inhibiting the binding of PD-1 to its ligand (PD-L1 and PD-L2), in treatment of malignant melanoma, etc. (Non Patent Literatures 2 and 3).

However, an enhanced antitumor effect by combining a peptide having 4 linked CTL epitopes with an immune checkpoint modulator has not been shown.

CITATION LIST

Patent Literature

Patent Literature 1: International Publication No. WO 2015/060235

Non Patent Literature

Non Patent Literature 1: Nature Med., 10 (9): 909-15 (2004)
Non Patent Literature 2: Nat. Rev. Cancer., 12 (4): 252-64 (2012)
Non Patent Literature 3: N. Engl. J. Med., 366 (26): 2443-54 (2012)

SUMMARY OF INVENTION

Technical Problem

An object of the present invention is to provide a novel cancer treatment method that exhibits a significantly excellent antitumor effect and causes less adverse reactions, by administering a peptide having 4 linked CTL epitopes and an immune checkpoint modulator in combination. Another object of the present invention is to provide a cell coexpressing an epitope peptide of a human tumor antigen derived from SART2 and human HLA-A24, which can be suitably used for evaluating the effect of an antitumor agent in humans.

Solution to Problem

The present inventor has studied an antitumor effect by administering a peptide having 4 linked CTL epitopes and an anti-PD-1 antibody or an anti-PD-L1 antibody as an immune checkpoint modulator in combination, and consequently found that the antitumor effect is significantly enhanced without developing severe adverse reactions, as compared with the drugs used alone. The present inventor has further established a cell coexpressing an epitope peptide of a human tumor antigen derived from SART2 and human HLA-A24, and established a method that can evaluate the antitumor effect of an epitope peptide of a human tumor antigen on the cell.

Specifically, the present invention provides the following inventions.

[1] An antitumor agent for use in combination with an immune checkpoint modulator, comprising, as an active ingredient, a peptide having 4 linked epitopes comprising 4 CTL epitope peptides linked via linkers, wherein in the peptide having 4 linked epitopes,
the epitope peptide as shown in SEQ ID NO: 5 (PEP5), and
3 epitope peptides selected from the group consisting of
the epitope peptide as shown in SEQ ID NO: 1 (PEP1),
the epitope peptide as shown in SEQ ID NO: 2 (PEP2),
the epitope peptide as shown in SEQ ID NO: 4 (PEP4),
the epitope peptide as shown in SEQ ID NO: 6 (PEP6),
the epitope peptide as shown in SEQ ID NO: 7 (PEP7),
the epitope peptide as shown in SEQ ID NO: 8 (PEP8),
the epitope peptide as shown in SEQ ID NO: 9 (PEP9),
the epitope peptide as shown in SEQ ID NO: 10 (PEP10), the epitope peptide as shown in SEQ ID NO: 13 (PEP13), the epitope peptide as shown in SEQ ID NO: 15 (PEP15), the epitope peptide as shown in SEQ ID NO: 17 (PEP17) and the epitope peptide as shown in SEQ ID NO: 18 (PEP18)
are linked via linkers, wherein the peptide having 4 linked epitopes optionally further comprises a peptide sequence consisting of hydrophilic amino acids, and wherein the peptide having 4 linked epitopes has any one of features selected from the following features (1) to (3):
(1) the peptide comprises PEP2 at the C terminus (except for peptides comprising PEP7 and PEP8 at the N terminus successively disposed in such order from the N terminus via a linker);
(2) the peptide comprises PEP4 at the C terminus; and
(3) the peptide comprises PEP10 at the C terminus.

[2] The antitumor agent according to [1], wherein the epitope peptides comprised in the peptide having 4 linked epitopes are composed of
PEP5,
PEP6,
PEP9, and
one epitope peptide selected from the group consisting of PEP2, PEP4 and PEP10, and the peptide having 4 linked epitopes has PEP2, PEP4 or PEP10 at the C terminus.

[3] The antitumor agent according to [1] or [2], wherein the peptide having 4 linked epitopes consists of a sequence selected from the following sequences:
PEP5-(L)-PEP5-(L)-PEP6-(L)-PEP4;
PEP5-(L)-PEP5-(L)-PEP6-(L)-PEP2; and
PEP5-(L)-PEP5-(L)-PEP6-(L)-PEP10, wherein
"(L)" represents a linker.

[4] The antitumor agent according to any of [1] to [3], wherein the linker is an amino acid linker.

[5] The antitumor agent according to [4], wherein the amino acid linker is an arginine dimer composed of two arginine residues linked to each other or an arginine trimer composed of three arginine residues linked to each other.

[6] The antitumor agent according to any of [1] to [5], wherein the peptide sequence consisting of hydrophilic amino acids is linked to the N terminus and composed of an arginine trimer composed of three arginine residues linked to each other or an arginine tetramer composed of four arginine residues linked to each other.

[7] The antitumor agent according to any of [1] to [6], wherein the peptide having 4 linked epitopes is as shown in SEQ ID NO: 24, SEQ ID NO: 25, or SEQ ID NO: 26.

[8] The antitumor agent according to any of [1] to [7], wherein the immune checkpoint modulator is at least one selected from the group consisting of a PD-1 pathway antagonist, an ICOS pathway agonist, a CTLA-4 pathway antagonist and a CD28 pathway agonist.

[9] The antitumor agent according to any of [1] to [7], wherein the immune checkpoint modulator is at least one selected from the group consisting of a PD-1 pathway antagonist and a CTLA-4 pathway antagonist.

[10] The antitumor agent according to any of [1] to [7], wherein the immune checkpoint modulator is a PD-1 pathway antagonist.

[11] The antitumor agent according to any of [8] to [10], wherein the PD-1 pathway antagonist is at least one selected from the group consisting of an anti-PD-1 antibody, an anti-PD-L1 antibody and an anti-PD-L2 antibody.

[12] The antitumor agent according to any of [8] to [10], wherein the PD-1 pathway antagonist is at least one selected from the group consisting of an anti-PD-1 antibody and an anti-PD-L1 antibody.

[13] The antitumor agent according to [11] or [12], wherein the anti-PD-1 antibody is nivolumab or pembrolizumab, and the anti-PD-L1 antibody is atezolizumab, durvalumab or avelumab.

[14] The antitumor agent according to [8] or [9], wherein the CTLA-4 pathway antagonist is an anti-CTLA-4 antibody.

[15] The antitumor agent according to [14], wherein the anti-CTLA-4 antibody is ipilimumab or tremelimumab.

[16] An antitumor agent for treating a cancer patient given an immune checkpoint modulator, comprising a peptide having 4 linked epitopes as an active ingredient, wherein
in the peptide having 4 linked epitopes,
the epitope peptide as shown in SEQ ID NO: 5 (PEP5), and
3 epitope peptides selected from the group consisting of
the epitope peptide as shown in SEQ ID NO: 1 (PEP1),
the epitope peptide as shown in SEQ ID NO: 2 (PEP2),
the epitope peptide as shown in SEQ ID NO: 4 (PEP4),
the epitope peptide as shown in SEQ ID NO: 6 (PEP6),
the epitope peptide as shown in SEQ ID NO: 7 (PEP7),
the epitope peptide as shown in SEQ ID NO: 8 (PEP8),
the epitope peptide as shown in SEQ ID NO: 9 (PEP5),
the epitope peptide as shown in SEQ ID NO: 10 (PEP10), the epitope peptide as shown in SEQ ID NO: 13 (PEP13), the epitope peptide as shown in SEQ ID NO: 15 (PEP15), the epitope peptide as shown in SEQ ID NO: 17 (PEP17) and the epitope peptide as shown in SEQ ID NO: 18 (PEP18)
are linked via linkers, wherein the peptide having 4 linked epitopes optionally further comprises a peptide sequence consisting of hydrophilic amino acids, and wherein the peptide having 4 linked epitopes has any one of features selected from the following features (1) to (3):
(1) the peptide comprises PEP2 at the C terminus (except for peptides comprising PEP7 and PEP8 at the N terminus successively disposed in such order from the N terminus via a linker);
(2) the peptide comprises PEP4 at the C terminus; and
(3) the peptide comprises PEP10 at the C terminus.

[17] An antitumor agent for treating a cancer patient given a peptide having 4 linked epitopes, comprising an immune checkpoint modulator, wherein
in the peptide having 4 linked epitopes,
the epitope peptide as shown in SEQ ID NO: 5 (PEP5), and
3 epitope peptides selected from the group consisting of
the epitope peptide as shown in SEQ ID NO: 1 (PEP1),
the epitope peptide as shown in SEQ ID NO: 2 (PEP2),
the epitope peptide as shown in SEQ ID NO: 4 (PEP4),
the epitope peptide as shown in SEQ ID NO: 6 (PEP6),
the epitope peptide as shown in SEQ ID NO: 7 (PEP7),
the epitope peptide as shown in SEQ ID NO: 8 (PEP8),
the epitope peptide as shown in SEQ ID NO: 9 (PEP5), the epitope peptide as shown in SEQ ID NO: 10 (PEP10), the epitope peptide as shown in SEQ ID NO: 13 (PEP13), the epitope peptide as shown in SEQ ID NO: 15 (PEP15), the epitope peptide as shown in SEQ ID NO: 17 (PEP17) and the epitope peptide as shown in SEQ ID NO: 18 (PEP18)

are linked via linkers, wherein the peptide having 4 linked epitopes optionally further comprises a peptide sequence consisting of hydrophilic amino acids, wherein the peptide having 4 linked epitopes has any one of features selected from the following features (1) to (3):

(1) the peptide comprises PEP2 at the C terminus (except for peptides comprising PEP7 and PEP8 at the N terminus successively disposed in such order from the N terminus via a linker);

(2) the peptide comprises PEP4 at the C terminus; and (3) the peptide comprises PEP10 at the C terminus, and wherein the immune checkpoint modulator is at least one selected from the group consisting of a PD-1 pathway antagonist, an ICOS pathway agonist, a CTLA-4 pathway antagonist and a CD28 pathway agonist.

[18] A combined formulation comprising a peptide having 4 linked epitopes and an immune checkpoint modulator in combination, wherein in the peptide having 4 linked epitopes, the epitope peptide as shown in SEQ ID NO: 5 (PEP5), and 3 epitope peptides selected from the group consisting of
the epitope peptide as shown in SEQ ID NO: 1 (PEP1),
the epitope peptide as shown in SEQ ID NO: 2 (PEP2),
the epitope peptide as shown in SEQ ID NO: 4 (PEP4),
the epitope peptide as shown in SEQ ID NO: 6 (PEP6),
the epitope peptide as shown in SEQ ID NO: 7 (PEP7),
the epitope peptide as shown in SEQ ID NO: 8 (PEP8),
the epitope peptide as shown in SEQ ID NO: 9 (PEP9),
the epitope peptide as shown in SEQ ID NO: 10 (PEP10), the epitope peptide as shown in SEQ ID NO: 13 (PEP13), the epitope peptide as shown in SEQ ID NO: 15 (PEP15), the epitope peptide as shown in SEQ ID NO: 17 (PEP17) and the epitope peptide as shown in SEQ ID NO: 18 (PEP18)

are linked via linkers, wherein the peptide having 4 linked epitopes optionally further comprises a peptide sequence consisting of hydrophilic amino acids, and wherein the peptide having 4 linked epitopes has any one of features selected from the following features (1) to (3):

(1) the peptide comprises PEP2 at the C terminus (except for peptides comprising PEP7 and PEP8 at the N terminus successively disposed in such order from the N terminus via a linker);

(2) the peptide comprises PEP4 at the C terminus; and (3) the peptide comprises PEP10 at the C terminus.

[19] An antitumor effect enhancer for enhancing the antitumor effect of an immune checkpoint modulator, comprising a peptide having 4 linked epitopes as an active ingredient, wherein in the peptide having 4 linked epitopes, the epitope peptide as shown in SEQ ID NO: 5 (PEP5), and 3 epitope peptides selected from the group consisting of
the epitope peptide as shown in SEQ ID NO: 1 (PEP1),
the epitope peptide as shown in SEQ ID NO: 2 (PEP2),
the epitope peptide as shown in SEQ ID NO: 4 (PEP4),
the epitope peptide as shown in SEQ ID NO: 6 (PEP6),
the epitope peptide as shown in SEQ ID NO: 7 (PEP7),
the epitope peptide as shown in SEQ ID NO: 8 (PEP8),
the epitope peptide as shown in SEQ ID NO: 9 (PEP9),
the epitope peptide as shown in SEQ ID NO: 10 (PEP10), the epitope peptide as shown in SEQ ID NO: 13 (PEP13), the epitope peptide as shown in SEQ ID NO: 15 (PEP15), the epitope peptide as shown in SEQ ID NO: 17 (PEP17) and the epitope peptide as shown in SEQ ID NO: 18 (PEP18)

are linked via linkers, wherein the peptide having 4 linked epitopes optionally further comprises a peptide sequence consisting of hydrophilic amino acids, and wherein the peptide having 4 linked epitopes has any one of features selected from the following features (1) to (3):

(1) the peptide comprises PEP2 at the C terminus (except for peptides comprising PEP7 and PEP8 at the N terminus successively disposed in such order from the N terminus via a linker);

(2) the peptide comprises PEP4 at the C terminus; and (3) the peptide comprises PEP10 at the C terminus.

[20] An antitumor agent comprising a peptide having 4 linked epitopes comprising 4 CTL epitope peptides linked via linkers, and an immune checkpoint modulator, as active ingredients, wherein in the peptide having 4 linked epitopes, the epitope peptide as shown in SEQ ID NO: 5 (PEP5), and 3 epitope peptides selected from the group consisting of
the epitope peptide as shown in SEQ ID NO: 1 (PEP1),
the epitope peptide as shown in SEQ ID NO: 2 (PEP2),
the epitope peptide as shown in SEQ ID NO: 4 (PEP4),
the epitope peptide as shown in SEQ ID NO: 6 (PEP6),
the epitope peptide as shown in SEQ ID NO: 7 (PEP7),
the epitope peptide as shown in SEQ ID NO: 8 (PEP8),
the epitope peptide as shown in SEQ ID NO: 9 (PEP5),
the epitope peptide as shown in SEQ ID NO: 10 (PEP10), the epitope peptide as shown in SEQ ID NO: 13 (PEP13), the epitope peptide as shown in SEQ ID NO: 15 (PEP15), the epitope peptide as shown in SEQ ID NO: 17 (PEP17) and the epitope peptide as shown in SEQ ID NO: 18 (PEP18)

are linked via linkers, wherein the peptide having 4 linked epitopes optionally further comprises a peptide sequence consisting of hydrophilic amino acids, and wherein the peptide having 4 linked epitopes has any one of features selected from the following features (1) to (3):

(1) the peptide comprises PEP2 at the C terminus (except for peptides comprising PEP7 and PEP8 at the N terminus successively disposed in such order from the N terminus via a linker);

(2) the peptide comprises PEP4 at the C terminus; and (3) the peptide comprises PEP10 at the C terminus.

[21] A kit formulation comprising a peptide having 4 linked epitopes and an instruction for use, the instruction for use stating that the peptide having 4 linked epitopes and an immune checkpoint modulator are administered in combination to a cancer patient, wherein in the peptide having 4 linked epitopes, the epitope peptide as shown in SEQ ID NO: 5 (PEP5), and 3 epitope peptides selected from the group consisting of
the epitope peptide as shown in SEQ ID NO: 1 (PEP1),
the epitope peptide as shown in SEQ ID NO: 2 (PEP2),
the epitope peptide as shown in SEQ ID NO: 4 (PEP4),
the epitope peptide as shown in SEQ ID NO: 6 (PEP6),
the epitope peptide as shown in SEQ ID NO: 7 (PEP7),
the epitope peptide as shown in SEQ ID NO: 8 (PEP8),
the epitope peptide as shown in SEQ ID NO: 9 (PEP5),
the epitope peptide as shown in SEQ ID NO: 10 (PEP10), the epitope peptide as shown in SEQ ID NO:

13 (PEP13), the epitope peptide as shown in SEQ ID NO: 15 (PEP15), the epitope peptide as shown in SEQ ID NO: 17 (PEP17) and the epitope peptide as shown in SEQ ID NO: 18 (PEP18)

are linked via linkers, wherein the peptide having 4 linked epitopes optionally further comprises a peptide sequence consisting of hydrophilic amino acids, and wherein the peptide having 4 linked epitopes has any one of features selected from the following features (1) to (3):

(1) the peptide comprises PEP2 at the C terminus (except for peptides comprising PEP7 and PEP8 at the N terminus successively disposed in such order from the N terminus via a linker);

(2) the peptide comprises PEP4 at the C terminus; and (3) the peptide comprises PEP10 at the C terminus.

[22] A cell which have been introduced a polynucleotide encoding an epitope peptide of a human tumor antigen derived from SART2 and a polynucleotide encoding α1 and α2 regions of human HLA-A24 have been introduced.

[23] A cell which have been introduced a polynucleotide selected from the following polynucleotides (a) to (e):

(a) a polynucleotide encoding a polypeptide comprising the amino acid sequence as shown in SEQ ID NO: 5;

(b) a polynucleotide encoding a polypeptide comprising an amino acid sequence having substitution, deletion, or addition of one or several amino acids in the amino acid sequence as shown in SEQ ID NO: 5;

(c) a polynucleotide encoding a polypeptide comprising an amino acid sequence having 90% or higher identity to the amino acid sequence as shown in SEQ ID NO: 5;

(d) a polynucleotide comprising the nucleotide sequence as shown in SEQ ID NO: 29; and (e) a polynucleotide comprising a nucleotide sequence having 90% or higher identity to the nucleotide sequence as shown in SEQ ID NO: 29; and a polynucleotide selected from the following polynucleotides (f) to (j):

(f) a polynucleotide encoding a polypeptide comprising the amino acid sequence as shown in SEQ ID NO: 30;

(g) a polynucleotide encoding a polypeptide comprising an amino acid sequence having substitution, deletion, or addition of one or several amino acids in the amino acid sequence as shown in SEQ ID NO: 30;

(h) a polynucleotide encoding a polypeptide comprising an amino acid sequence having 90% or higher identity to the amino acid sequence as shown in SEQ ID NO: 30;

(i) a polynucleotide comprising the nucleotide sequence as shown in SEQ ID NO: 31; and (j) a polynucleotide comprising a nucleotide sequence having 90% or higher identity to the nucleotide sequence as shown in SEQ ID NO: 31

[24] A cell which have been introduced a polynucleotide selected from the following polynucleotides (k) to (o):

(k) a polynucleotide encoding a polypeptide consisting of the amino acid sequence as shown in SEQ ID NO: 32;

(l) a polynucleotide encoding a polypeptide consisting of an amino acid sequence having substitution, deletion, or addition of one or several amino acids in the amino acid sequence as shown in SEQ ID NO: 32;

(m) a polynucleotide encoding a polypeptide consisting of an amino acid sequence having 90% or higher identity to the amino acid sequence as shown in SEQ ID NO: 32;

(n) a polynucleotide consisting of the nucleotide sequence as shown in SEQ ID NO: 33; and (o) a polynucleotide consisting of a nucleotide sequence having 90% or higher identity to the nucleotide sequence as shown in SEQ ID NO: 33; and a polynucleotide selected from the following polynucleotides (p) to (t):

(p) a polynucleotide encoding a polypeptide consisting of the amino acid sequence as shown in SEQ ID NO: 34;

(q) a polynucleotide encoding a polypeptide consisting of an amino acid sequence having substitution, deletion, or addition of one or several amino acids in the amino acid sequence as shown in SEQ ID NO: 34;

(r) a polynucleotide encoding a polypeptide consisting of an amino acid sequence having 90% or higher identity to the amino acid sequence as shown in SEQ ID NO: 34;

(s) a polynucleotide consisting of the nucleotide sequence as shown in SEQ ID NO: 35; and (t) a polynucleotide consisting of a nucleotide sequence having 90% or higher identity to the nucleotide sequence as shown in SEQ ID NO: 35

[25] The cell according to any of [22] to [24] for evaluating the antitumor effect of an epitope peptide of a human tumor antigen derived from SART2.

[26] The cell according to any of [22] to [24] for evaluating the antitumor effect of a peptide having 4 linked epitopes and/or an immune checkpoint modulator, wherein in the peptide having 4 linked epitopes, the epitope peptide as shown in SEQ ID NO: 5 (PEP5), and 3 epitope peptides selected from the group consisting of the epitope peptide as shown in SEQ ID NO: 1 (PEP1), the epitope peptide as shown in SEQ ID NO: 2 (PEP2), the epitope peptide as shown in SEQ ID NO: 4 (PEP4), the epitope peptide as shown in SEQ ID NO: 6 (PEP6), the epitope peptide as shown in SEQ ID NO: 7 (PEP7), the epitope peptide as shown in SEQ ID NO: 8 (PEP8), the epitope peptide as shown in SEQ ID NO: 9 (PEP5), the epitope peptide as shown in SEQ ID NO: 10 (PEP10), the epitope peptide as shown in SEQ ID NO: 13 (PEP13), the epitope peptide as shown in SEQ ID NO: 15 (PEP15), the epitope peptide as shown in SEQ ID NO: 17 (PEP17) and the epitope peptide as shown in SEQ ID NO: 18 (PEP18)

are linked via linkers, wherein the peptide having 4 linked epitopes optionally further comprises a peptide sequence consisting of hydrophilic amino acids, and wherein the peptide having 4 linked epitopes has any one of features selected from the following features (1) to (3):

(1) the peptide comprises PEP2 at the C terminus (except for peptides comprising PEP7 and PEP8 at the N terminus successively disposed in such order from the N terminus via a linker);

(2) the peptide comprises PEP4 at the C terminus; and (3) the peptide comprises PEP10 at the C terminus.

[27] A method for evaluating the antitumor effect of an epitope peptide of a human tumor antigen derived from SART2 using the cell according to any of [22] to [24], comprising the following steps (I) and (II):

(I) administering the epitope peptide of a human tumor antigen derived from SART2 to a human HLA-A24 gene knock-in non-immunodeficient non-human animal; and (II) transplanting the cell according to any of [22] to [24] to the human HLA-A24 gene knock-in non-immunodeficient non-human animal.

[28] A method for evaluating the antitumor effect of a peptide having 4 linked epitopes and/or an immune checkpoint modulator using the cell according to any of [22] to [24], comprising the following steps (I) and (II):
(I) administering the peptide having 4 linked epitopes and/or the immune checkpoint modulator to a human HLA-A24 gene knock-in non-immunodeficient non-human animal; and
(II) transplanting the cell according to any of [22] to [24] to the human HLA-A24 gene knock-in non-immunodeficient non-human animal, wherein
in the peptide having 4 linked epitopes,
the epitope peptide as shown in SEQ ID NO: 5 (PEP5), and
3 epitope peptides selected from the group consisting of
the epitope peptide as shown in SEQ ID NO: 1 (PEP1),
the epitope peptide as shown in SEQ ID NO: 2 (PEP2),
the epitope peptide as shown in SEQ ID NO: 4 (PEP4),
the epitope peptide as shown in SEQ ID NO: 6 (PEP6),
the epitope peptide as shown in SEQ ID NO: 7 (PEP7),
the epitope peptide as shown in SEQ ID NO: 8 (PEP8),
the epitope peptide as shown in SEQ ID NO: 9 (PEP5),
the epitope peptide as shown in SEQ ID NO: 10 (PEP10), the epitope peptide as shown in SEQ ID NO: 13 (PEP13), the epitope peptide as shown in SEQ ID NO: 15 (PEP15), the epitope peptide as shown in SEQ ID NO: 17 (PEP17) and the epitope peptide as shown in SEQ ID NO: 18 (PEP18)
are linked via linkers, wherein the peptide having 4 linked epitopes optionally further comprises a peptide sequence consisting of hydrophilic amino acids, and wherein the peptide having 4 linked epitopes has any one of features selected from the following features (1) to (3):
(1) the peptide comprises PEP2 at the C terminus (except for peptides comprising PEP7 and PEP8 at the N terminus successively disposed in such order from the N terminus via a linker);
(2) the peptide comprises PEP4 at the C terminus; and
(3) the peptide comprises PEP10 at the C terminus.

[29] A pharmaceutical composition for prevention and/or treatment of tumor, comprising a peptide having 4 linked epitopes comprising 4 CTL epitope peptides linked via linkers, an immune checkpoint modulator, and a pharmaceutically acceptable carrier, wherein
in the peptide having 4 linked epitopes,
the epitope peptide as shown in SEQ ID NO: 5 (PEP5), and
3 epitope peptides selected from the group consisting of
the epitope peptide as shown in SEQ ID NO: 1 (PEP1),
the epitope peptide as shown in SEQ ID NO: 2 (PEP2),
the epitope peptide as shown in SEQ ID NO: 4 (PEP4),
the epitope peptide as shown in SEQ ID NO: 6 (PEP6),
the epitope peptide as shown in SEQ ID NO: 7 (PEP7),
the epitope peptide as shown in SEQ ID NO: 8 (PEP8),
the epitope peptide as shown in SEQ ID NO: 9 (PEP9),
the epitope peptide as shown in SEQ ID NO: 10 (PEP10), the epitope peptide as shown in SEQ ID NO: 13 (PEP13), the epitope peptide as shown in SEQ ID NO: 15 (PEP15), the epitope peptide as shown in SEQ ID NO: 17 (PEP17) and the epitope peptide as shown in SEQ ID NO: 18 (PEP18)
are linked via linkers, wherein the peptide having 4 linked epitopes optionally further comprises a peptide sequence consisting of hydrophilic amino acids, and wherein the peptide having 4 linked epitopes has any one of features selected from the following features (1) to (3):
(1) the peptide comprises PEP2 at the C terminus (except for peptides comprising PEP7 and PEP8 at the N terminus successively disposed in such order from the N terminus via a linker);
(2) the peptide comprises PEP4 at the C terminus; and
(3) the peptide comprises PEP10 at the C terminus.

[30] A method for preventing and/or treating tumor by combining a peptide having 4 linked epitopes comprising 4 CTL epitope peptides linked via linkers with an immune checkpoint modulator, comprising a step of administering a prophylactically and/or therapeutically effective amount of the peptide having 4 linked epitopes to a patient, wherein
in the peptide having 4 linked epitopes,
the epitope peptide as shown in SEQ ID NO: 5 (PEP5), and
3 epitope peptides selected from the group consisting of
the epitope peptide as shown in SEQ ID NO: 1 (PEP1),
the epitope peptide as shown in SEQ ID NO: 2 (PEP2),
the epitope peptide as shown in SEQ ID NO: 4 (PEP4),
the epitope peptide as shown in SEQ ID NO: 6 (PEP6),
the epitope peptide as shown in SEQ ID NO: 7 (PEP7),
the epitope peptide as shown in SEQ ID NO: 8 (PEP8),
the epitope peptide as shown in SEQ ID NO: 9 (PEP9),
the epitope peptide as shown in SEQ ID NO: 10 (PEP10), the epitope peptide as shown in SEQ ID NO: 13 (PEP13), the epitope peptide as shown in SEQ ID NO: 15 (PEP15), the epitope peptide as shown in SEQ ID NO: 17 (PEP17) and the epitope peptide as shown in SEQ ID NO: 18 (PEP18)
are linked via linkers, wherein the peptide having 4 linked epitopes optionally further comprises a peptide sequence consisting of hydrophilic amino acids, and wherein the peptide having 4 linked epitopes has any one of features selected from the following features (1) to (3):
(1) the peptide comprises PEP2 at the C terminus (except for peptides comprising PEP7 and PEP8 at the N terminus successively disposed in such order from the N terminus via a linker);
(2) the peptide comprises PEP4 at the C terminus; and
(3) the peptide comprises PEP10 at the C terminus.

[31] The method according to [30], wherein the peptide having 4 linked epitopes is administered to the patient before administration of the immune checkpoint modulator, simultaneously with administration of the immune checkpoint modulator, or after administration of the immune checkpoint modulator.

[32] The method according to [30] for enhancing the antitumor effect of the immune checkpoint modulator.

[33] A peptide having 4 linked epitopes comprising 4 CTL epitope peptides linked via linkers, for use in prevention and/or treatment of tumor in combination with an immune checkpoint modulator, wherein
in the peptide having 4 linked epitopes,
the epitope peptide as shown in SEQ ID NO: 5 (PEP5), and
3 epitope peptides selected from the group consisting of
the epitope peptide as shown in SEQ ID NO: 1 (PEP1),
the epitope peptide as shown in SEQ ID NO: 2 (PEP2),
the epitope peptide as shown in SEQ ID NO: 4 (PEP4),
the epitope peptide as shown in SEQ ID NO: 6 (PEP6),
the epitope peptide as shown in SEQ ID NO: 7 (PEP7),
the epitope peptide as shown in SEQ ID NO: 8 (PEP8),
the epitope peptide as shown in SEQ ID NO: 9 (PEP5),
the epitope peptide as shown in SEQ ID NO: 10 (PEP10), the epitope peptide as shown in SEQ ID NO: 13 (PEP13), the epitope peptide as shown in SEQ ID NO: 15 (PEP15), the epitope peptide as shown in SEQ ID NO: 17 (PEP17) and the epitope peptide as shown in SEQ ID NO: 18 (PEP18) are linked via linkers, wherein the peptide having 4 linked epitopes optionally further comprises a peptide sequence consisting of hydrophilic amino acids, wherein the peptide having 4 linked epitopes has any one of features selected from the following features (1) to (3):
 (1) the peptide comprises PEP2 at the C terminus (except for peptides comprising PEP7 and PEP8 at the N terminus successively disposed in such order from the N terminus via a linker);
 (2) the peptide comprises PEP4 at the C terminus; and
 (3) the peptide comprises PEP10 at the C terminus, and
wherein the peptide having 4 linked epitopes is administered before administration of the immune checkpoint modulator, simultaneously with administration of the immune checkpoint modulator, or after administration of the immune checkpoint modulator.

[34] The peptide having 4 linked epitopes according to [33], wherein the peptide having 4 linked epitopes is as shown in SEQ ID NO: 24, SEQ ID NO: 25, or SEQ ID NO: 26.

[35] The peptide having 4 linked epitopes according to [33] or [34], wherein the immune checkpoint modulator is a PD-1 pathway antagonist.

[36] The peptide having 4 linked epitopes according to any of [33] to [35], wherein the PD-1 pathway antagonist is at least one selected from the group consisting of an anti-PD-1 antibody and an anti-PD-L1 antibody.

[37] The peptide having 4 linked epitopes according to any of [33] to [36], wherein the anti-PD-1 antibody is nivolumab or pembrolizumab, and the anti-PD-L1 antibody is atezolizumab, durvalumab or avelumab.

[38] The peptide having 4 linked epitopes for use in enhancing the antitumor effect of the immune checkpoint modulator.

[39] A peptide having 4 linked epitopes and an immune checkpoint modulator for use in a method for preventing and/or treating tumor in a patient, the peptide having 4 linked epitopes and the immune checkpoint modulator being administered simultaneously or separately to the patient, wherein the peptide having 4 linked epitopes comprises 4 CTL epitope peptides linked via linkers,
 wherein the epitope peptide as shown in SEQ ID NO: 5 (PEP5), and
 3 epitope peptides selected from the group consisting of the epitope peptide as shown in SEQ ID NO: 1 (PEP1), the epitope peptide as shown in SEQ ID NO: 2 (PEP2), the epitope peptide as shown in SEQ ID NO: 4 (PEP4), the epitope peptide as shown in SEQ ID NO: 6 (PEP6), the epitope peptide as shown in SEQ ID NO: 7 (PEP7), the epitope peptide as shown in SEQ ID NO: 8 (PEP8), the epitope peptide as shown in SEQ ID NO: 9 (PEP5), the epitope peptide as shown in SEQ ID NO: 10 (PEP10), the epitope peptide as shown in SEQ ID NO: 13 (PEP13), the epitope peptide as shown in SEQ ID NO: 15 (PEP15), the epitope peptide as shown in SEQ ID NO: 17 (PEP17) and the epitope peptide as shown in SEQ ID NO: 18 (PEP18)
are linked via linkers, wherein the peptide having 4 linked epitopes optionally further comprises a peptide sequence consisting of hydrophilic amino acids, and wherein the peptide having 4 linked epitopes has any one of features selected from the following features (1) to (3):
 (1) the peptide comprises PEP2 at the C terminus (except for peptides comprising PEP7 and PEP8 at the N terminus successively disposed in such order from the N terminus via a linker);
 (2) the peptide comprises PEP4 at the C terminus; and
 (3) the peptide comprises PEP10 at the C terminus.

The present invention further relates to the following aspects.

Use of the peptide having 4 linked epitopes described above for enhancing the antitumor effect of an immune checkpoint modulator.

Use of the peptide having 4 linked epitopes described above for producing an antitumor effect enhancer for an immune checkpoint modulator.

A product comprising the peptide having 4 linked epitopes described above and an immune checkpoint modulator as a combined formulation, wherein the peptide having 4 linked epitopes and the immune checkpoint modulator are used simultaneously, sequentially, or separately at intervals in preventing and/or treating tumor.

This description includes part or all of the content as disclosed in Japanese Patent Application No. 2018-124894, based on which the present application claims the priority.

Advantageous Effects of Invention

The antitumor agent of the present invention enables cancer treatment that has a high antitumor effect (particularly, tumor reduction effect and/or tumor growth delaying effect (life prolongation effect)) while suppressing the development of adverse reactions. As a result, the antitumor agent of the present invention brings about long-term survival of cancer patients.

DESCRIPTION OF EMBODIMENTS

Figure 1:
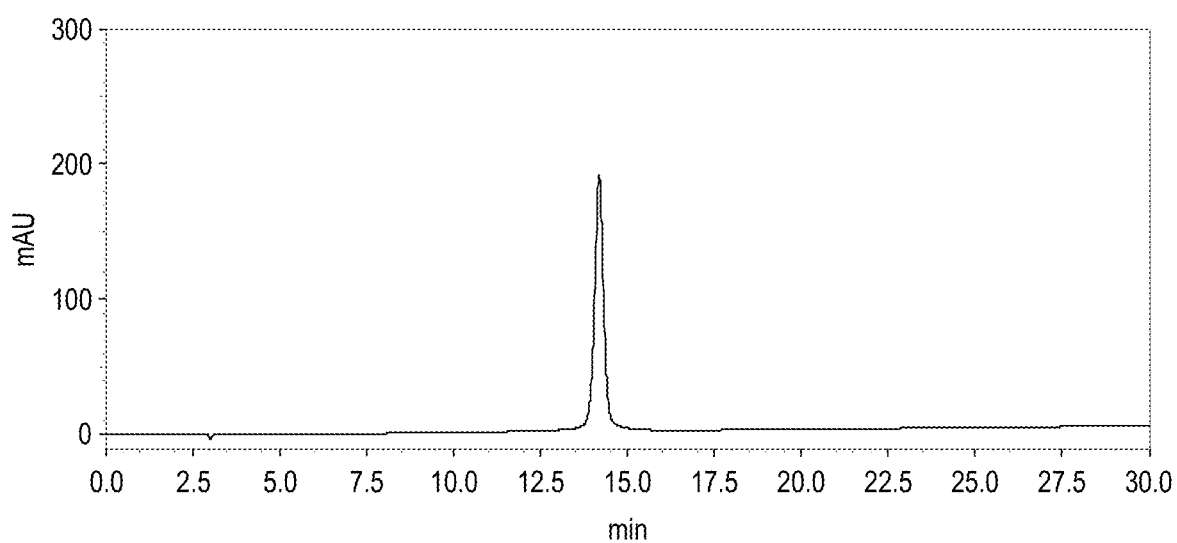
FIG. 1 shows an HPLC chromatogram of peptide TPV07 having 4 linked CTL epitopes.
Figure 2:
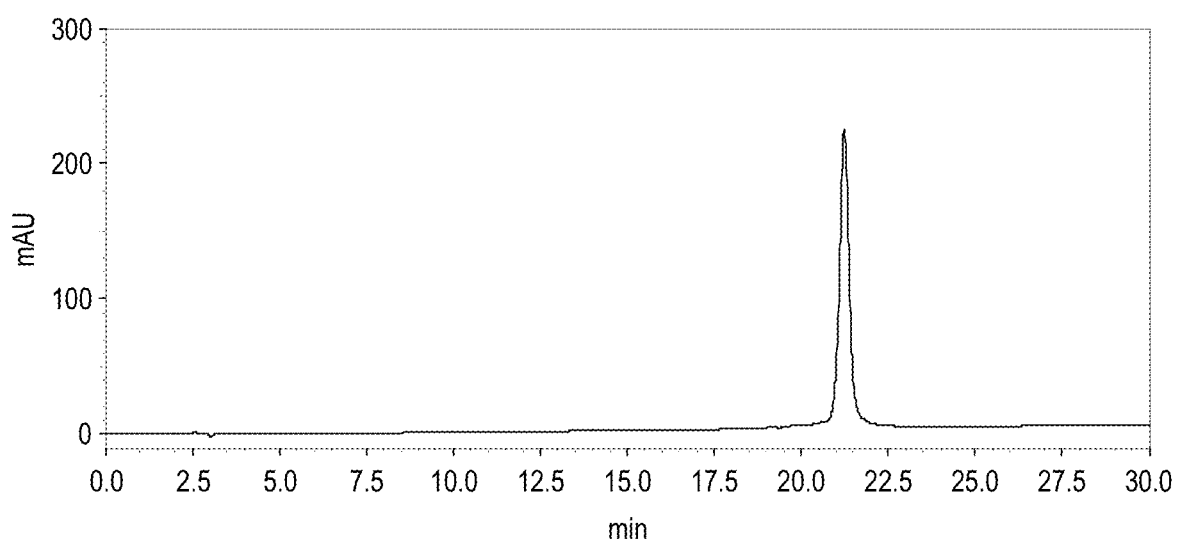
FIG. 2 shows an HPLC chromatogram of peptide TPV08 having 4 linked CTL epitopes.
Figure 3:
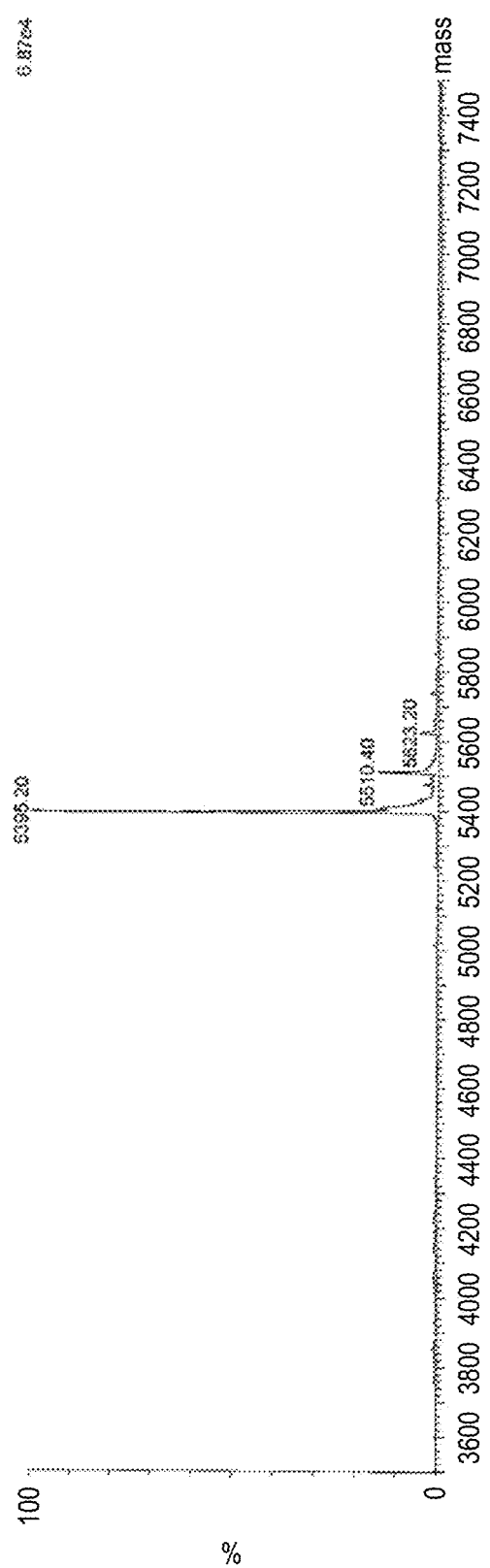
FIG. 3 shows a mass spectrum of peptide TPV07 having 4 linked CTL epitopes.
Figure 4:
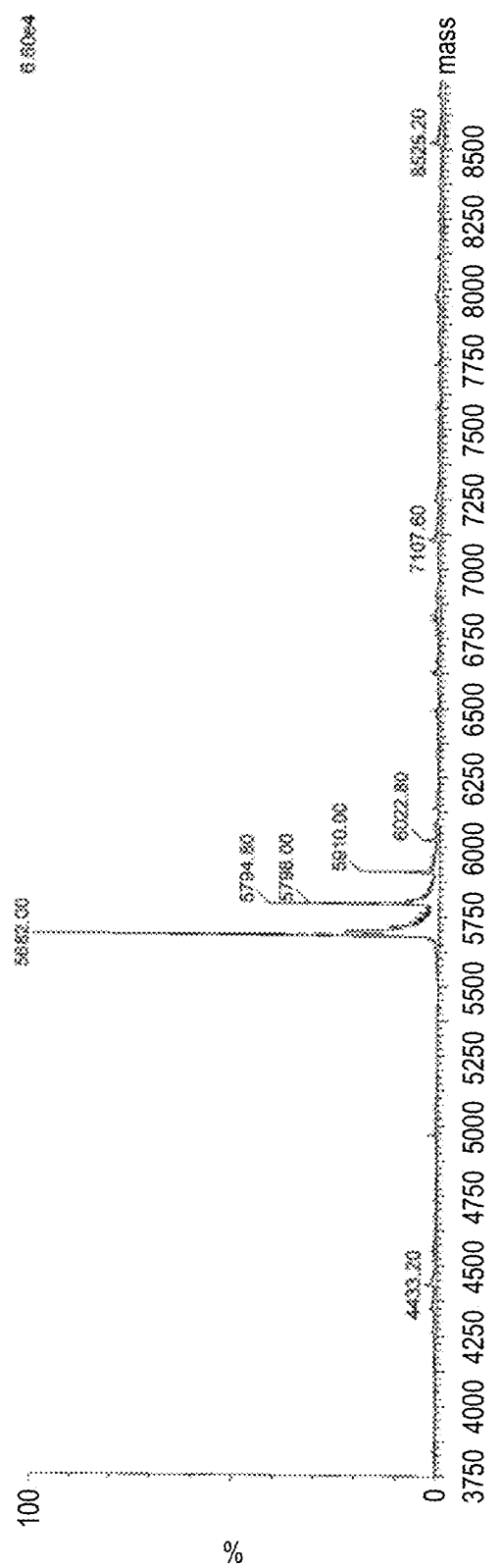
FIG. 4 shows a mass spectrum of peptide TPV08 having 4 linked CTL epitopes.

The present invention relates to an antitumor agent, an antitumor effect enhancer and a kit formulation, and use of these agents, a tumor treatment method, and a method for enhancing an antitumor effect, wherein a peptide having 4 linked epitopes and an immune checkpoint modulator (e.g., an anti-PD-1 antibody and an anti-PD-L1 antibody) are administered in combination.

In the present invention, the peptide having 4 linked CTL epitopes (herein, also referred to as a peptide having 4 linked epitopes) means a single molecule in which 4 peptides selected from among CTL epitope peptides derived from the same and/or different tumor antigen molecules are linearly linked via linkers.

The following CTL epitope peptides derived from tumor antigen molecules are known:

KLVERLGAA (SEQ ID NO: 1; designated herein as
"PEP1"; e.g., International Publication No. WO
2001/011044);

ASLDSDPWV (SEQ ID NO: 2; designated herein as
"PEP2"; e.g., International Publication No. WO
2002/010369);

ALVEFEDVL (SEQ ID NO: 3; designated herein as
"PEP3"; e.g., International Publication No. WO
2002/010369);

LLQAEAPRL (SEQ ID NO: 4; designated herein as
"PEP4"; e.g., International Publication No. WO
2000/12701);

DYSARWNEI (SEQ ID NO: 5; designated herein as
"PEP5"; e.g., JP Patent Publication (Kokai) No.
11-318455 A (1999));

VYDYNCHVDL (SEQ ID NO: 6; designated herein as
"PEP6"; e.g., International Publication No. WO
2000/12701);

LYAWEPSFL (SEQ ID NO: 7; designated herein as
"PEP7"; e.g., JP Patent Publication (Kokai) No.
2003-000270 A);

DYLRSVLEDF (SEQ ID NO: 8; designated herein as
"PEP8"; e.g., International Publication No. WO
2001/011044);

QIRPIFSNR (SEQ ID NO: 9; designated herein as
"PEP9"; e.g., International Publication No. WO
2008/007711);

ILEQSGEWWK (SEQ ID NO: 10; designated herein as
"PEP10"; e.g., International Publication No. WO
2009/022652);

VIQNLERGYR (SEQ ID NO: 11; designated herein as
"PEP11"; e.g., International Publication No. WO
2009/022652);

KLKHYGPGWV (SEQ ID NO: 12; designated herein as
"PEP12"; e.g., International Publication No. WO
1999/067288);

RLQEWCSVI (SEQ ID NO: 13; designated herein as
"PEP13"; e.g., International Publication No. WO
2002/010369);

ILGELREKV (SEQ ID NO: 14; designated herein as
"PEP14"; e.g., International Publication No. WO
2002/010369);

DYVREHKDNI (SEQ ID NO: 15; designated herein as
"PEP15"; e.g., International Publication No. WO
2005/071075);

HYTNASDGL (SEQ ID NO: 16; designated herein as
"PEP16"; e.g., International Publication No. WO
2001/011044);

NYSVRYRPGL (SEQ ID NO: 17; designated herein as
"PEP17"; e.g., JP Patent Publication (Kokai) No.
2003-000270 A);

RYLTQETNKV (SEQ ID NO: 18; designated herein as
"PEP18"; e.g., International Publication No. WO
2005/116056).

Table 1 below shows information on proteins from which CTL epitope peptides PEP1 to PEP18 are derived. These proteins have been reported to be highly expressed in tumor tissues.

TABLE 1

| Peptide | Origin | Amino acid sequence | SEQ ID NO |
|---|---|---|---|
| PEP1 | Lck-246 | KLVERLGAA | SEQ ID NO: 1 |
| PEP2 | WHSC2-103 | ASLDSDPWV | SEQ ID NO: 2 |
| PEP3 | HNRPL-140 | ALVEFEDVL | SEQ ID NO: 3 |
| PEP4 | SART3-302 | LLQAEAPRL | SEQ ID NO: 4 |
| PEP5 | SART2-93 | DYSARWNEI | SEQ ID NO: 5 |
| PEP6 | SART3-109 | VYDYNCHVDL | SEQ ID NO: 6 |
| PEP7 | MRP3-503 | LYAWEPSFL | SEQ ID NO: 7 |
| PEP8 | Lck-488 | DYLRSVLEDF | SEQ ID NO: 8 |
| PEP9 | SART3-734 | QIRFIFSNR | SEQ ID NO: 9 |
| PEP10 | Lck-80 | ILEQSGEWWK | SEQ ID NO: 10 |
| PEP11 | Lck-449 | VIQNLERGYR | SEQ ID NO: 11 |
| PEP12 | CypB-129 | KLKHYGPGWV | SEQ ID NO: 12 |
| PEP13 | UBE2V-43 | RLOEWCSVI | SEQ ID NO: 13 |
| PEP14 | WHSC2-141 | ILGELREKV | SEQ ID NO: 14 |
| PEP15 | EGFR-800 | DYVREHKDNI | SEQ ID NO: 15 |
| PEP16 | Lck-208 | HYTNASDGL | SEQ ID NO: 16 |
| PEP17 | MRP3-1293 | NYSVRYRPGL | SEQ ID NO: 17 |
| PEP18 | PTHrP-102 | RYLTQETNKV | SEQ ID NO: 18 |

The peptide having 4 linked CTL epitopes according to the present invention is a peptide in which 4 types of CTL epitope peptides selected from among particular 13 types of the CTL epitope peptides (the peptide as shown in SEQ ID NO: 1 (PEP1), the peptide as shown in SEQ ID NO: 2 (PEP2), the peptide as shown in SEQ ID NO: 4 (PEP4), the peptide as shown in SEQ ID NO: 5 (PEP5), the peptide as shown in SEQ ID NO: 6 (PEP6), the peptide as shown in SEQ ID NO: 7 (PEP7), the peptide as shown in SEQ ID NO: 8 (PEP8), the peptide as shown in SEQ ID NO: 9 (PEP9), the peptide as shown in SEQ ID NO: 10 (PEP10), the peptide as shown in SEQ ID NO: 13 (PEP13), the peptide as shown in SEQ ID NO: 15 (PEP15), the peptide as shown in SEQ ID NO: 17 (PEP17) and the peptide as shown in SEQ ID NO: 18 (PEP18)) are linearly linked via linkers, and which can induce and/or activate three or more CTLs specific for each CTL epitope peptide. Even if CTL epitope peptide specific induction is not directly evaluated, the occurrence of epitope peptide specific CTL induction can be determined by cleavage experiment with immunoproteasomes (International Publication No. WO 2015/060235, etc.).

The peptide having 4 linked epitopes according to the present invention is a peptide in which
the peptide as shown in SEQ ID NO: 5 (PEP5), and
3 peptides selected from the group consisting of the peptide as shown in SEQ ID NO: 1 (PEP1), the peptide as shown in SEQ ID NO: 2 (PEP2), the peptide as shown in SEQ ID NO: 4 (PEP4), the peptide as shown in SEQ ID NO: 6 (PEP6), the peptide as shown in SEQ ID NO: 7 (PEP7), the peptide as shown in SEQ ID NO: 8 (PEP8), the peptide as shown in SEQ ID NO: 9 (PEP9), the peptide as shown in SEQ ID NO: 10 (PEP10), the peptide as shown in SEQ ID NO: 13 (PEP13), the peptide as shown in SEQ ID NO: 15 (PEP15), the peptide as shown in SEQ ID NO: 17 (PEP17) and the peptide as shown in SEQ ID NO: 18 (PEP18) are linked via linkers.

In the present invention, a peptide having an amino acid sequence having substitution, insertion, deletion, and/or addition of one or several amino acids in each amino acid sequence of PEP1, PEP2, PEP4, PEP5, PEP6, PEP7, PEP8, PEP9, PEP10, PEP13, PEP15, PEP17, or PEP18 and having the ability of inducing CTL and/or the ability of inducting immunoglobulin production equivalent to or higher than those of the original peptide can be used as a "CTL epitope peptide." The term "several" used herein refers to 2 or 3, and preferably 2. An example of such peptide is a peptide obtained by substitution of amino acids with amino acids having properties similar to those of the original amino acids (i.e., a peptide obtained by conservative amino acid substitution).

Whether or not the peptide has "the ability of inducing CTL and/or the ability of inducting immunoglobulin production equivalent to or higher than those of the original peptide" can be evaluated in accordance with a method described in, for example, International Publication No. WO 2015/060235. In the case of evaluating the ability of inducing CTL by use of the method, the number of IFN-γ producing cells in wells supplemented with cells derived from a mouse given in advance a test peptide having an amino acid sequence having substitution, insertion, deletion, and/or addition of one or several amino acids, antigen presenting cells derived from a syngeneic mouse and the test peptide are used as an index, and the peptide can be confirmed to have the ability of inducing CTL equivalent to or higher than that of the original peptide when results of determining the obtained Δ value (positive ($10 \leq \Delta < 100$), moderately positive ($100 \leq \Delta < 200$), strongly positive ($200 \leq \Delta$)) are equivalent or higher. In this case, the equivalent ability is determined when the original peptide is "positive" and the peptide having an amino acid sequence having substitution, insertion, deletion, and/or addition of one or several amino acids is also "positive". As for the ability of inducing immunoglobulin production, CTL epitope specific IgG antibody titer in serum of a mouse given a test peptide is used as an index, and the peptide can be confirmed to have the ability of inducting immunoglobulin production equivalent to or higher than that of the original peptide when results of measured increase (fold) in the obtained IgG antibody titer ($2<fold<10$, $10 \leq fold <100$, $100 \leq fold$) are equivalent or higher. In this case, the equivalent ability is determined when the measurement results about the original peptide fall within the range of "$2<fold<10$" and the measurement results about the peptide having an amino acid sequence having substitution, insertion, deletion, and/or addition of one or several amino acids also fall within the range of "$2<fold<10$".

In the present invention, any linker can be used, provided that it is cleaved upon administration of a peptide having 4 linked CTL epitopes to an organism, and the linked CTL epitope peptides can be separated from each other. Examples thereof include an ester bond, an ether bond, an amide bond, a sugar chain linker, a polyethylene glycol linker, and an amino acid linker. Examples of amino acid sequences used as amino acid linkers include arginine dimer (RR), arginine trimer (RRR), arginine tetramer (RRRR), lysine dimer (KK), lysine trimer (KKK), lysine tetramer (KKKK), glycine dimer (GG), glycine trimer (GGG), glycine tetramer (GGGG), glycine pentamer (GGGGG), glycine hexamer (GGGGGG), alanine-alanine-tyrosine (AAY), isoleucine-leucine-alanine (ILA), and arginine-valine-lysine-arginine (RVKR), with arginine dimer (RR) or arginine trimer (RRR) being preferable and arginine dimer (RR) being more preferable. Linkers for use in peptides having linked epitopes are known in the art and can be appropriately selected for use by those skilled in the art.

In the peptide having 4 linked epitopes according to the present invention, CTL epitope peptides to be selected and the arrangements thereof can be determined by administering a peptide having 4 linked epitopes obtained by synthesizing it in given combinations and in a given order of epitopes to transgenic mice expressing human HLA-A, and evaluating the occurrence of CTL epitope peptide specific CTL induction in vivo. The occurrence of CTL epitope peptide specific CTL induction in vivo can be evaluated in accordance with a method described in, for example, International Publication No. WO 2015/060235. The CTL epitope peptides to be selected and the arrangements thereof can be determined, by use of the method, such that CTL epitope peptide specific CTL induction is found for at least 3 or more, preferably 4 CTL epitope peptides.

The peptide having 4 linked epitopes according to the present invention preferably has any one of features selected from the following features (1) to (3):
(1) the peptide comprises PEP2 at the C terminus (except for peptides comprising PEP7 and PEP8 at the N terminus successively disposed in such order from the N terminus via a linker);
(2) the peptide comprises PEP4 at the C terminus; and
(3) the peptide comprises PEP10 at the C terminus.

Thus, preferably, in the peptide having 4 linked epitopes according to the present invention,
the peptide as shown in SEQ ID NO: 5 (PEP5), and
3 peptides selected from the group consisting of the peptide as shown in SEQ ID NO: 1 (PEP1), the peptide as shown in SEQ ID NO: 2 (PEP2), the peptide as shown in SEQ ID NO: 4 (PEP4), the peptide as shown in SEQ ID NO: 6 (PEP6), the peptide as shown in SEQ ID NO: 7 (PEP7), the peptide as shown in SEQ ID NO: 8 (PEP8), the peptide as shown in SEQ ID NO: 9 (PEP9), the peptide as shown in SEQ ID NO: 10 (PEP10), the peptide as shown in SEQ ID NO: 13 (PEP13), the peptide as shown in SEQ ID NO: 15 (PEP15), the peptide as shown in SEQ ID NO: 17 (PEP17) and the peptide as shown in SEQ ID NO: 18 (PEP18) are linked via linkers, and the peptide having 4 linked epitopes has any one of features selected from the following features (1) to (3):
(1) the peptide comprises PEP2 at the C terminus (except for peptides comprising PEP7 and PEP8 at the N terminus successively disposed in such order from the N terminus via a linker);
(2) the peptide comprises PEP4 at the C terminus; and
(3) the peptide comprises PEP10 at the C terminus.

More preferably, the peptide having 4 linked epitopes according to the present invention comprises
- the peptide as shown in SEQ ID NO: 5 (PEP5), the peptide as shown in SEQ ID NO: 6 (PEP6) and the peptide as shown in SEQ ID NO: 9 (PEP9), and
- one peptide selected from the group consisting of the peptide as shown in SEQ ID NO: 2 (PEP2), the peptide as shown in SEQ ID NO: 4 (PEP4) and the peptide as shown in SEQ ID NO: 10 (PEP10), linked via linkers, and comprises PEP2, PEP4, or PEP10 at the C terminus.

More preferably, the peptide having 4 linked epitopes according to the present invention is a peptide consisting of a sequence selected from the following sequences:
PEP5-(L)-PEP6-(L)-PEP9-(L)-PEP4;
PEP9-(L)-PEP5-(L)-PEP6-(L)-PEP4;
PEP6-(L)-PEP5-(L)-PEP9-(L)-PEP4;
PEP6-(L)-PEP9-(L)-PEP5-(L)-PEP4;
PEP9-(L)-PEP6-(L)-PEP5-(L)-PEP4;
PEP5-(L)-PEP9-(L)-PEP6-(L)-PEP4;
PEP5-(L)-PEP9-(L)-PEP6-(L)-PEP2; and
PEP5-(L)-PEP9-(L)-PEP6-(L)-PEP10,
wherein "(L)" represents a linker.

More preferably, the peptide having 4 linked epitopes according to the present invention is a peptide consisting of a sequence selected from the following sequences:
PEP5-(L)-PEP9-(L)-PEP6-(L)-PEP4;
PEP5-(L)-PEP9-(L)-PEP6-(L)-PEP2; and
PEP5-(L)-PEP9-(L)-PEP6-(L)-PEP10,
wherein "(L)" represents a linker.

More preferably, the peptide having 4 linked epitopes according to the present invention is a peptide having an arginine dimer as the linker and a sequence selected from the following sequences:
PEP5-RR-PEP9-RR-PEP6-RR-PEP4 (SEQ ID NO: 24; designated herein as TPV06);
PEP5-RR-PEP9-RR-PEP6-RR-PEP2 (SEQ ID NO: 25; designated herein as TPV07); and
PEP5-RR-PEP9-RR-PEP6-RR-PEP10 (SEQ ID NO: 26; designated herein as TPV08).

More preferably, the peptide having 4 linked epitopes according to the present invention is peptide TPV06 as shown in SEQ ID NO: 24.

In one embodiment of the present invention, the peptide having 4 linked epitopes is preferably a peptide having a sequence selected from SEQ ID NOs: 19 to 28 shown in Table 2 below.

TABLE 2

| Peptide | Amino acid sequence | SEQ ID NO |
|---------|---------------------|-----------|
| TPV01 | PEP5-RR-PEP6-RR-PEP9-RR-PEP4 | SEQ ID NO: 19 |
| TPV02 | PEP9-RR-PEP5-RR-PEP6-RR-PEP4 | SEQ ID NO: 20 |
| TPV03 | PEP6-RR-PEP5-RR-PEP9-RR-PEP4 | SEQ ID NO: 21 |
| TPV04 | PEP6-RR-PEP9-RR-PEP5-RR-PEP4 | SEQ ID NO: 22 |
| TPV05 | PEP9-RR-PEP6-RR-PEP5-RR-PEP4 | SEQ ID NO: 23 |
| TPV06 | PEP5-RR-PEP9-RR-PEP6-RR-PEP4 | SEQ ID NO: 24 |
| TPV07 | PEP5-RR-PEP9-RR-PEP6-RR-PEP2 | SEQ ID NO: 25 |
| TPV08 | PEP5-RR-PEP9-RR-PEP6-RR-PEP10 | SEQ ID NO: 26 |
| TPV09 | RRR-PEP5-RR-PEP9-RR-PEP6-RR-PEP4 | SEQ ID NO: 27 |
| TPV10 | RRRR-PEP5-RR-PEP9-RR-PEP6-RR-PEP4 | SEQ ID NO: 28 |

More preferably, the peptide having 4 linked epitopes is any of the following peptides:

TPV01; (SEQ ID NO: 19)
TPV02; (SEQ ID NO: 20)
TPV03; (SEQ ID NO: 21)
TPV04; (SEQ ID NO: 22)
TPV05; and (SEQ ID NO: 23)
TPV06 (SEQ ID NO: 24)

selected from Table 2 described above.

In the present invention, 2 or more peptides having 4 linked epitopes may be used. For example, 2, 3, 4 or more peptides having 4 linked epitopes may be used separately or as a mixture, and 3 peptides having 4 linked epitopes are preferably used as a mixture. In the case of using 2 or more peptides having 4 linked epitopes, one or more of the peptides may be the peptide having 4 linked epitopes according to the present invention, or may be a peptide having 4 linked epitopes as described in, for example, International Publication No. WO 2015/060235, as long as at least one peptide having 4 linked epitopes according to the present invention is included. It is preferable to use the peptide as shown in SEQ ID NO: 24 and one or more peptides having 4 linked CTL epitopes described in International Publication No. WO 2015/060235. It is more preferable to use the peptide as shown in SEQ ID NO: 24 and 2 peptides having 4 linked epitopes described in International Publication No. WO 2015/060235. It is still more preferable to use 3 peptides, i.e., the peptide as shown in SEQ ID NO: 24, the peptide as shown in SEQ ID NO: 44 (TPV011: PEP15-RR-PEP18-RR-PEP1-RR-PEP10) and the peptide as shown in SEQ ID NO: 45 (TPV012: RRRR-PEP7-RR-PEP13-RR-PEP8-RR-PEP2), as a mixture.

The peptide having 4 linked CTL epitopes according to the present invention can further has a peptide sequence consisting of hydrophilic amino acids. Such peptide sequence can be added to the N terminus and/or the C terminus of the peptide having 4 linked CTL epitopes, and it is preferably added to the N terminus. Such peptide sequence consists of 1 to 15, preferably 2 to 10, and more preferably 3 to 5 hydrophilic amino acids selected from the group consisting of arginine, histidine, lysine, threonine, tyrosine, serine, asparagine, glutamine, aspartic acid, and glutamic acid. For example, arginine trimer (RRR) or arginine tetramer (RRRR) can be used as such a peptide sequence. Examples of peptides having 4 linked CTL epitopes comprising such peptide sequences added thereto include RRR-TPV06, RRRR-TPV06, TPV06-RRR, TPV06-RRRR, RRR-TPV07, RRRR-TPV07, TPV07-RRR, TPV07-RRRR, RRR-TPV08, RRRR-TPV08, TPV08-RRR, TPV08-RRRR, KKK-TPV06, KKKK-TPV06, TPV06-KKK, TPV06-KKKK, KKK-TPV07, KKKK-TPV07, TPV07-KKK, TPV07-KKKK, KKK-TPV08, KKKK-TPV08, TPV08-KKK, TPV08-KKKK, HHH-TPV06, HHHH-TPV06, TPV06-HHH, TPV06-HHHH, HHH-TPV07, HHHH-TPV07, TPV07-HHH, TPV07-HHHH, HHH-TPV08, HHHH-TPV08, TPV08-HHH, TPV08-HHHH, RRKK-TPV06, RKRK-TPV06, RHRH-TPV06, RRHH-TPV06, KKHH-TPV06, and KHKH-TPV06, with RRR-TPV06, RRRR-TPV06, RRR-TPV07, RRRR-TPV07, RRR-TPV08, RRRR-TPV08, KKK-TPV06, KKKK-TPV06, KKK-TPV07, KKKK-TPV07, KKK-TPV08, KKKK-TPV08, HHH-TPV06, HHHH-TPV06, HHH-TPV07, HHHH-TPV07, HHH-TPV08, HHHH-TPV08, RRKK-TPV06, RKRK-TPV06, RHRH-TPV06, RRHH-TPV06, KKHH-TPV06, and KHKH-TPV06 being preferable, RRR-TPV06 (TPV09), RRRR-TPV06 (TPV10), RRR-TPV07, RRRR-TPV07, RRR-TPV08, and RRRR-TPV08 being more preferable, and RRR-TPV06 (TPV09) and RRRR-TPV06 (TPV10) being most preferable.

A peptide comprising such peptide sequence consisting of hydrophilic amino acids is known to have improved solubility in an aqueous solvent (Peptides: 38, 302-311 (2012); JP Patent Publication (Kokai) No. 2006-188507 A). With the addition of such peptide sequence to the peptide having 4 linked CTL epitopes according to the present invention, the solubility of the peptide having 4 linked CTL epitopes in an aqueous solvent can be improved.

The "peptide having 4 linked epitopes optionally further comprising a peptide sequence consisting of hydrophilic amino acids" according to the present invention is preferably a peptide having 4 linked CTL epitopes optionally comprising a peptide sequence consisting of hydrophilic amino acids at the N terminus, more preferably a peptide having 4 linked CTL epitopes optionally comprising a peptide sequence consisting of 3 to 5 hydrophilic amino acids selected from the group consisting of arginine, histidine and lysine at the N terminus, more preferably a peptide having 4 linked CTL epitopes optionally comprising an arginine trimer (RRR) or an arginine tetramer (RRRR) at the N terminus, and still more preferably a peptide having 4 linked CTL epitopes not comprising a peptide sequence consisting of hydrophilic amino acids.

The peptide having 4 linked CTL epitopes according to the present invention can be synthesized in accordance with a method described in, for example, International Publication No. WO 2015/060235.

The immune checkpoint modulator according to the present invention acts on an immune checkpoint molecule and has an effect of inducing in vivo antitumor immune responses in cancer patients and preventing tumor immune escape.

Thus, a substance targeting an immune checkpoint molecule can be used as the immune checkpoint modulator. Examples of the immune checkpoint molecule include molecules of the B7 family (B7-1, B7-2, PD-L1, PD-L2, etc.), the CD28 family (CTLA-4, PD-1, etc.), the TNF superfamily (4-1BBL, OX40L, etc.), and the TNF receptor superfamily (4-1BB, OX40, etc.), which are broadly classified into costimulatory molecules having stimulatory action and coinhibitory molecules having suppressive action.

Examples of the immune checkpoint modulator that may be suitably used in the present invention include substances promoting the functions of costimulatory molecules and substances suppressing the functions of coinhibitory molecules. More specifically, examples of the immune checkpoint modulator include a PD-1 pathway antagonist, an ICOS pathway agonist, a CTLA-4 pathway antagonist, a CD28 pathway agonist, a BTLA pathway antagonist, and a 4-1BB pathway agonist, etc.

In the present invention, the immune checkpoint modulator is preferably at least one selected from the group consisting of a PD-1 pathway antagonist, an ICOS pathway agonist, a CTLA-4 pathway antagonist and a CD28 pathway agonist, more preferably at least one selected from the group consisting of a PD-1 pathway antagonist, a CTLA-4 pathway antagonist and a CD28 pathway agonist, more preferably at least one selected from the group consisting of a PD-1 pathway antagonist and a CTLA-4 pathway antagonist, and still more preferably a PD-1 pathway antagonist from the viewpoint of suppression of adverse reactions.

The PD-1 pathway antagonist inhibits immunosuppressive signals induced by PD-1 expressed on T cells or its ligand PD-L1 or PD-L2. Examples thereof include an anti-PD-1 antibody, an anti-PD-L1 antibody, an anti-PD-L2 antibody, a PD-1 extracellular domain, a PD-L1 extracellular domain, a PD-L2 extracellular domain, PD-1-Ig (fusion protein of a PD-1 extracellular domain and an immunoglobulin (Ig) FC region), PD-L1-Ig, PD-L2-Ig, PD-1 siRNA, PD-L1 siRNA, and PD-L2 siRNA. The PD-1 pathway antagonist is preferably an anti-PD-1 antibody, an anti-PD-L1 antibody, or an anti-PD-L2 antibody, more preferably an anti-PD-1 antibody or an anti-PD-L1 antibody. Among them, an anti-PD-1 antibody is particularly preferable.

The CTLA-4 pathway antagonist inhibits immunosuppressive signals induced by CTLA-4 expressed on T cells or its ligand B7-1 (CD80) or B7-2 (CD86). Examples thereof include an anti-CTLA-4 antibody, a CTLA-4 extracellular domain, CTLA-4-Ig, an anti-B7-1 (CD80) antibody, an anti-B7-2 (CD86) antibody, and CTLA-4 siRNA. The CTLA-4 pathway antagonist is preferably an anti-CTLA-4 antibody, a CTLA-4 extracellular domain, CTLA-4-Ig, an anti-B7-1 (CD80) antibody, or an anti-B7-2 (CD86) antibody, more preferably an anti-CTLA-4 antibody or CTLA-4-Ig. Among them, an anti-CTLA-4 antibody is particularly preferable.

Examples of these antibodies include immunoglobulins (IgA, IgD, IgE, IgG, IgM, IgY, etc.), Fab fragments, F(ab')$_2$ fragments, single-chain variable fragments (scFv), single-domain antibodies, and diabody (Nat. Rev. Immunol., 6: 343-357, 2006). Examples thereof include monoclonal or polyclonal antibodies including human antibodies, humanized antibodies, chimeric antibodies, mouse antibodies, llama antibodies, and chicken antibodies.

A humanized IgG monoclonal antibody or a human IgG monoclonal antibody is preferable.

Examples of the anti-PD-1 antibody according to the present invention include nivolumab, pembrolizumab, cemiplimab and spartalizumab, with nivolumab or pembrolizumab being preferable.

Examples of the anti-PD-L1 antibody according to the present invention include atezolizumab, durvalumab, avelumab, and the like, with atezolizumab, durvalumab or avelumab being preferable.

Examples of the anti-CTLA-4 antibody according to the present invention include ipilimumab, tremelimumab, and the like, with ipilimumab being preferable.

Examples of the CTLA-4-Ig according to the present invention include abatacept and the like, with abatacept being preferable.

These antibodies can be produced by commonly known antibody preparation methods.

The anti-PD-1 antibody is already sold or will be sold as nivolumab or pembrolizumab; the anti-PD-L1 antibody is already sold or will be sold as atezolizumab, durvalumab or avelumab; the anti-CTLA-4 antibody is already sold or will be sold as ipilimumab or tremelimumab; and CTLA-4-Ig is already sold or will be sold as abatacept, any of which can also be used.

In the present invention, in the case of using 2 or more immune checkpoint modulators, for example, an anti-PD-1 antibody and/or an anti-CTLA-4 antibody may be used in combination, or a bispecific antibody capable of binding to both PD-1 and CTLA-4 may be used. Examples of the bispecific antibody include XmAb20717 (PD-1×CTLA-4).

The recommended dose of the peptide having 4 linked epitopes used in the present invention for humans is in the range of 3 to 9 mg/body/day per each peptide having 4 linked epitopes for monotherapy. In the present invention, the amount of the peptide having 4 linked epitopes administered per day on the day of administration is preferably 50 to 200%, more preferably 80 to 120%, particularly preferably 100%, of the recommended dose of the peptide having 4 linked epitopes for monotherapy, from the viewpoint of an effect of enhancing the antitumor effect of the immune checkpoint modulator by the peptide having 4 linked epitopes.

Thus, when the recommended dose for humans is 3 mg/body/day, the amount of the peptide having 4 linked epitopes administered is preferably 1.5 to 6 mg/body/day, more preferably 2.4 to 3.6 mg/body/day, and particularly preferably 3 mg/body/day, per peptide having 4 linked epitopes. When the recommended dose for humans is 9 mg/body/day, the amount of the peptide having 4 linked epitopes administered is preferably 4.5 to 18 mg/body/day, more preferably 7.2 to 10.8 mg/body/day, and particularly preferably 9 mg/body/day, per peptide having 4 linked epitopes.

In the present invention, the amount of the immune checkpoint modulator administered per day on the day of administration is preferably 50 to 100%, and more preferably 100%, of the recommended dose of the immune checkpoint modulator when administered alone, from the viewpoint of an effect of enhancing the antitumor effect of the immune checkpoint modulator by the peptide having 4 linked epitopes.

Specifically, the recommended dose of nivolumab administered alone is 2 mg/kg (body weight) per dose or 3 mg/kg (body weight) per dose, which has been approved in Japan. Therefore, the amount of nivolumab administered per day on the day of administration according to the present invention is preferably 1 to 3 mg/kg (body weight) per dose, and more preferably 2 mg/kg (body weight) per dose or 3 mg/kg (body weight) per dose.

The recommended dose of pembrolizumab administered alone is 2 mg/kg (body weight) per dose or 200 mg per dose, which has been approved in Japan. Therefore, the amount of pembrolizumab administered per day on the day of administration according to the present invention is preferably 1 to 2 mg/kg (body weight) per dose or 100 to 200 mg per dose, and more preferably 2 mg/kg (body weight) per dose or 200 mg per dose.

The recommended dose of atezolizumab administered alone is 1200 mg per dose, which has been approved in Japan. Therefore, the amount of atezolizumab administered per day on the day of administration according to the present invention is preferably 600 to 1200 mg per dose, and more preferably 1200 mg per dose.

The recommended dose of avelumab or durvalumab administered alone is 10 mg/kg (body weight) per dose, which has been approved in the USA. Therefore, the amount of avelumab or durvalumab administered per day on the day of administration according to the present invention is preferably 5 to 10 mg/kg (body weight) per dose, and more preferably 10 mg/kg (body weight) per dose.

The recommended dose of ipilimumab administered alone is 3 mg/kg (body weight) per dose, which has been approved in Japan. Therefore, the amount of ipilimumab administered per day on the day of administration according to the present invention is preferably 1.5 to 3 mg/kg (body weight) per dose, and more preferably 3 mg/kg (body weight) per dose.

In the present invention, the "recommended dose" is a range of dose that have been determined by clinical trials, etc. and can be used safely without exhibiting severe adverse events, which may provide the maximum therapeutic effect. Specifically, examples thereof include a recommended dose approved and/or recommended by a public organization or institution such as Pharmaceuticals and Medical Devices Agency (PMDA), Food and Drug Administration (FDA), or European Medicines Agency (EMA), and described in a package insert, an interview form, a treatment guideline, or the like. The recommended dose approved by any of the public organizations PMDA, FDA and EMA is preferable.

The antitumor agent of the present invention can be administered in accordance with a schedule appropriately selected according to a type of cancer, stage, etc.

The peptide having 4 linked epitopes is preferably administered in accordance with a schedule with one cycle set to a total of 21 days involving 3 repetitive steps of administration once a week (once a day on days 1, 8 and 15). In the 3rd cycle or later, it is preferably administered in accordance with a schedule with one cycle set to a total of 21 days involving administration on day 1 and cessation of the drug for 20 days (administration every 3 weeks).

Nivolumab is preferably administered in accordance with a schedule of administration at 2-week or 3-week intervals.

Pembrolizumab, atezolizumab or ipilimumab is preferably administered in accordance with a schedule of administration at 3-week intervals.

Avelumab or durvalumab is preferably administered in accordance with a schedule of administration at 2-week intervals.

The number of administration of the antitumor agent of the present invention per day can be appropriately selected according to a type of cancer, stage, etc.

The peptide having 4 linked epitopes, nivolumab, pembrolizumab, atezolizumab, avelumab or ipilimumab is preferably administered once a day.

The peptide having 4 linked epitopes according to the present invention and the immune checkpoint modulator can be administered in an order appropriately selected according to a type of cancer, stage, etc., either of which may be administered first or both of which may be administered simultaneously. In the case of not simultaneously administering these agents, the agents can be administered at an appropriately selected interval as long as an effect of enhancing an antitumor effect is exerted. The interval is preferably 1 to 21 days, more preferably 1 to 14 days, and particularly preferably 1 to 7 days. The peptide having 4 linked epitopes according to the present invention and the immune checkpoint modulator are preferably administered in an order in which the peptide having 4 linked epitopes is administered first.

The tumor to be targeted in the present invention is not particularly limited as long as an effect of enhancing an antitumor effect is exerted. The tumor is preferably tumor on which the peptide having 4 linked epitopes exerts an antitumor effect, more preferably malignant tumor positive for Lck, WHSC2, SART2, SART3, MRP3, UBE2V, EGFR, or PTHrP, and more preferably SART2-positive malignant tumor.

Specific examples of the cancer to be targeted in the present invention include brain tumor, head and neck cancer, gastrointestinal cancer (esophageal cancer, gastric cancer, duodenal cancer, liver cancer, biliary tract cancer (gallbladder cancer, bile duct cancer, etc.), pancreatic cancer, small intestine cancer, large intestine cancer (colorectal cancer, colon cancer, rectal cancer, etc.), gastrointestinal stromal tumor, etc.), lung cancer (non-small cell lung cancer and small cell lung cancer), breast cancer, ovarian cancer, uterine cancer (cervical cancer, endometrical cancer, etc.), kidney cancer, urothelial cancer (bladder cancer, renal pelvis cancer, and ureter cancer), prostate cancer, skin cancer, and cancer of unknown primary origin. In this context, the cancer includes not only primary tumor but also a cancer metastasized to other organs (liver, etc.). Among them, head and neck cancer, gastrointestinal cancer, lung cancer, kidney cancer, urothelial cancer, and skin cancer are preferable, digestive system cancer, lung cancer, urothelial cancer, and skin cancer are more preferable, and lung cancer and urothelial cancer are particularly preferable, from the viewpoint of an antitumor effect. The antitumor agent of the present invention may be the one for use in postoperative adjuvant chemotherapy which is performed for preventing recurrence after surgical extirpation of tumor, or may be the one for use in preoperative adjuvant chemotherapy which is performed before surgical extirpation of tumor.

In the present invention, the peptide having 4 linked epitopes and the immune checkpoint modulator may be prepared in a plurality of formulations of the active ingredients or in the form of a single-agent formulation (e.g., formulation as a combination drug) on the basis of the dosage form of each active ingredient or the administration schedule. These formulations may be produced and distributed in one package suitable for use in combination, or may be produced and distributed in separate packages.

The dosage form of the antitumor agent of the present invention is not particularly limited and can be appropriately selected according to a therapeutic purpose. Specific examples thereof can include oral formulations (tablets, coated tablets, powders, granules, capsules, liquid formulations, etc.), injections, suppositories, patches, and ointments.

Examples of the dosage forms of the peptide having 4 linked epitopes, the anti-PD-1 antibody, the anti-PD-L1 antibody and the anti-CTLA-4 antibody include the dosage forms described above, with an injection being preferable.

The antitumor agent according to the present invention can be prepared by a commonly known method using a pharmaceutically acceptable carrier according to the dosage form both for the peptide having 4 linked epitopes and for the immune checkpoint modulator. Examples of such carriers can include various ones generally used in common drugs, for example, excipients, binders, disintegrators, lubricants, diluents, solubilizers, suspending agents, isotonizing agents, pH adjusters, buffers, stabilizers, colorants, flavoring agents, and odor correcting agents.

The present invention also relates to an antitumor effect enhancer for enhancing the antitumor effect of an immune checkpoint modulator on a cancer patient, comprising a peptide having 4 linked epitopes as an active ingredient. The antitumor effect enhancer has the dosage form of the antitumor agent described above.

The present invention also relates to an antitumor agent for treating a cancer patient given an immune checkpoint modulator, comprising a peptide having 4 linked epitopes. The antitumor agent has the dosage form described above.

The present invention also relates to an antitumor agent for treating a cancer patient given a peptide having 4 linked epitopes, comprising an immune checkpoint modulator. The antitumor agent has the dosage form described above.

The "treatment" includes postoperative adjuvant chemotherapy which is performed for preventing reoccurrence after surgical extirpation of tumor, and preoperative adjuvant chemotherapy which is performed beforehand for surgical extirpation of tumor.

The present invention also relates to an antitumor agent comprising a peptide having 4 linked epitopes, wherein the peptide having 4 linked epitopes is used in combination with an immune checkpoint modulator for a cancer patient. The antitumor agent has the dosage form described above.

The present invention also relates to an antitumor agent comprising an immune checkpoint modulator, wherein the immune checkpoint modulator is used in combination with a peptide having 4 linked epitopes for a cancer patient. The antitumor agent has the dosage form described above.

The present invention also relates to a kit formulation comprising an antitumor agent comprising a peptide having 4 linked epitopes, and an instruction for use stating that the peptide having 4 linked epitopes and an immune checkpoint modulator are administered in combination to a cancer patient.

In this context, the "instruction for use" describes the amounts of the agents to be administered and preferably recommended dose as described above, with or without legal binding. Specific examples thereof include package inserts and pamphlets. In the kit formulation comprising an instruction for use, the instruction for use may be printed and/or attached on the package of the kit formulation, or the instruction for use may be enclosed, together with the antitumor agent, in the package of the kit formulation.

Meanwhile, the group of the present inventor, et al. has established a technique of expressing an artificial chimeric gene of a human- or non-human-derived β2 microglobulin, HLA class I α1 and α2 regions, and a human- or non-human-derived MHC class I α3 region linked to each other in non-human animals, and successfully prepared a non-human animal expressing HLA class I (International Publication No. WO 2015/056774).

Use of the non-human animal described above enables reconstitution of human immune responses in non-human animals. Specifically, antigen presenting cells in the non human animal express HLA class I α1 and α2 regions and can therefore present an epitope peptide of a human tumor antigen capable of binding thereto.

The present inventor has further found that an effect of CTL induction by a peptide having 4 linked epitopes can be evaluated by coexpressing human HLA-A24 and an epitope peptide of a human tumor antigen derived from SART2. For example, tumor presenting an epitope peptide of a human tumor antigen derived from SART2 can be allowed to grow by coexpressing human HLA-A24 and the epitope peptide of a human tumor antigen derived from SART2 to cultured cells derived from mouse tumor, and transplanting the cultured cells to the non-human animal described above.

Specifically, the present invention provides a cell which have been introduced a polynucleotide encoding an epitope peptide of a human tumor antigen derived from SART2, and a polynucleotide encoding, particularly, α1 and α2 regions of human HLA-A24. In this context, the epitope peptide of a human tumor antigen derived from SART2 preferably comprises PEP5. Thus, a polynucleotide encoding PEP5 is preferably introduced to the cell.

The present inventor has successfully engrafted tumors coexpressing HLA-A24 and PEP5 in the non-human animal described above, and demonstrated that this system enables evaluation of the antitumor agent of the present invention, etc.

Accordingly, the present invention relates to a cell which have been introduced a polynucleotide encoding an epitope peptide of a human tumor antigen derived from SART2 and a polynucleotide encoding α1 and α2 regions of human HLA-A24 (hereinafter, also referred to as the "cell of the present invention").

SART2 is one of proteins reported to be highly expressed in tumor tissues, as described above. Examples of the epitope peptide of a human tumor antigen derived from SART2 which may be presented through binding to an HLA-A24 type HLA molecule in antigen presenting cells such as dendritic cells include PEP5 described above. The amino acid sequence of the peptide PEP5 is shown in SEQ ID NO: 5, and a polynucleotide sequence encoding the peptide PEP5 is shown in SEQ ID NO: 29.

The "polynucleotide encoding an epitope peptide of a human tumor antigen derived from SART2" used herein is preferably a polynucleotide selected from the following polynucleotides (a) to (e):
  (a) a polynucleotide encoding a polypeptide comprising the amino acid sequence as shown in SEQ ID NO: 5;
  (b) a polynucleotide encoding a polypeptide comprising an amino acid sequence having substitution, deletion, or addition of one or several amino acids in the amino acid sequence as shown in SEQ ID NO: 5;
  (c) a polynucleotide encoding a polypeptide comprising an amino acid sequence having 90% or higher identity to the amino acid sequence as shown in SEQ ID NO: 5;
  (d) a polynucleotide comprising the nucleotide sequence as shown in SEQ ID NO: 29; and
  (e) a polynucleotide comprising a nucleotide sequence having 90% or higher identity to the nucleotide sequence as shown in SEQ ID NO: 29;
more preferably a polynucleotide selected from the following polynucleotides (a) to (e):
  (a) a polynucleotide encoding a polypeptide comprising the amino acid sequence as shown in SEQ ID NO: 5;
  (b) a polynucleotide encoding a polypeptide comprising an amino acid sequence having substitution, deletion, or addition of one or several amino acids in the amino acid sequence as shown in SEQ ID NO: 5 (wherein the addition of amino acids is limited to addition to the N terminal side);
  (c) a polynucleotide encoding a polypeptide comprising an amino acid sequence having 90% or higher identity to the amino acid sequence as shown in SEQ ID NO: 5;
  (d) a polynucleotide comprising the nucleotide sequence as shown in SEQ ID NO: 29; and
  (e) a polynucleotide comprising a nucleotide sequence having 90% or higher identity to the nucleotide sequence as shown in SEQ ID NO: 29;
and more preferably a polynucleotide selected from the polynucleotides (a) and (d).

The "polypeptide comprising the amino acid sequence as shown in SEQ ID NO: 5" used herein may further comprise an added signal sequence. Preferably, the "polypeptide comprising the amino acid sequence as shown in SEQ ID NO: 5" is a polypeptide having a signal sequence of 10 to 30 amino acids, more preferably a signal sequence of 15 to 25 amino acids, added to the N terminal side of the amino acid sequence as shown in SEQ ID NO: 5, and is more preferably a polypeptide consisting of the amino acid sequence as shown in SEQ ID NO: 32.

Likewise, the "polypeptide comprising an amino acid sequence having substitution, deletion, or addition of one or several amino acids in the amino acid sequence as shown in SEQ ID NO: 5" used herein may further comprise an added signal sequence. Preferably, this polypeptide is a polypeptide having a signal sequence of 10 to 30 amino acids, more preferably a signal sequence of 15 to 25 amino acids, added to the N terminal side of the amino acid sequence having substitution, deletion, or addition of one or several amino acids in the amino acid sequence as shown in SEQ ID NO: 5, and is more preferably a polypeptide consisting of the amino acid sequence as shown in SEQ ID NO: 32.

Likewise, the "polypeptide comprising an amino acid sequence having 90% or higher identity to the amino acid sequence as shown in SEQ ID NO: 5" used herein may further comprise an added signal sequence. Preferably, this polypeptide is a polypeptide having a signal sequence of 10 to 30 amino acids, more preferably a signal sequence of 15 to 25 amino acids, added to the N terminal side of the amino acid sequence having 90% or higher identity to the amino acid sequence as shown in SEQ ID NO: 5, and is more preferably a polypeptide consisting of the amino acid sequence as shown in SEQ ID NO: 32.

Likewise, the "polynucleotide comprising the nucleotide sequence as shown in SEQ ID NO: 29" used herein may further comprise an added nucleotide sequence encoding a signal sequence. Preferably, this polynucleotide is a polynucleotide having 30 to 90 nucleotides encoding a signal sequence, more preferably 45 to 75 nucleotides encoding a signal sequence, added to the 5' terminal side of the nucleotide sequence as shown in SEQ ID NO: 29, and is more preferably a polynucleotide consisting of the nucleotide sequence as shown in SEQ ID NO: 33.

Likewise, the "polynucleotide comprising a nucleotide sequence having 90% or higher identity to the nucleotide sequence as shown in SEQ ID NO: 29" used herein may further comprise an added nucleotide sequence encoding a signal sequence. Preferably, this polynucleotide is a polynucleotide having 30 to 90 nucleotides encoding a signal sequence, more preferably 45 to 75 nucleotides encoding a signal sequence, added to the 5' terminal side of the nucleotide sequence having 90% or higher identity to the nucleotide sequence as shown in SEQ ID NO: 29, and is more preferably a polynucleotide consisting of the nucleotide sequence as shown in SEQ ID NO: 33.

In one aspect of the present invention, the "polynucleotide encoding an epitope peptide of a human tumor antigen derived from SART2" may preferably be a polynucleotide selected from the following polynucleotides (k) to (o):

(k) a polynucleotide encoding a polypeptide consisting of the amino acid sequence as shown in SEQ ID NO: 32;
(l) a polynucleotide encoding a polypeptide consisting of an amino acid sequence having substitution, deletion, or addition of one or several amino acids in the amino acid sequence as shown in SEQ ID NO: 32;
(m) a polynucleotide encoding a polypeptide consisting of an amino acid sequence having 90% or higher identity to the amino acid sequence as shown in SEQ ID NO: 32;
(n) a polynucleotide consisting of the nucleotide sequence as shown in SEQ ID NO: 33; and
(o) a polynucleotide consisting of a nucleotide sequence having 90% or higher identity to the nucleotide sequence as shown in SEQ ID NO: 33;
more preferably a polynucleotide selected from the following polynucleotides (k) to (o):
(k) a polynucleotide encoding a polypeptide consisting of the amino acid sequence as shown in SEQ ID NO: 32;
(l) a polynucleotide encoding a polypeptide consisting of an amino acid sequence having substitution, deletion, or addition of one or several amino acids in the amino acid sequence as shown in SEQ ID NO: 32 (wherein the addition of amino acids is limited to addition to the N terminal side);
(m) a polynucleotide encoding a polypeptide consisting of an amino acid sequence having 90% or higher identity to the amino acid sequence as shown in SEQ ID NO: 32;
(n) a polynucleotide consisting of the nucleotide sequence as shown in SEQ ID NO: 33; and
(o) a polynucleotide consisting of a nucleotide sequence having 90% or higher identity to the nucleotide sequence as shown in SEQ ID NO: 33;
and more preferably a polynucleotide selected from the polynucleotides (k) and (n).

Preferably, the "epitope peptide of a human tumor antigen derived from SART2" can be recognized by CTLs specific for the amino acid sequence as shown in SEQ ID NO: 5.

In this context, whether or not the epitope peptide "can be recognized by CTL specific for the amino acid sequence as shown in SEQ ID NO: 5" can be confirmed by, for example, $^{51}$Cr release assay, ELISA (e.g., measurement of IFN-γ) or ELISPOT assay (e.g., measurement of IFN-γ) using the cell of the present invention and CTLs specific for the amino acid sequence as shown in SEQ ID NO: 5.

The "polynucleotide encoding α1 and α2 regions of human HLA-A24" used herein may preferably be a polynucleotide selected from the following polynucleotides (f) to (j):

(f) a polynucleotide encoding a polypeptide comprising the amino acid sequence as shown in SEQ ID NO: 30;
(g) a polynucleotide encoding a polypeptide comprising an amino acid sequence having substitution, deletion, or addition of one or several amino acids in the amino acid sequence as shown in SEQ ID NO: 30;
(h) a polynucleotide encoding a polypeptide comprising an amino acid sequence having 90% or higher identity to the amino acid sequence as shown in SEQ ID NO: 30;
(i) a polynucleotide comprising the nucleotide sequence as shown in SEQ ID NO: 31; and
(j) a polynucleotide comprising a nucleotide sequence having 90% or higher identity to the nucleotide sequence as shown in SEQ ID NO: 31;
and more preferably a polynucleotide selected from the polynucleotides (f) and (i).

The "polypeptide comprising the amino acid sequence as shown in SEQ ID NO: 30" used herein may preferably be a polypeptide comprising a β2 microglobulin added to the N terminal side, and an MHC class I α3 region added to the C terminal side of the amino acid sequence as shown in SEQ ID NO: 30, and more preferably a polypeptide consisting of the amino acid sequence as shown in SEQ ID NO: 34.

The "polypeptide comprising an amino acid sequence having substitution, deletion, or addition of one or several amino acids in the amino acid sequence as shown in SEQ ID NO: 30" used herein may preferably be a polypeptide comprising a β2 microglobulin added to the N terminal side, and an MHC class I α3 region added to the C terminal side of the amino acid sequence having substitution, deletion, or addition of one or several amino acids in the amino acid sequence as shown in SEQ ID NO: 30, and more preferably a polypeptide consisting of the amino acid sequence as shown in SEQ ID NO: 34.

The "polypeptide comprising an amino acid sequence having 90% or higher identity to the amino acid sequence as shown in SEQ ID NO: 30" used herein may preferably be a polypeptide comprising a β2 microglobulin added to the N terminal side, and an MHC class I α3 region added to the C terminal side of the amino acid sequence having 90% or higher identity to the amino acid sequence as shown in SEQ ID NO: 30, and more preferably a polypeptide consisting of the amino acid sequence as shown in SEQ ID NO: 34.

The "polynucleotide comprising the nucleotide sequence as shown in SEQ ID NO: 31" used herein may preferably be a polynucleotide comprising a β2 microglobulin-encoding nucleotide sequence added to the 5' terminal side, and an MHC class I α3 region-encoding nucleotide sequence added to the 3' terminal side of the nucleotide sequence as shown in SEQ ID NO: 31, and more preferably a polynucleotide consisting of the nucleotide sequence as shown in SEQ ID NO: 35.

The "polynucleotide comprising a nucleotide sequence having 90% or higher identity to the nucleotide sequence as shown in SEQ ID NO: 31" used herein may preferably be a polynucleotide comprising a β2 microglobulin-encoding nucleotide sequence added to the 5' terminal side, and an MHC class I α3 region-encoding nucleotide sequence added to the 3' terminal side of the nucleotide sequence having 90% or higher identity to the nucleotide sequence as shown in SEQ ID NO: 31, and more preferably a polynucleotide consisting of the nucleotide sequence as shown in SEQ ID NO: 35.

The "β2 microglobulin" used herein refers to a protein constituting the β chain of an MHC class I molecule. The "β2 microglobulin" used herein may be derived from a human or any non-human animal (mouse, rat, hamster, guinea pig, rabbit, pig, bovine, sheep, etc.) and is preferably human β2 microglobulin (herein, also referred to as "hβ2M").

The "human β2 microglobulin" used herein may be a polynucleotide selected from the following polynucleotides (i) to (iii):
(i) a polynucleotide encoding a polypeptide consisting of the amino acid sequence as shown in SEQ ID NO: 36;
(ii) a polynucleotide encoding a polypeptide consisting of an amino acid sequence that has substitution, deletion, or addition of one or several amino acids in the amino acid sequence as shown in SEQ ID NO: 36, and has antigen presenting capacity specific for MHC class I by forming a complex with the α chain of the MHC class I; and
(iii) a polynucleotide encoding a polypeptide consisting of an amino acid sequence that has 90% or higher identity to the amino acid sequence as shown in SEQ ID NO: 36 and has antigen presenting capacity specific for MHC class I by forming a complex with the α chain of the MHC class I;
and preferably the polynucleotide (i).

The "MHC class I α3 region" used herein refers to an α3 region involved in binding to a coreceptor CD8 molecule expressed on CTL surface, and transmembrane region and intracellular region located on the C termini. The "MHC class I α3 region" used herein may be derived from a human or any non-human animal (mouse, rat, hamster, guinea pig, rabbit, pig, bovine, sheep, etc.) and is preferably mouse MHC class I α3 region (herein, also referred to as "mα3").

The "mouse MHC class I α3 region" used herein may be a polynucleotide selected from the following polynucleotides (iv) to (vi):
(iv) a polynucleotide encoding a polypeptide consisting of the amino acid sequence as shown in SEQ ID NO: 37;
(v) a polynucleotide encoding a polypeptide consisting of an amino acid sequence that has substitution, deletion, or addition of one or several amino acids in the amino acid sequence as shown in SEQ ID NO: 37 and has CD8 molecule binding ability; and
(vi) a polynucleotide encoding a polypeptide consisting of an amino acid sequence that has 90% or higher identity to the amino acid sequence as shown in SEQ ID NO: 37 and has CD8 molecule binding ability;
and preferably the polynucleotide (iv).

In one aspect of the present invention, the "polynucleotide encoding α1 and α2 regions of human HLA-A24" used herein may preferably be a polynucleotide selected from the following polynucleotides (p) to (t):
(p) a polynucleotide encoding a polypeptide consisting of the amino acid sequence as shown in SEQ ID NO: 34;
(q) a polynucleotide encoding a polypeptide consisting of an amino acid sequence having substitution, deletion, or addition of one or several amino acids in the amino acid sequence as shown in SEQ ID NO: 34;
(r) a polynucleotide encoding a polypeptide consisting of an amino acid sequence having 90% or higher identity to the amino acid sequence as shown in SEQ ID NO: 34;
(s) a polynucleotide consisting of the nucleotide sequence as shown in SEQ ID NO: 35; and
(t) a polynucleotide consisting of a nucleotide sequence having 90% or higher identity to the nucleotide sequence as shown in SEQ ID NO: 35;
and more preferably a polynucleotide selected from the polynucleotides (p) and (s).

Preferably, α1 and α2 regions encoded by the "polynucleotide encoding α1 and α2 regions of human HLA-A24" can present a polypeptide consisting of the amino acid sequence as shown in SEQ ID NO: 5 as an antigen. Preferably, these regions can present a polypeptide consisting of the amino acid sequence as shown in SEQ ID NO: 5 as an antigen and have CD8 molecule binding ability. Preferably, these regions can present a polypeptide consisting of the amino acid sequence as shown in SEQ ID NO: 5 as an antigen and have CD8 molecule binding ability, and the β2 microglobulin has preferably antigen presenting ability specific for MHC class I by forming a complex with the α chain of the MHC class I.

Whether or not a cell has these functions can be confirmed by, for example, $^{51}$Cr release assay, ELISA (e.g., measurement of IFN-γ) or ELISPOT assay (e.g., measurement of IFN-γ) using the cell of the present invention and CTL specific for the amino acid sequence as shown in SEQ ID NO: 5.

Host cells for use in establishment of the cell of the present invention are preferably an animal-derived cell line and are capable of forming a tumor when transplanted to an animal. More preferably, host cells are a mouse-derived cell line and are capable of forming a tumor when transplanted to a mouse. The tumor formed by the host cells is not limited and is preferably, for example, solid tumor such as melanoma or lymphoma, because growth and regression, etc. of the tumor are easily evaluated. The host cells are preferably B16F10 cells.

A vector for introducing a polynucleotide encoding an epitope peptide of a human tumor antigen derived from SART2 and a polynucleotide encoding α1 and α2 regions of human HLA-A24 to the host cells for use in establishment of the cell of the present invention is not particularly limited as long as the vector is replicable in the host cells. The vector can be appropriately selected according to the type of the host cells for introduction, an introduction method, etc. Examples thereof include plasmid DNA vectors and virus vectors. Examples of the plasmid DNA vectors include pCMV6 (OriGene Technologies, Inc.), piggyBac Transposon Vector (System Biosciences, LLC.), pCAG (FUJIFILM Wako Pure Chemical Corp.), and pcDNA3.1 (Thermo Fisher Scientific Inc.). Examples of the virus vectors include pMX (Cell Biolabs, Inc.), pLVSIN (Takara Bio Inc.), pAAV (Takara Bio Inc.), and pAdenoX (Clontech Laboratories, Inc.).

The host cell can be transformed with the vector by use of lipofection, electroporation, or the like. The obtained transformant can be cultured under adequate conditions using a medium containing an assimilable carbon source, nitrogen source, metal salt, vitamin, etc.

Whether or not the cell is a cell into which a polynucleotide encoding an epitope peptide of a human tumor antigen derived from SART2 and a polynucleotide encoding α1 and α2 regions of human HLA-A24 have been introduced can be confirmed, for example, by using methods for detecting expression of a polynucleotide encoding an epitope peptide of a human tumor antigen or the encoded polypeptide, and a polynucleotide encoding α1 and α2 regions of human HLA-A24 or the encoded polypeptide, and using the expression as an index.

The method for detecting expression of a polynucleotide encoding an epitope peptide of a human tumor antigen derived from SART2 can employ, as a primer, for example, a polypeptide specifically hybridizing to the polynucleotide as shown in SEQ ID NO: 29 or SEQ ID NO: 33 including a polynucleotide encoding PEP5, or a polynucleotide consisting of a nucleotide sequence complementary to the polynucleotide as shown in SEQ ID NO: 29 or SEQ ID NO: 33, and a detection method commonly used such as Northern blotting, Southern blotting, RT-PCR, real-time PCR, digital PCR, DNA microarray technique, in situ hybridization, or sequencing can be used.

The method for detecting expression of a polynucleotide encoding α1 and α2 regions of human HLA-A24 can employ, as a primer, for example, a polynucleotide specifically hybridizing to the polynucleotide as shown in SEQ ID NO: 31 or SEQ ID NO: 35 including a polynucleotide encoding the amino acid sequences of the α1 and α2 regions of human HLA-A24, or a polynucleotide consisting of a nucleotide sequence complementary to the polynucleotide as shown in SEQ ID NO: 31 or SEQ ID NO: 35, and the detection method commonly used as described above can be used.

Such primer is produced by a commonly known method, as a polynucleotide specifically hybridizing to the polynucleotide as shown in SEQ ID NO: 29 or SEQ ID NO: 33 or a polynucleotide consisting of a nucleotide sequence complementary to the polynucleotide as shown in SEQ ID NO: 29 or SEQ ID NO: 33. Also, such primer is produced by a commonly known method, as a polynucleotide specifically hybridizing to the polynucleotide as shown in SEQ ID NO: 31 or SEQ ID NO: 35 or a polynucleotide consisting of a nucleotide sequence complementary to the polynucleotide as shown in SEQ ID NO: 31 or SEQ ID NO: 35. The number of nucleotides in such primer is 10 to 50 nucleotides, preferably 10 to 40 nucleotides, and more preferably 10 to 30 nucleotides.

The primer does not have to be completely complementary as long as the primer specifically hybridizes to the polynucleotide as shown in SEQ ID NO: 29 or SEQ ID NO: 33 or a polynucleotide consisting of a nucleotide sequence complementary to the polynucleotide as shown in SEQ ID NO: 29 or SEQ ID NO: 33, or the polynucleotide as shown in SEQ ID NO: 31 or SEQ ID NO: 35 or a polynucleotide consisting of a nucleotide sequence complementary to the polynucleotide as shown in SEQ ID NO: 31 or SEQ ID NO: 35. Such a primer is a polynucleotide having 70% or higher, preferably 80% or higher, more preferably 90% or higher, more preferably 95% or higher, more preferably 98% or higher identity, to the corresponding nucleotide sequence, and a completely complementary polynucleotide is most preferable.

The primer for use in the method for detecting expression of a polynucleotide encoding an epitope peptide of a human tumor antigen derived from SART2 is preferably the primer set as shown in SEQ ID NO: 42 and SEQ ID NO: 43.

A detection method commonly used such as ELISA, Western blotting, flow cytometry, or immunohistochemical staining, for example, using an antibody specifically binding to the polypeptide as shown in SEQ ID NO: 5 can be used as the method for detecting expression of a polypeptide encoding an epitope peptide of a human tumor antigen derived from SART2. Flow cytometry is preferable. The antibody specifically binding to the polypeptide as shown in SEQ ID NO: 5 may be commercially available, or may be prepared by a commonly known method.

A detection method commonly used such as ELISA, Western blotting, flow cytometry, or immunohistochemical staining, for example, using an antibody specifically binding to the polypeptide as shown in SEQ ID NO: 30 or SEQ ID NO: 34 including HLA-A24 α1 and α2 regions can be used as the method for detecting expression of a polypeptide encoding α1 and α2 regions of human HLA-A24. Flow cytometry is preferable. The antibody specifically binding to the polypeptide as shown in SEQ ID NO: 30 or SEQ ID NO: 34 may be commercially available, or may be prepared by a commonly known method. Examples of commercially available antibody include anti-human HLA-A,B,C Antibody (Clone: W6/32, BioLegend, Inc.), Anti-HLA-A24 (Human) mAb (Clone: 22E1, MBL), and Anti-HLA A antibody (Clone: EP1395Y, Abcam plc), with anti-human HLA-A,B,C Antibody (Clone: W6/32, BioLegend, Inc.) being preferable. When such antibody is, for example, anti-human HLA-A,B,C Antibody (Clone: W6/32, BioLegend, Inc.), its labeled form such as a PE-labeled form, PE anti-human HLA-A,B,C Antibody (Clone: W6/32, BioLegend, Inc.) or an FITC-labeled form, FITC anti-human HLA-A,B,C Antibody (Clone: W6/32, BioLegend, Inc.) is also included in anti-human HLA-A,B,C Antibody (Clone: W6/32, BioLegend, Inc.).

For enabling in vivo evaluation, it is preferable that the cell of the present invention should form tumor in a non-immunodeficient non-human animal when transplanted to the non-immunodeficient non-human animal, and should not spontaneously regress. The cell can be confirmed not to spontaneously regress, by subcutaneously transplanting the cell of the present invention to, for example, a human HLA-A24 gene knock-in mouse (International Publication No. WO 2015/056774), and measuring a tumor size. It is preferable that the tumor size should not be reduced (the tumor size should be increased) for at least 20 days or longer after transplantation of the cell of the present invention to a non-immunodeficient non human animal. If the absence of regression of transplanted cells (increased tumor size) is confirmed in a drug non-administration group (control group) in an in vivo test period, the cells may be included in the cell of the present invention even if a period without spontaneous regression is shorter than 20 days.

In the present invention, the term "non-immunodeficient" in the non-immunodeficient non-human animal refers to having the inherent immune system or modified immune system of the animal. Thus, such non-immunodeficient animal excludes immunodeficient animals such as nude mice. The "non-human animal" is not particularly limited as long as the animal has β2 microglobulin loci and a foreign gene can be introduced thereto. A rodent is preferable, and a mouse or a rat is more preferable. A mouse is particularly preferable from the viewpoint of rearing and experimental operation.

The present invention also relates to the cell of the present invention for evaluating the antitumor effect of an epitope peptide of a human tumor antigen derived from SART2.

The present invention also relates to the cell of the present invention for evaluating the antitumor effect of a peptide having 4 linked epitopes and/or an immune checkpoint modulator.

The present invention also relates to a method for evaluating the antitumor effect of an epitope peptide of a human tumor antigen derived from SART2 using the cell of the present invention. The method is preferably performed using a human HLA-A24 gene knock-in non-immunodeficient non-human animal to which the cell of the present invention has been transplanted. In this context, the human HLA-A24 gene knock-in non-immunodeficient non human animal can be a non-immunodeficient non-human animal having α1 and α2 regions of human HLA-A24 and is preferably a human HLA-A24 gene knock-in mouse ($B2m^{tm2(HLA-A24/H-2Db/B2M)Tai}$ mouse) disclosed in International Publication No. WO 2015/056774.

In this method, the number of the cells of the present invention to be transplanted can be appropriately selected, and is preferably $1 \times 10^5$ to $1 \times 10^7$ cells/body, more preferably $1 \times 10^5$ to $5 \times 10^5$ cells/body, and more preferably $5 \times 10^5$ cells/body, for a human HLA-A24 gene knock-in mouse ($B2m^{tm2(HLA-A24/H-2Db/B2M)Tai}$ mouse). In the method, the amount of the epitope peptide of a human tumor antigen derived from SART2 administered per dose can be appropriately selected, and is preferably 10 to 1000 μg/body, more preferably 100 to 1000 μg/body, and more preferably 300 μg/body, for a human HLA-A24 gene knock-in mouse ($B2m^{tm2(HLA-A24/H-2Db/B2M)Tai}$ mouse).

Evaluation of the antitumor effect of epitope peptides of a human tumor antigen derived from SART2 using the cell of the present invention can be performed by a method comprising the following steps.

Specifically, the method can be performed by a method comprising the steps of:
(I) administering an epitope peptide of a human tumor antigen derived from SART2 to a human HLA-A24 gene knock-in non-immunodeficient non-human animal; and
(II) transplanting the cell of the present invention to the human HLA-A24 gene knock-in non-immunodeficient non-human animal.

Preferably, the method is a method comprising the following steps (I) and (II):
(I) a step of administering an epitope peptide of a human tumor antigen derived from SART2 to a human HLA-A24 gene knock-in mouse; and
(II) a step of transplanting the cell of the present invention to the human HLA-A24 gene knock-in mouse.

More preferably, the method is a method comprising the following steps (I) and (II):
(I) a step of administering twice or more an epitope peptide of a human tumor antigen derived from SART2 to a human HLA-A24 gene knock-in mouse; and
(II) a step of transplanting the cell of the present invention to the human HLA-A24 gene knock-in mouse after the step (I).

More preferably, the method is a method comprising the following steps (I) and (II):
(I) a step of administering three times or more an epitope peptide of a human tumor antigen derived from SART2 to a human HLA-A24 gene knock-in mouse; and
(II) a step of transplanting the cell of the present invention to the human HLA-A24 gene knock-in mouse after the step (I).

The present invention also relates to a method for evaluating the antitumor effect of a peptide having 4 linked epitopes and/or an immune checkpoint modulator using the cell of the present invention. The method is preferably performed using a human HLA-A24 gene knock-in non-immunodeficient non-human animal to which the cell of the present invention has been transplanted. In this context, the human HLA-A24 gene knock-in non-immunodeficient non-human animal can be a non-immunodeficient non-human animal having α1 and α2 regions of human HLA-A24 and is preferably a human HLA-A24 gene knock-in mouse ($B2m^{tm2(HLA-A24/H-2Db/B2M)Tai}$ mouse) disclosed in International Publication No. WO 2015/056774.

In this method, the number of the cells of the present invention to be transplanted can be appropriately selected, and is preferably $1 \times 10^5$ to $1 \times 10^7$ cells/body, more preferably $1 \times 10^5$ to $5 \times 10^5$ cells/body, and more preferably $5 \times 10^5$ cells/body, for a human HLA-A24 gene knock-in mouse ($B2m^{tm2(HLA-A24/H-2Db/B2M)Tai}$ mouse). In the method, the amount of the peptide having 4 linked epitopes administered per dose can be appropriately selected, and is preferably 10 to 1000 μg/body, more preferably 100 to 1000 μg/body, and more preferably 300 μg/body, for a human HLA-A24 gene knock-in mouse ($B2m^{tm2(HLA-A24/H-2Db/B2M)Tai}$ mouse). In the method, the amount of the immune checkpoint modulator administered per dose can be appropriately selected, and is preferably 10 to 1000 μg/body, more preferably 30 to 500 μg/body, and more preferably 50 to 200 μg/body, for a human HLA-A24 gene knock-in mouse ($B2m^{tm2(HLA-A24/H-2Db/B2M)Tai}$ mouse).

The method for evaluating the antitumor effect of a peptide having 4 linked epitopes and/or an immune checkpoint modulator using the cell of the present invention can comprise the following steps.

Specifically, the method can be performed by a method comprising the steps of:
(I) administering the peptide having 4 linked epitopes and/or the immune checkpoint modulator to a human HLA-A24 gene knock-in non-immunodeficient non-human animal; and
(II) transplanting the cell of the present invention to the human HLA-A24 gene knock-in non-immunodeficient non-human animal.

Preferably, the method is a method comprising the following steps (I) and (II):
(I) a step of administering the peptide having 4 linked epitopes and/or the immune checkpoint modulator to a human HLA-A24 gene knock-in mouse; and
(II) a step of transplanting the cell of the present invention to the human HLA-A24 gene knock-in mouse.

More preferably, the method is a method comprising the following steps (I) and (II):
(I) a step of administering twice or more the peptide having 4 linked epitopes to a human HLA-A24 gene knock-in mouse; and
(II) a step of transplanting the cell of the present invention to the human HLA-A24 gene knock-in mouse after the step (I).

More preferably, the method is a method comprising the following steps (I) to (III):
- (I) a step of administering three times or more the peptide having 4 linked epitopes to a human HLA-A24 gene knock-in mouse;
- (II) a step of transplanting the cell of the present invention to the human HLA-A24 gene knock-in mouse after the step (I); and
- (III) a step of administering the immune checkpoint modulator to the human HLA-A24 gene knock-in mouse after the step (I).

In the method of the present invention, evaluation of the antitumor effect of the peptide having 4 linked epitopes can be performed by a method comprising the following steps.

Specifically, the method can be performed by a method comprising the steps of:
- (I) administering the peptide having 4 linked epitopes to a human HLA-A24 gene knock-in non-immunodeficient non-human animal; and
- (II) transplanting the cell of the present invention to the human HLA-A24 gene knock-in non-immunodeficient non-human animal.

Preferably, the method is a method comprising the following steps (I) and (II):
- (I) a step of administering the peptide having 4 linked epitopes to a human HLA-A24 gene knock-in mouse; and
- (II) a step of transplanting the cell of the present invention to the human HLA-A24 gene knock-in mouse.

More preferably, the method is a method comprising the following steps (I) and (II):
- (I) a step of administering twice or more the peptide having 4 linked epitopes to a human HLA-A24 gene knock-in mouse; and
- (II) a step of transplanting the cell of the present invention to the human HLA-A24 gene knock-in mouse after the step (I).

More preferably, the method is a method comprising the following steps (I) and (II):
- (I) a step of administering three times or more the peptide having 4 linked epitopes to a human HLA-A24 gene knock-in mouse; and
- (II) a step of transplanting the cell of the present invention to the human HLA-A24 gene knock-in mouse after the step (I).

In the present invention, evaluation of the antitumor effect of the immune checkpoint modulator can be performed by a method comprising the following steps.

Specifically, the method can be performed by a method comprising the steps of:
- (I) administering the immune checkpoint modulator to a human HLA-A24 gene knock-in non-immunodeficient non-human animal; and
- (II) transplanting the cell of the present invention to the human HLA-A24 gene knock-in non-immunodeficient non-human animal.

Preferably, the method is a method comprising the following steps (I) and (II):
- (I) a step of administering the immune checkpoint modulator to a human HLA-A24 gene knock-in mouse; and
- (II) a step of transplanting the cell of the present invention to the human HLA-A24 gene knock-in mouse.

More preferably, the method is a method comprising the following steps (I) and (II):
- (I) a step of administering the immune checkpoint modulator to a human HLA-A24 gene knock-in mouse; and
- (II) a step of transplanting the cell of the present invention to the human HLA-A24 gene knock-in mouse on the same day as that of the step (I).

In the present invention, evaluation of the antitumor effects of the peptide having 4 linked epitopes and the immune checkpoint modulator can be performed by a method comprising the following steps.

Specifically, the method can be performed by a method comprising the steps of:
- (I) administering the peptide having 4 linked epitopes and the immune checkpoint modulator to a human HLA-A24 gene knock-in non-immunodeficient non-human animal; and
- (II) transplanting the cell of the present invention to the human HLA-A24 gene knock-in non-immunodeficient non-human animal.

Preferably, the method is a method comprising the following steps (I) and (II):
- (I) a step of administering the peptide having 4 linked epitopes and the immune checkpoint modulator to a human HLA-A24 gene knock-in mouse; and
- (II) a step of transplanting the cell of the present invention to the human HLA-A24 gene knock-in mouse.

More preferably, the method is a method comprising the following steps (I) and (II):
- (I) a step of administering twice or more the peptide having 4 linked epitopes to a human HLA-A24 gene knock-in mouse; and
- (II) a step of transplanting the cell of the present invention to the human HLA-A24 gene knock-in mouse after the step (I).

More preferably, the method is a method comprising the following steps (I) to (III):
- (I) a step of administering three times or more the peptide having 4 linked epitopes to a human HLA-A24 gene knock-in mouse;
- (II) a step of transplanting the cell of the present invention to the human HLA-A24 gene knock-in mouse after the step (I); and
- (III) a step of administering the immune checkpoint modulator to the human HLA-A24 gene knock-in mouse after the step (I).

The method of the present invention described above may comprise the step of evaluating the antitumor effect of the peptide having 4 linked epitopes and/or the immune checkpoint modulator after the steps described above. The antitumor effect can be evaluated by using, for example, suppression of tumor growth of transplanted cells in an animal, regression and disappearance of the tumor, or increase in survival rate as an index.

The "antitumor effect of the epitope peptide of a human tumor antigen derived from SART2" and the "antitumor effect of the peptide having 4 linked epitopes" can be evaluated, for example, by using a human HLA-A24 gene knock-in mouse, subcutaneously administering three times the epitope peptide of a human tumor antigen derived from SART2 or the peptide having 4 linked epitopes to the mouse, then subcutaneously transplanting the cell of the present invention to the mouse, and measuring a tumor size to confirm whether or not the antitumor effect is observed.

The "antitumor effect of the immune checkpoint modulator" can be evaluated, for example, by using a human HLA-A24 gene knock-in mouse, intravenously or intraperitoneally administering the immune checkpoint modulator to the mouse on the same day as that of transplantation of the cell of the present invention, and measuring a tumor size to confirm whether or not the antitumor effect is observed.

EXAMPLES

Next, the present invention will be described in more detail with reference to Examples. However, the present invention is not limited by these examples by any means. Those having an ordinary knowledge in the art could make various changes or modification without departing from the technical idea of the present invention.

For easier understanding of the present invention, SEQ ID NOs: 29 to 43 described herein are explained in Table 3 below.

TABLE 3

| | |
|---|---|
| Nucleotide sequence of SART2-93 | SEQ ID NO: 29 |
| Amino acid sequence of HLA-A24 α1 and α2 regions | SEQ ID NO: 30 |
| Nucleotide sequence of HLA-A24 α1 and α2 regions | SEQ ID NO: 31 |
| Amino acid sequence of signal sequence + SART2-93 | SEQ ID NO: 32 |
| Nucleotide sequence of signal sequence + SART2-93 | SEQ ID NO: 33 |
| Amino acid sequence of hβ2M-HLA-A24 α1 and α2 regions-mα3 | SEQ ID NO: 34 |
| Nucleotide sequence of hβ2M-HLA-A24 α1 and α2 regions-mα3 | SEQ ID NO: 35 |
| Amino acid sequence of human β2 microglobulin (except for signal sequence) | SEQ ID NO: 36 |
| Amino acid sequence of mouse MHC class I α3 region | SEQ ID NO: 37 |
| Sense primer for hβ2M-HLA-A24 α1 + α2-mα3 amplification | SEQ ID NO: 38 |
| Antisense primer for hβ2M-HLA-A24 α1 + a2-mα3 amplification | SEQ ID NO: 39 |
| Sense primer for signal sequence + SART2-93 introduction | SEQ ID NO: 40 |
| Antisense primer for signal sequence + SART2-93 introduction | SEQ ID NO: 41 |
| Sense primer for signal sequence + SART2-93 detection | SEQ ID NO: 42 |
| Antisense primer for signal sequence + SART2-93 detection | SEQ ID NO: 43 |

Example 1 Peptide Synthesis and Purification

Peptides TPV07 and TPV08 having 4 linked epitopes were synthesized using an automated peptide synthesizer Prelude (Protein Technologies, Inc.) by the solid-phase synthesis method based on the 9-fluorenylmethyl-oxycarbonyl (Fmoc) method. Specifically, an amino acid with its a-amino group protected with a Fmoc group and its side chain functional group protected with a general protective group was condensed onto Wang ChemMatrix resin under 1-(mesithylene-2-sulfonyl)-3-nitro-1,2,4-triazole/Nmethylimidazole/dichloromethane conditions, to complete supporting of a C terminal amino acid onto the resin. A deblocking solution (20% piperidine/N,N-dimethylformamide (DMF)) was injected thereinto, to remove the Fmoc group. Then, an amino acid with its a-amino group protected with a Fmoc group and its side chain functional group protected with a general protective group was condensed thereonto under 1-[bis (dimethylamino) methylene]-5-chloro-IH-benzo-triazolium 3-oxide hexafluorophosphate (HCTU)/N-methylmorpholine (NMM)/DMF conditions, to synthesize a dipeptide. By repeating the procedures of deprotecting the Fmoc group with a deblocking solution and condensing an amino acid under HCTU/NMM/DMF conditions, peptides comprising sequences of interest were synthesized. After completion of synthesis of protected peptide resin, removal of protective groups on the peptide side chains as well as excision of free peptides from the resin were performed by conducting a reaction for 4 hours in a deprotective solution (2.5% triisopropylsilane, 2.5% water, 2.5% 1,2-ethanedithiol, 92.5% trifluoroacetic acid) added to the protected peptide resin. The resin was filtered off, and with the addition of the resulting filtrate to cold ether, peptides were recovered in the form of precipitates. The resulting various synthetic peptides were purified using the Proteonavi column (Shiseido Japan Co., Ltd.) and a solvent system with an aqueous solution of 0.1% TF A and acetonitrile. After the final process of purification, the purity of the peptides was confirmed by the CAPCELL PAK UG120 column (Shiseido Japan Co., Ltd.) and the HPLC system (Hitachi, Ltd.). The molecular weight was also confirmed by the ESI-MS system (Synapt HDMS, Waters Corp.). The peptides were lyophilized, stored at cool temperature in the dark, and then subjected to the examples described below.

Table 4 shows the molecular weights of TPV07 and TPV08 measured by mass spectrometry (MS). FIGS. 1 to 4 show HPLC chromatograms and mass spectra of TPV07 and TPV08.

TABLE 4

| Peptide | Molecular weight (Calculated) | Molecular weight (Deconvoluted) |
|---|---|---|
| TPV07 | 5396.03 | 5395.20 |
| TPV08 | 5682.41 | 5682.00 |

TPV01 to TPV06, TPV09 and TPV10 may be synthesized in accordance with the method described in, for example, International Publication No. WO 2015/060235, or may be synthesized in the same manner as the method for synthesizing TPV07 and TPV08 as described above. All the peptides were obtained with purity of 90% or more.

Example 2 Establishment of B16F10.A24/SART2$^{93-101}$ Cell Line and EL4.A24/SART2$^{93-101}$ Cell Line B2m$^{tm2(HLA-A24/H-2Db/B2M)Tai}$ mice were prepared by the method described in Example 8 of International Publication No. WO 2015/056774. This mouse can express an artificial chimeric protein comprising a human β2 microglobulin, HLA-A24 α1 and α2 regions, and a mouse MHC class I α3 region linked to each other.

The spleen was harvested from the obtained mouse, ground with slide glass, and then hemolyzed using BD Pharm Lyse (BD Bioscience) to prepare a single-cell suspension. RNA was extracted from the obtained single-cell suspension using RNeasy kit (Qiagen N.V.). Specifically, after addition of 350 μL of Buffer RLT to 1×10$^6$ cells, the mixture was added to QIAshredder spin column (Qiagen N.V.) and centrifuged (15000 rpm, 2 min), and a flow-through fraction was recovered. After addition of 350 μL of an aqueous solution of 70% ethanol to the recovered RNA solution, the mixture was added to RNeasy Mini column and centrifuged (10000 rpm, 15 sec). The column was further washed with 350 μL of Buffer RW1 and then treated with DNase using RNase-Free DNase set (Qiagen N.V.). The column was washed with 350 µL of Buffer RW1, followed by RNA purification according to the protocol of RNeasy Mini Kit. 30 µL of RNase Free H$_2$O was added to the RNA thus purified, to recover total RNA.

cDNA was synthesized from the obtained total RNA using Superscript III First-Strand Synthesis System for RT-PCR (Thermo Fisher Scientific Inc.). Specifically, 2 µg of the total RNA was suspended in 8 µL of purified water. 1 µL of oligo (dT)$_{20}$ and 1 µL of 10 mM dNTP were added to the suspension, and the mixture was incubated at 65° C. for 5 minutes. After cooling for 2 minutes on ice, 2 µL of 10×RT buffer, 1 µL of 25 mM MgCl$_2$, 2 µL of 0.1 M DTT, 1 µL of RNaseOUT (40 U/µL), and 1 µL of SuperScript III RT were added thereto and mixed. The mixture was incubated at 50° C. for 50 minutes and then treated at 85° C. for 5 minutes, to terminate the reaction.

A polynucleotide encoding the artificial chimeric protein described above having the sequence as shown in SEQ ID NO: 35 was obtained by conducting PCR (94° C. for 2 min→30 cycles each involving 94° C. for 30 sec, 55° C. for 30 sec, and 68° C. for 2 min→68° C. for 2 min→4° C.) using the synthesized cDNA as a template, Primer 1

(TCAAGCTTAACTAGCATGGCCGTCATGGC: SEQ ID NO: 38)

as a sense primer, Primer 2

(TTAAACCTCGAGTGCTCACGCTTTACAATCTCGGAGAGA: SEQ ID NO: 39)

as an antisense primer, and KOD-Plus-ver. 2 (Toyobo Co., Ltd.). The amplified polynucleotide was inserted to PiggyBac Transposon Vector (System Biosciences, LLC.) using InFusion HD Cloning Kit (Clontech Laboratories, Inc.) to obtain plasmid vector A having the sequence of SEQ ID NO: 35.

Subsequently, in order to obtain a polynucleotide encoding PEP5, PCR (25 cycles each involving 98° C. for 10 sec, 55° C. for 15 sec, and 68° C. for 6 min→68° C. for 3 min→4° C.) was conducted using the plasmid vector A having the sequence of SEQ ID NO: 35 thus obtained as a template, Primer 3

(CTCAAATTTCATTCCAGCGGGCACTGTAGTCTGCCCAGGTCTGGGT: SEQ ID NO: 40)

as an antisense primer, Primer 4

(GCAGACTACAGTGCCCGCTGGAATGAAATTTGAGCACTCGAGGTTTA A: SEQ ID NO: 41)

as a sense primer, and PrimeSTAR GXL DNA Polymerase (Takara Bio Inc.). As a result, plasmid vector B having the nucleotide sequence as shown in SEQ ID NO: 33 including a nucleotide sequence encoding a signal sequence and PEP5 within the PiggyBac Transposon Vector was obtained.

The thus prepared plasmid vectors A and B, together with Super PiggyBac Transposase Expression Vector (System Biosciences, LLC.) were introduced into a mouse melanoma cell line B16F10 (American Type Culture Collection, ATCC), using Lipofectamine LTX Reagent with PLUS Reagent (Thermo Fisher Scientific Inc.). Single-clone cells were obtained from the cells thus transfected by use of the limiting dilution technique.

The plasmid vectors A and B prepared as described above and Super PiggyBac Transposase Expression Vector (System Biosciences, LLC.) were also introduced into a mouse lymphoma cell line EL4 (ATCC) using Cell line Nucleofector Kit L (Lonza Group AG) and Nucleofector Device (Lonza Group AG). Single-clone cells were obtained from the cells thus transfected by use of the limiting dilution technique.

The obtained single-clone cells were recovered, and RNA was extracted therefrom using RNeasy kit (Qiagen N.V.). Specifically, after addition of 350 µL of Buffer RLT to 5×10$^5$ cells, the mixture was added to QIAshredder spin column (Qiagen N.V.) and centrifuged (15000 rpm, 2 min), and a flow-through fraction was recovered. After addition of 350 µL of an aqueous solution of 70% ethanol to the recovered RNA solution, the mixture was added to RNeasy Mini column and centrifuged (10000 rpm, 15 sec). The column was further washed with 350 µL of Buffer RW1 and then treated with DNase using RNase-Free DNase set (Qiagen N.V.). The column was washed with 350 µL of Buffer RW1, followed by RNA purification according to the protocol of RNeasy Mini Kit. 30 µL of RNase Free H$_2$O was added to the RNA thus purified, to recover total RNA.

cDNA was synthesized from the obtained RNA using SuperScript VILO cDNA Synthesis Kit (Thermo Fisher Scientific Inc.). Specifically, 2 µg of the total RNA was suspended in 14 µL of DPEC-treated water and mixed with 4 µL of 5×VILO Reaction Mix and 2 µL of 10× SuperScript Enzyme Mix. The mixture was incubated at 25° C. for 10 minutes and at 42° C. for 60 minutes and then treated at 85° C. for 5 minutes, to terminate the reaction.

In order to confirm expression of the polynucleotide encoding PEP5 in the obtained single-clone cells, PCR (94° C. for 2 min→30 cycles each involving 98° C. for 10 sec, 55° C. for 30 sec, and 68° C. for 30 sec→68° C. for 1 min→4° C.) was conducted using the synthesized cDNA as a template, Primer 5

(ATGGCCGTCATGGC: SEQ ID NO: 42)

as a sense primer, Primer 6

(TCAAATTTCATTCCAGCG: SEQ ID NO: 43)

as an antisense primer, and KOD-Plus-ver. 2 (Toyobo Co., Ltd.), and amplification of the polynucleotide sequence as shown in SEQ ID NO: 33 was confirmed by agarose gel electrophoresis. The amplification of the polynucleotide having the sequence as shown in SEQ ID NO: 33 could not be confirmed in B16F10 and EL4 cells without gene introduction, whereas the amplification of the polynucleotide having the sequence as shown in SEQ ID NO: 33 could be confirmed in the obtained single clones. Thus, PEP5-expressing cells were confirmed to be obtained by the introduction of the plasmid vector B.

In order to analyze expression of an HLA molecule in the obtained single-clone cells, the cells were stained with PE Anti-human HLA-A,B,C Antibody (Clone: W6/32, BioLegend, Inc.). The cells thus stained were analyzed using BD FACSVerse (BD Biosciences). As a result, elevation in fluorescence intensity caused by the antibody staining could not be confirmed in B16F10 and EL4 cells without gene introduction, whereas elevation in fluorescence intensity caused by the antibody staining could be confirmed in the obtained single clones. Thus, HLA-A24-expressing cells were confirmed to be obtained by the introduction of the plasmid vector A.

Specifically, the obtained cells were confirmed to be cells expressing HLA-A24 and also expressing PEP5 (B16F10.A24/SART2$^{93-101}$ cells and EL4.A24/SART2$^{93-101}$ cells).

Example 3 Confirmation of Engraftment of B16F10.A24/SART2$^{93-101}$ Cell Line and EL4.A24/SART2$^{93-101}$ Cell Line The B16F10.A24/SART2$^{93-101}$ cell line and the EL4.A24/SART2$^{93-101}$ cell line obtained in Example 2 were cultured using Dulbecco's Modified Eagle's Medium (Sigma-Aldrich Co. LLC.) containing 10% FBS. For passages, the cells were subcultured at a ratio of 1:25 to 1:40 twice a week at 37° C. in a 5% $CO_2$ incubator.

The B16F10.A24/SART2$^{93-101}$ cell line or the EL4.A24/SART2$^{93-101}$ cell line was subcutaneously transplanted at 1×10$^5$ cells/0.1 mL to the right flank region of each 9- to 11-week-old B2 m$^{tm2(HLA-A24/H-2Db/B2M)Tai}$ mouse.

The major axis and minor axis of tumor were measured using Digimatic calipers from 7 days after transplantation, and a tumor volume (TV) was calculated according to the following formula.

TV (mm$^3$)=Major axis (mm)×Minor axis (mm)× Minor axis (mm)/2

Figure 5:
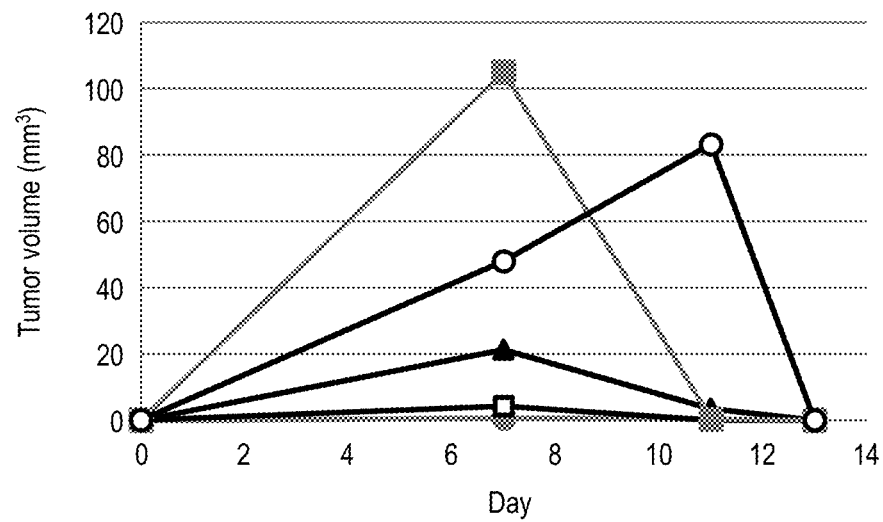
FIG. 5a shows change in tumor volume when an EL4.A24/SART2$^{93-101}$ cell line was transplanted to mice.
FIG. 5b shows change in tumor volume when a B16F10.A24/SART2$^{93-101}$ cell line was transplanted to mice.
Figure 5:
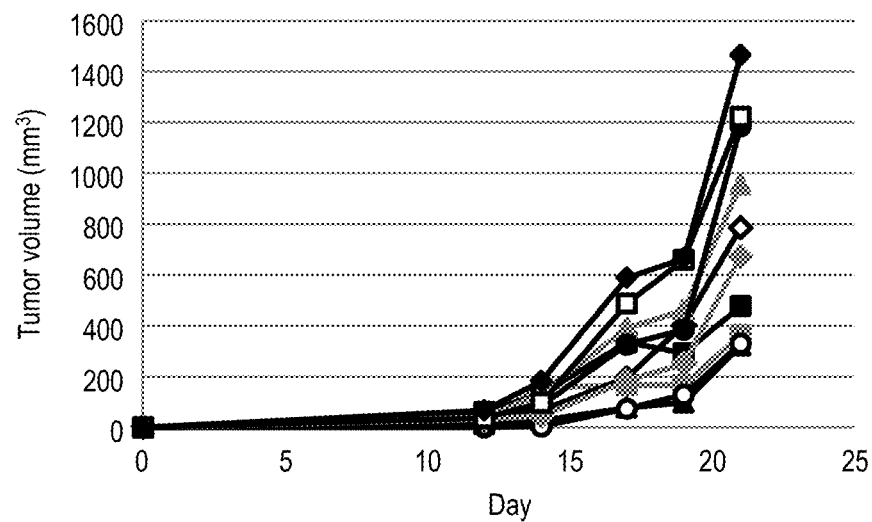

The results are shown in FIG. 5.

As shown in FIG. 5a, when the EL4.A24/SART2$^{93-101}$ cell line was transplanted, although temporal engraftment (growth) was found in some mice, spontaneous regression was confirmed by the 13th day in all the mice (five). On the other hand, as shown in FIG. 5b, when the B16F10.A24/SART2$^{93-101}$ cell line was transplanted, engraftment as tumor without spontaneous regression was confirmed in all the mice (ten) even after 20 days after transformation. Specifically, only the B16F10.A24/SART2$^{93-101}$ cell line was confirmed to be usable in in vivo tests.

Example 4 Effect of TPV06 and Anti-Mouse PD-1 Antibody Used m Combination in B16F10.A24/SART2$^{93-101}$ Cell Line Subcutaneously Transplanted Model 8-week-old B2m$^{tm2(HLA-A24/H-2Db/B2M)Tai}$ mice were randomly assigned to groups each involving 15 animals. The day of grouping was defined as Day 0. A 6 mg/mL peptide solution was prepared by dissolving a peptide having 4 linked epitopes TPV06 in distilled water (Otsuka Pharmaceutical Factory Inc.), and filled into the B Braun Injekt syringe (B. Braun Melsungen AG). After the equivalent amount of Montanide™ ISA 51 VG (SEPPIC) was filled into another syringe, these syringes were connected to each other via a connector, and the peptide solution was thoroughly mixed with Montanide™ ISA 51 VG to prepare an emulsion. Also, an emulsion of distilled water mixed with the equivalent amount of Montanide™ ISA 51 VG was prepared as a vehicle control. Each of these emulsions was subcutaneously administered weekly in amounts of 100 μL each in the vicinity of base of tail of each B2m$^{tm2(HLA-A24/H-2Db/B2M)Tai}$ mouse, and administrations were carried out three times in total (Days 0, 7, and 14).

GoInVivo™ Purified anti-mouse CD279 (PD-1) (Clone: RMP-1-14, BioLegend, Inc.) was prepared as an anti-mouse PD-1 antibody (anti-mPD-1 Ab) into 1 mg/mL using D-PBS (FUJIFILM Wako Pure Chemical Corp.) immediately before administration. One week after final administration of the emulsions (Day 21), the anti-mouse PD-1 antibody was intraperitoneally administered at 100 μg/body.

The B16F10.A24/SART2$^{93-101}$ cell line was cultured using Dulbecco's Modified Eagle's Medium (Sigma-Aldrich Co. LLC.) containing 10% FBS. B16F10.A24/SART2$^{93-101}$ was subcultured at a ratio of 1:25 to 1:40 twice a week at 37° C. in a 5% $CO_2$ incubator.

On the same day (Day 21) after administration of the anti-mouse PD-1 antibody, a cell suspension prepared using D-PBS (FUJIFILM Wako Pure Chemical Corp.) was subcutaneously transplanted at 5×10$^5$ cells/0.1 mL to the right flank region of the mouse.

The major axis and minor axis of tumor were measured using Digimatic calipers from 7 days after transplantation of the B16F10.A24/SART2$^{93-101}$ cell line, and a tumor volume (TV) was calculated according to the following formula.

TV (mm$^3$)=Major axis (mm)×Minor axis (mm)× Minor axis (mm)/2

Figure 6:
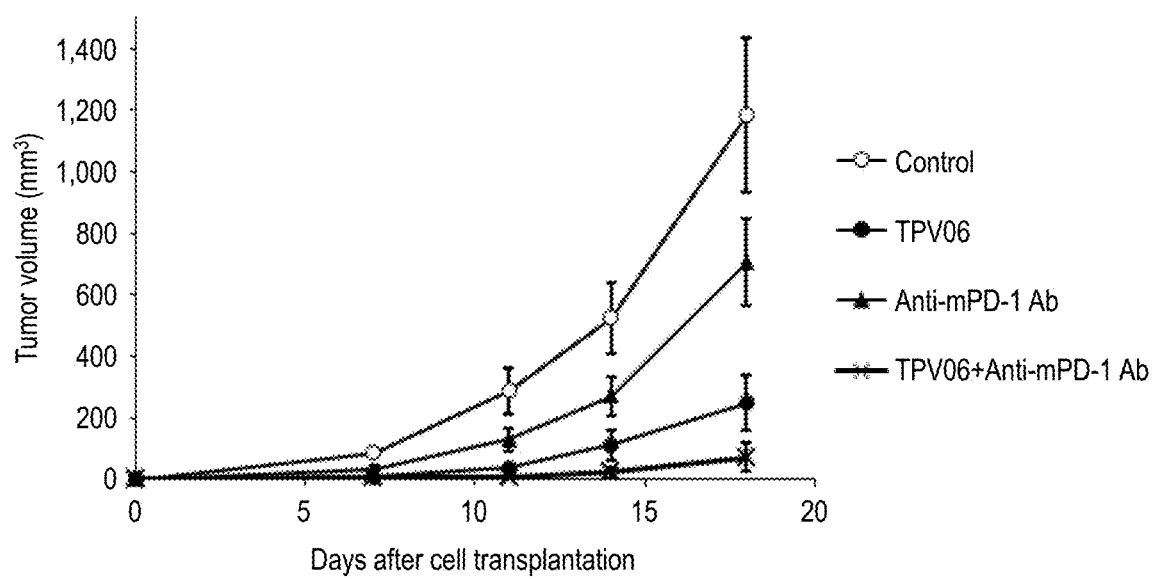
FIG. 6 shows the effect of TPV06 and an anti-mouse PD-1 antibody used in combination on tumor growth in mouse models in which a B16F10.A24/SART2$^{93-101}$ cell line was transplanted.

As shown in FIG. 6 (change in tumor volume after cell transplantation), both TPV06 and the anti-mouse PD-1 antibody had a tumor growth inhibitory effect when each used alone, as compared with the control group, whereas use of them in combination more significantly inhibited tumor growth.

Table 5 below shows results obtained on 18 days after cell transplantation. In the table, the value of TV represents the average value of each group. A rate of relative change in tumor volume (T/C) was calculated from TV according to the following formula.

T/C(%)=(Average TV of Each Drug Administration Group)/(Average TV of the control group)×100

Body weight was measured using an electronic balance for animals, and a rate of change in body weight (BWC) was calculated from the body weight measured on Day 0 (the day of grouping, BW0) and the body weight on 18 days after cell transplantation (BW) according to the following formula.

Rate of change in body weight BWC (%)=(BW−BW0)/BW0×100

The proportion of tumor-free mice (Tumor Free) on 57 days after cell transplantation was calculated according to the following formula.

Tumor Free (%)=(The number of tumor-free mice in each group)/(The number of mice used in the study in each group)×100

TABLE 5

|  | 18 days after transplantation | | | 57 days after transplantation |
|---|---|---|---|---|
|  | TV(mean ± SE) | T/C | BWC (%) | Tumor Free (%) |
| Control | 1183.14 ± 205.04 | — | 28.3 | 0.0 |
| TPV06 | 247.45 ± 89.16 | 20.9 | 27.0 | 13.3 |
| Anti-mPD-1 Ab | 703.36 ± 141.55 | 59.5 | 26.9 | 0.0 |
| TPV06 + Anti-mPD-1 Ab | 71.45 ± 46.72 | 6.0 | 23.8 | 53.3 |

On 18 days after cell transplantation, the TPV06 or anti-mouse PD-1 antibody single administration group and the TPV06+anti-mouse PD-1 antibody combined administration group had a lower value of TV than that of the control group, showing an antitumor effect. In addition, the TPV06+ anti-mouse PD-1 antibody combined administration group had a lower value of TV than that of the TPV06 or anti-mouse PD-1 antibody single-drug group, showing a stronger antitumor effect. On 57 days after cell transplantation, 53.3% of the mice in the TPV06+anti-mouse PD-1 antibody combined administration group were tumor-free. In addition, the TPV06+anti-mouse PD-1 antibody combined administration group was confirmed to have an improved survival rate on 57 days after cell transplantation, as compared with the single-drug administration group.

The rate of change in average body weight of the combined administration group indicated that no enhancement of toxicity was involved, as compared with the TPV06 or anti-mouse PD-1 antibody single-drug group.

Example 5 Effect of TPV06 and Anti-Mouse PD-L1 Antibody Used in Combination in B16F10.A24/SART2$^{93-101}$ Cell Line Subcutaneously Transplanted Model 9-week-old B2m$^{tm2(HLA-A24/H-2Db/B2M)Tai}$ mice were randomly assigned to groups each involving 15 animals. The day of grouping was defined as Day 0.

This study was conducted in the same way as in Example 4 except that an anti-mouse PD-L1 antibody was used instead of the anti-mouse PD-1 antibody. GoInVivo™ Purified anti-mouse CD274 (B7-H1, PD-L1) (Clone: 10F.9G2, BioLegend, Inc.) was prepared as an anti-mouse PD-L1 antibody (anti-mPD-L1 Ab) into 1 mg/mL using D-PBS (FUJIFILM Wako Pure Chemical Corp.) immediately before administration. One week after final administration of the emulsions (Day 21), the anti-mouse PD-L1 antibody was intraperitoneally administered at 200 µg/body.

Figure 7:
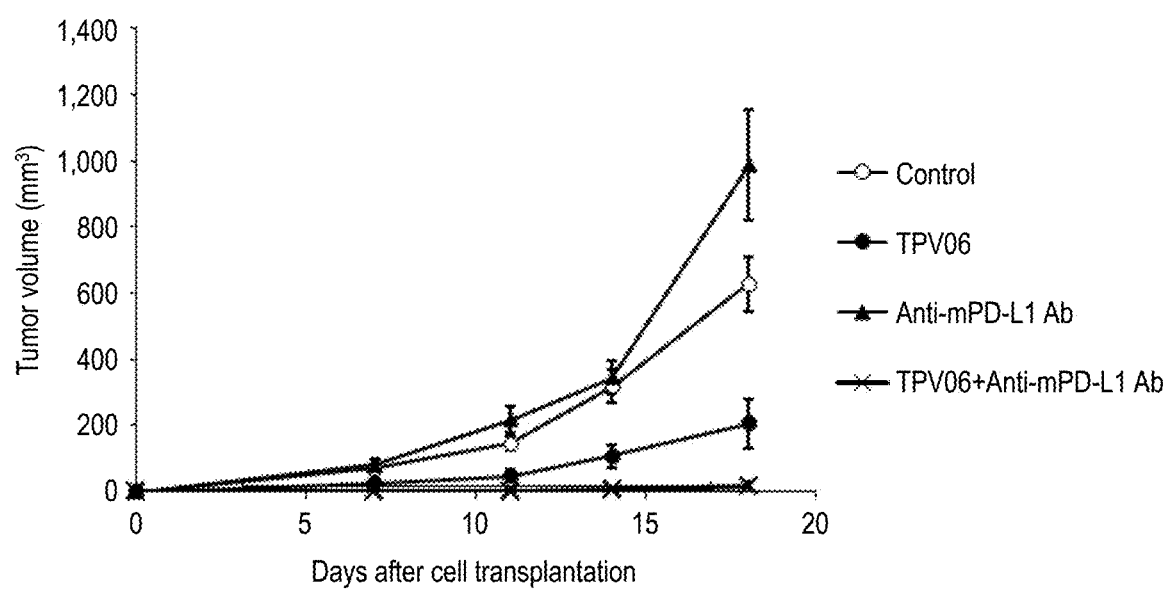
FIG. 7 shows the effect of TPV06 and an anti-mouse PD-L1 antibody used in combination on tumor growth in mouse models in which a B16F10.A24/SART2$^{93-101}$ cell line was transplanted.

As shown in FIG. 7 (change in tumor volume after cell transplantation), TPV06 had a tumor growth inhibitory effect when used alone, as compared with the control group, whereas the anti-mouse PD-L1 antibody was not effective. However, use of TPV06 and the anti-mouse PD-L1 antibody in combination more significantly inhibited tumor growth.

Table 6 below shows a tumor volume, a rate of relative change in tumor volume and change in body weight (BWC) on 18 days after cell transplantation, and a proportion of tumor-free mice on 57 days after cell transplantation.

TABLE 6

| | 18 days after transplantation | | | 57 days after transplantation |
|---|---|---|---|---|
| | TV(mean ± SE) | T/C | BWC (%) | Tumor Free (%) |
| Control | 627.2 ± 82.7 | — | 19 | 0.0 |
| TPV06 | 205.8 ± 73.9 | 32.8 | 21.9 | 0.0 |
| Anti-mPD-L1 Ab | 987.4 ± 168.9 | 157.4 | 21.2 | 0.0 |
| TPV06 + Anti-mPD-L1 Ab | 17.7 ± 14.9 | 2.8 | 20.4 | 66.7 |

On 18 days after cell transplantation, the TPV06 single administration group and the TPV06+anti-mouse PD-L1 antibody combined administration group had a lower value of TV than that of the control group, showing an antitumor effect. In addition, the TPV06+anti-mouse PD-L1 antibody combined administration group had a lower value of TV than that of the TPV06 or anti-mouse PD-L1 antibody single-drug group, showing a stronger antitumor effect. On 57 days after cell transplantation, 66.7% of the mice in the TPV06+anti-mouse PD-L1 antibody combined administration group were tumor-free. In addition, the TPV06+anti-mouse PD-L1 antibody combined administration group was confirmed to have an improved survival rate on 57 days after cell transplantation, as compared with the single-drug administration groups.

The rate of change in average body weight in the combined administration group indicated that no enhancement of toxicity was involved, as compared with the TPV06 or anti-mouse PD-L1 antibody single-drug group.

Example 6 Effect of TPV07 or TPV08 and Anti-Mouse PD-1 Antibody Used in Combination in B16F10.A24/SART2$^{93-101}$ Cell Line Subcutaneously Transplanted Model 9-week-old B2 m$^{tm2(HLA-A24/H-2Db/B2M)Tai}$ mice were randomly assigned to groups each involving 15 animals. The day of grouping was defined as Day 0.

This study was conducted in the same way as in Example 4 except that TPV07 or TPV08 was used instead of TPV06 as a peptide having 4 linked epitopes. TPV07 and TPV08, as in TPV06, were each prepared into 6 mg/mL using distilled water (Otsuka Pharmaceutical Factory Inc.) and then mixed with the equivalent amount of Montanide™ ISA 51 VG (SEPPIC) to prepare an emulsion, which was administered. This Example did not include an anti-mouse PD-1 antibody single administration group.

Figure 8:
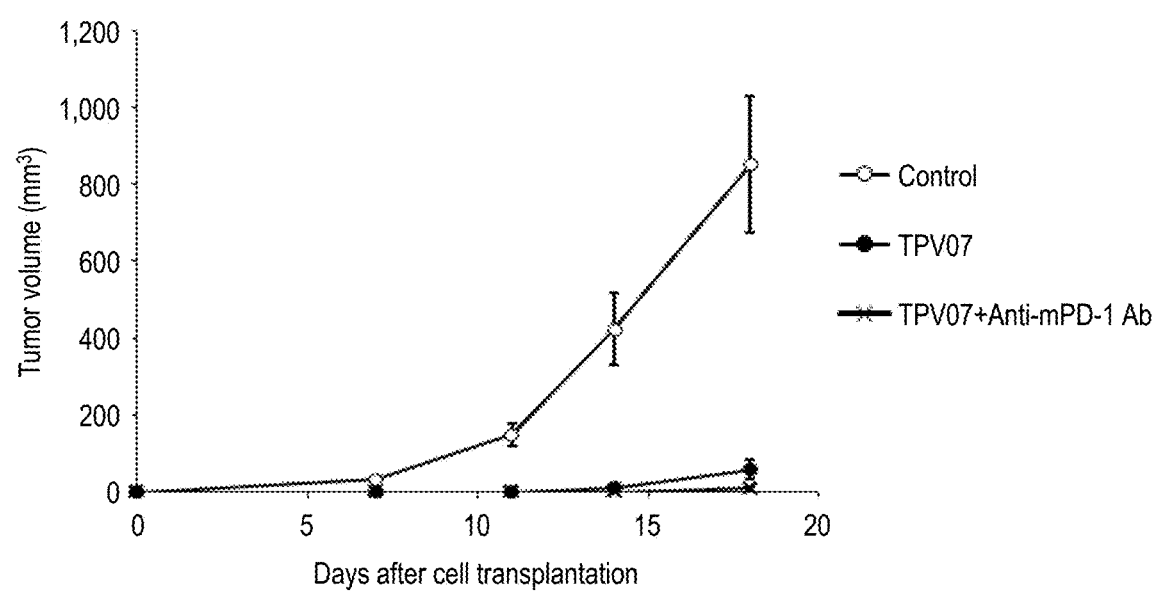
FIG. 8 shows the effect of TPV07 and an anti-mouse PD-1 antibody used in combination on tumor growth in mouse models in which a B16F10.A24/SART2$^{93-101}$ cell line was transplanted.
Figure 9:
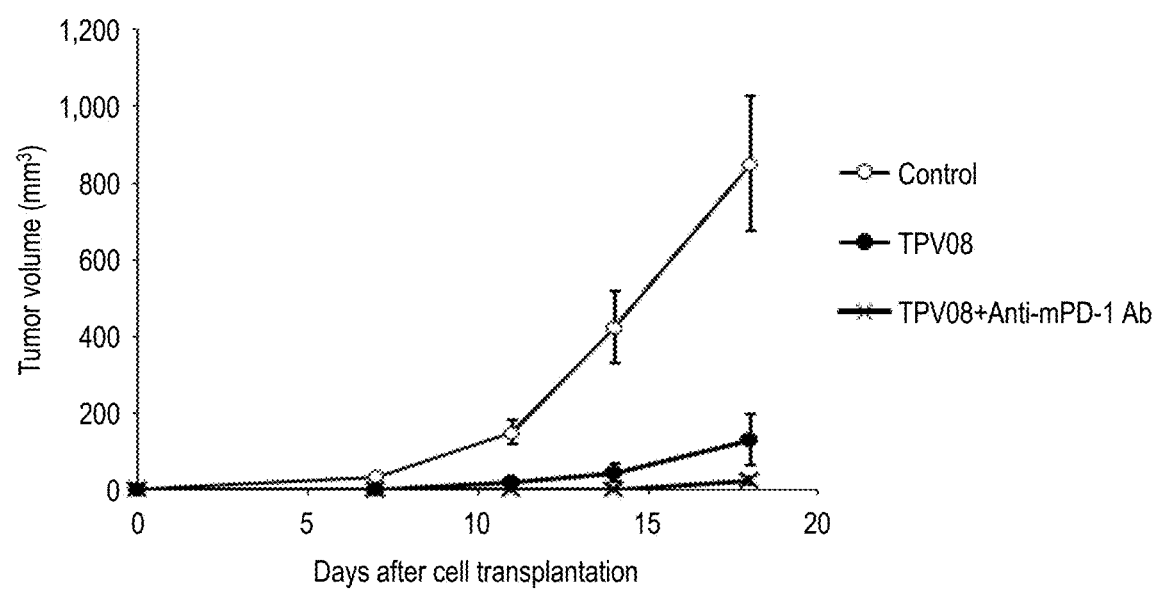
FIG. 9 shows the effect of TPV08 and an anti-mouse PD-1 antibody used in combination on tumor growth in mouse models in which a B16F10.A24/SART2$^{93-101}$ cell line was transplanted.

FIGS. 8 and 9 show change in tumor volume after cell transplantation. Table 7 shows a tumor volume, a rate of relative change in tumor volume and change in body weight (BWC) on 18 days after cell transplantation, and a proportion of tumor-free mice on 56 days after cell transplantation.

TABLE 7

| | 18 days after transplantation | | | 56 days after transplantation |
|---|---|---|---|---|
| | TV(mean ± SE) | T/C | BWC (%) | Tumor Free (%) |
| Control | 850.8 ± 176.6 | — | 23.1 | 0.0 |
| TPV07 | 58.2 ± 24.4 | 6.8 | 18.9 | 13.3 |
| TPV07 + Anti-mPD-1 Ab | 8.6 ± 6.8 | 1.0 | 18.6 | 80.0 |
| TPV08 | 129.7 ± 67.0 | 15.2 | 21.7 | 6.7 |
| TPV08 + Anti-mPD-1 Ab | 21.6 ± 12.7 | 2.5 | 16.1 | 40.0 |

As shown in FIGS. 8 and 9, both TPV07 and TPV08 had a high tumor growth inhibitory effect when each used alone, as compared with the control group, whereas use of them in combination with the anti-mouse PD-1 antibody more significantly inhibited tumor growth.

As shown in Table 7, on 18 days after cell transplantation, the TPV07 or TPV08 single administration group and the TPV07+anti-mouse PD-1 antibody or TPV08+anti-mouse PD-1 antibody combined administration group had lower values of TV than that of the control group, showing an antitumor effect. In addition, the TPV07+anti-mouse PD-1 antibody combined administration group had a lower value of TV than that of the TPV07 single-drug group, showing a stronger antitumor effect. Likewise, the TPV08+anti-mouse PD-1 antibody combined administration group had a lower value of TV than that of the TPV08 single-drug group, showing a stronger antitumor effect. On 56 days after cell transplantation, 80.0% of the mice in the TPV07+anti-mouse PD-1 antibody combined administration group were tumor-free, and 40.0% of the mice in the TPV08+anti-mouse PD-1 antibody combined administration group were tumor-free. In addition, the TPV07+anti-mouse PD-1 antibody or TPV08+anti-mouse PD-1 antibody combined administration group was confirmed to have an improved survival rate on 56 days after cell transplantation, as compared with the single-drug administration group.

The rate of change in average body weight in the combined administration group indicated that no enhancement of toxicity was involved, as compared with the TPV07 or TPV08 single-drug group.

Example 7 Effect of 3 Mixed Peptides Having 4 Linked Epitopes (TPV06, TPV011 and TPV012) and Anti-Mouse PD-1 Antibody Used in Combination in B16F10.A24/SART293-101 Cell Line Subcutaneously Transplanted Model 9-week-old B2 m$^{tm2(HLA-A24/H-2Db/B2M)Tai}$ mice were randomly assigned to groups each involving 15 animals. The day of grouping was defined as Day 0.

This study was conducted in the same way as in Example 4 except that a total of 3 mixed peptides having 4 linked epitopes composed of TPV06 and other two peptides having 4 linked epitopes (TPV011 and TPV012) were used instead of TPV06. Specifically, the study was conducted with a control group, a group of 3 mixed peptides having 4 linked epitopes (TPV06, TPV011 and TPV012), an anti-mouse PD-1 antibody group and a combined administration group of 3 mixed peptides having 4 linked epitopes (TPV06, TPV011 and TPV012)+anti-mouse PD-1 antibody. The 3 mixed peptides having 4 linked epitopes (TPV06, TPV011 and TPV012) were prepared into 6 mg/mL each of TPV06, TPV011 and TPV012 (i.e., total amount of the peptides: 18 mg/mL), using distilled water (Otsuka Pharmaceutical Factory Inc.), and mixed with the equivalent amount of Montanide™ ISA 51 VG (SEPPIC) to prepare an emulsion, which was administered.

As a result, the combined administration group of 3 mixed peptides having 4 linked epitopes (TPV06, TPV011 and TPV012)+anti-mouse PD-1 antibody was able to be confirmed to have an improved survival rate on 56 days after cell transplantation, as compared with the single administration group of the 3 mixed peptides having 4 linked epitopes (TPV06, TPV011 and TPV012) or the anti-mouse PD-1 antibody.

The rate of change in average body weight in the combined administration group indicated that no enhancement of toxicity was involved, as compared with the single-drug group.

All publications, patents and patent applications cited herein are incorporated herein by reference in their entirety.

The invention claimed is:

1. A combined formulation comprising a peptide having 4 linked epitopes comprising 4 CTL epitope peptides linked via linkers and a PD-1 pathway antagonist in combination,
   wherein the PD-1 pathway antagonist is at least one selected from the group consisting of an anti-PD-1 antibody, an anti-PD-L1 antibody, and an anti-PD-L2 antibody,
   wherein the peptide having 4 linked epitopes comprises:
      the epitope peptide as shown in SEQ ID NO: 5,
      the epitope peptide as shown in SEQ ID NO: 6,
      the epitope peptide as shown in SEQ ID NO: 9, and
      one epitope peptide selected from the group consisting of the epitope peptide as shown in SEQ ID NO: 2, the epitope peptide as shown in SEQ ID NO: 4 and the epitope peptide as shown in SEQ ID NO: 10, at the C terminus
      wherein the 4 linked epitopes are linked via linkers, wherein the peptide optionally further comprises a peptide sequence consisting of hydrophilic amino acids,
      wherein the linker is an arginine dimer composed of two arginine residues linked to each other,
      wherein the peptide sequence consisting of hydrophilic amino acids is linked to the N terminus and is composed of an arginine trimer composed of three arginine residues linked to each other or an arginine tetramer composed of four arginine residues linked to each other.

2. The combined formulation of claim 1, wherein the combined formulation further comprises a peptide having the sequence of SEQ ID NO: 44 and a peptide having the sequence of SEQ ID NO: 45.

3. The combined formulation of claim 2, wherein the combined formulation comprises a peptide having the sequence of SEQ ID NO: 24, a peptide having the sequence of SEQ ID NO: 44, and a peptide having the sequence of SEQ ID NO: 45.

4. A method for treating a cancer in a patient by administering a peptide having 4 linked epitopes comprising 4 CTL epitope peptides linked via linkers and a PD-1 pathway antagonist,
   wherein the PD-1 pathway antagonist is at least one selected from the group consisting of an anti-PD-1 antibody, an anti-PD-L1 antibody, and an anti-PD-L2 antibody,
   wherein the peptide having 4 linked epitopes comprises:
      the epitope peptide as shown in SEQ ID NO: 5,
      the epitope peptide as shown in SEQ ID NO: 6,
      the epitope peptide as shown in SEQ ID NO: 9, and
      one epitope peptide selected from the group consisting of the epitope peptide as shown in SEQ ID NO: 2, the epitope peptide as shown in SEQ ID NO: 4 and the epitope peptide as shown in SEQ ID NO: 10, at the C terminus
      wherein the 4 linked epitopes are linked via linkers, wherein the peptide optionally further comprises a peptide sequence consisting of hydrophilic amino acids,
      wherein the linker is an arginine dimer composed of two arginine residues linked to each other,
      wherein the peptide sequence consisting of hydrophilic amino acids is linked to the N terminus and is composed of an arginine trimer composed of three arginine residues linked to each other or an arginine tetramer composed of four arginine residues linked to each other.

5. The method according to claim 4, wherein the peptide having 4 linked epitopes is as shown in SEQ ID NO: 24, SEQ ID NO: 25, or SEQ ID NO: 26.

6. The method according to claim 4, wherein the PD-1 pathway antagonist is at least one selected from the group consisting of an anti-PD-1 antibody and an anti-PD-L1 antibody.

7. The method according to claim 4, wherein the anti-PD-1 antibody is nivolumab or pembrolizumab, and the anti-PD-L1 antibody is atezolizumab, durvalumab or avelumab.

8. The method according to claim 4, wherein the peptide having 4 linked epitopes is administered to the patient before administration of the PD-1 pathway antagonist, simultaneously with administration of the PD-1 pathway antagonist, or after administration of the PD-1 pathway antagonist.

9. The method of claim 4, wherein the method comprises administering to the patient the peptide together with a peptide having the sequence of SEQ ID NO: 44 and a peptide having the sequence of SEQ ID NO: 45, as a mixture.

10. The method of claim 9, wherein the method comprises administering to the patient a peptide having the sequence of SEQ ID NO: 24, a peptide having the sequence of SEQ ID NO: 44, and a peptide having the sequence of SEQ ID NO: 45, as a mixture.

11. A method for enhancing the antitumor effect of a PD-1 pathway antagonist, comprising administering a peptide having 4 linked epitopes to a patient,
   wherein the PD-1 pathway antagonist is at least one selected from the group consisting of an anti-PD-1 antibody, an anti-PD-L1 antibody, and an anti-PD-L2 antibody,
   wherein the peptide having 4 linked epitopes comprises:
      the epitope peptide as shown in SEQ ID NO: 5,
      the epitope peptide as shown in SEQ ID NO: 6,
      the epitope peptide as shown in SEQ ID NO: 9, and
      one epitope peptide selected from the group consisting of the epitope peptide as shown in SEQ ID NO: 2, the epitope peptide as shown in SEQ ID NO: 4 and the epitope peptide as shown in SEQ ID NO: 10, at the C terminus
      wherein the 4 linked epitopes are linked via linkers, wherein the peptide optionally further comprises a peptide sequence consisting of hydrophilic amino acids,
      wherein the linker is an arginine dimer composed of two arginine residues linked to each other,
      wherein the peptide sequence consisting of hydrophilic amino acids is linked to the N terminus and is composed of an arginine trimer composed of three arginine residues linked to each other or an arginine tetramer composed of four arginine residues linked to each other.

12. The method according to claim 11, wherein the peptide having 4 linked epitopes is administered to the patient before administration of the PD-1 pathway antagonist, simultaneously with administration of the PD-1 pathway antagonist, or after administration of the PD-1 pathway antagonist.

13. The method of claim 11, wherein the method comprises administering the peptide together with a peptide having the sequence of SEQ ID NO: 44 and a peptide having the sequence of SEQ ID NO: 45, as a mixture.

14. The method of claim 13, wherein the method comprises administering a peptide having the sequence of SEQ ID NO: 24, a peptide having the sequence of SEQ ID NO: 44, and a peptide having the sequence of SEQ ID NO: 45, as a mixture.

* * * * *